US008609818B2

(12) United States Patent
Leppard et al.

(10) Patent No.: US 8,609,818 B2
(45) Date of Patent: Dec. 17, 2013

(54) GENERATION OF ANTI-FN14 MONOCLONAL ANTIBODIES BY EX-VIVO ACCELERATED ANTIBODY EVOLUTION

(75) Inventors: John Benjamin Leppard, Mukilteo, WA (US); Christi L Wood, Snohomish, WA (US); W Jason Cummings, Bellevue, WA (US); Munehisa Yabuki, Seattle, WA (US); Nancy Maizels, Seattle, WA (US); Daniel S Allison, Lake Forest Park, WA (US); Larry W Tjoelker, Kirkland, WA (US)

(73) Assignee: Omeros Corporation, Seattle, WA (US)

( * ) Notice: Subject to any disclaimer, the term of this patent is extended or adjusted under 35 U.S.C. 154(b) by 0 days.

(21) Appl. No.: 13/416,752

(22) Filed: Mar. 9, 2012

(65) Prior Publication Data

US 2012/0258121 A1      Oct. 11, 2012

Related U.S. Application Data

(60) Provisional application No. 61/451,477, filed on Mar. 10, 2011, provisional application No. 61/512,236, filed on Jul. 27, 2011.

(51) Int. Cl.
*C07K 16/00* (2006.01)
*C07K 16/46* (2006.01)
*C07K 16/28* (2006.01)

(52) U.S. Cl.
USPC ................ 530/387.1; 530/387.3; 530/388.22; 530/391.1; 530/391.7

(58) Field of Classification Search
None
See application file for complete search history.

(56) References Cited

U.S. PATENT DOCUMENTS

| | | |
|---|---|---|
| 2002/0110853 A1 | 8/2002 | Wiley |
| 2004/0033225 A1 | 2/2004 | Browning et al. |
| 2008/0286271 A1 | 11/2008 | Ashkenazi et al. |
| 2010/0061985 A1 | 3/2010 | Rennert |
| 2010/0093033 A1 | 4/2010 | Maizels et al. |

FOREIGN PATENT DOCUMENTS

| | | | |
|---|---|---|---|
| EP | 1 566 636 A1 | 8/2005 | |
| WO | 2009/029315 A2 | 3/2009 | |
| WO | WO2012005328 | * | 1/2012 |

OTHER PUBLICATIONS

Vajdos et al. J. Mol. Biol. Jul. 5, 2002, 320(2):415-28.*
Brown et al J. Immuno. May 1996, 3285-91.*
Barbas et al., "Human autoantibody recognition of DNA," *PNAS* 92:2529-2533, Mar. 1995.
Barbas et al., "Recognition of DNA by Synthetic Antibodies," *J Am Chem Soc* 116:2161-2162, 1994.
Beiboer et al., "Guided Selection of a Pan Carcinoma Specific Antibody Reveals Similar Binding Characteristics yet Structural Divergence Between the Original Murine Antibody and its Human Equivalent," *J Mol Biol* 296:833-849, 2000.
Bradley et al., "Tumor necrosis factor receptor-associated factors (TRAFs)," *Oncogene* 20:6482-6491, 2001.
Buerstedde et al., "Light chain gene conversion continues at high rate in an ALV-induced cell line," *EMBO J* 9(3):921-927, 1990.
Culp et al., "Antibodies to TWEAK Receptor Inhibit Human Tumor Growth through Dual Mechanisms," *Clin Cancer Res* 16(2):497-508, Jan. 15, 2010.
Cumbers et al., "Generation and iterative affinity maturation of antibodies in vitro using hypermutating B-cell lines," *Nat Biotechnol* 20:1129-1134, Nov. 2002.
Cummings et al., "Chromatin Structure Regulates Gene Conversion," *PLos Biol* 5(10):e246, Oct. 2007, 11 Pages.
Cummings et al., "Genetic Variation Stimulated by Epigenetic Modification," *PLoS One* 3(12):e4075, Dec. 2007, 9 Pages.
Feng et al., "The Fn14 Immediate-Early Response Gene is Induced During Liver Regeneration and Highly Expressed in Both Human and Murine Hepatocellular Carcinomas," *Am J Pathol* 156(4):1253-1261, Apr. 2000.
Han et al., "Identification of Differentially Expressed Genes in Pancreatic Cancer Cells Using cDNA Microarray[1]" *Cancer Res* 62:2890-2896, May 15, 2002.
Hotta et al., "Direct targeting of fibroblast growth factor-inducible 14 protein protects against renal ischemia reperfusion injury," *Kidney International* 79:179-188, 2011.
Klimka et al., "Human anti-CD30 recombinant antibodies by guided phage antibody selection using cell panning," *British J Cancer* 83(2):252-260, 2000.
Maizels, "Immunoglobulin Gene Diversification," *Annu Rev Genet* 39:23-46, 2005.
Marks et al., "By-passing immunization: building high affinity human antibodies by chain shuffling," *Bio/Technology* 10:779-783, Jul. 1992.
McLane et al., "Transplantation of a 17-amino acid α-helical DNA-binding domain into an antibody molecule confers sequence-dependent DNA recognition," *PNAS* 92:5214-5218, May 1995.
Meighan-Mantha et al., "The Mitogen-inducible *Fn14* Gene Encodes a Type I Transmembrane Protein that Modulates Fibroblast Adhesion and Migration*," *J Biol Chem* 274(46):33166-33176, Nov. 12, 1999.
Nishibori et al., "Humanization of chicken monoclonal antibody using phage-display system," *Mol Immunol* 43:634-642, 2006.
Rader et al., "A phage display approach for rapid antibody humanization: Designed combinatorial V gene libraries," *PNAS* 95:8910-8915, Jul. 1998.
Seo et al., "Rapid generation of specific antibodies by enhanced homologous recombination," *Nat Biotechnol* 23(6):731-735, Jun. 2005.
Tran et al., "The Human Fn14 Receptor Gene is Up-Regulated in Migrating Glioma Cells in Vitro and Overexpressed in Advanced Glial Tumors," *Am J Pathol* 162(4):1313-1321, Apr. 2003.

(Continued)

*Primary Examiner* — Maher Haddad
(74) *Attorney, Agent, or Firm* — Tineka J. Quinton; Marcia S. Kelbon

(57) ABSTRACT

The present invention relates generally to anti-FN14 antibodies. In particular, the anti-FN14 antibodies described herein are useful for the treatment of diseases, such as a variety of cancers, associated with expression of FN14.

38 Claims, 23 Drawing Sheets

(56) References Cited

OTHER PUBLICATIONS

Tsurushita et al., "Humanization of a chicken anti-IL-12 monoclonal antibody," *J Immunol Methods* 295:9-19, 2004.

Watts et al., "Identification of Fn14/TWEAK receptor as a potential therapeutic target in esophageal adenocarcinoma," *Int J Cancer* 121:2132-2139, 2007.

Willis et al., "The Fibroblast Growth Factor-Inducible 14 Receptor is Highly Expressed in HER2-Positive Breast Tumors and Regulates Breast Cancer Cell Invasive Capacity," *Mol Cancer Res* 6(5):725-734, May 2008.

Winkles, "The TWEAK-Fn14 cytokine-receptor axis: discovery, biology and therapeutic targeting," *Nature Rev Drug Discov* 7(5):411-425, May 2008.

Yabuki et al., "The MRE11-RAD5O-NBS1 complex accelerates somatic hypermutation and gene conversion of immunoglobulin variable regions," *Nat Immunol* 6(7):730-736, Jul. 2005.

Yabuki et al., "E2A Acts in *cis* in $G_1$ Phase of Cell Cycle to Promote Ig Gene Diversification[1]," *J Immunol* 182:408-415, 2009.

\* cited by examiner

Heavy Chain VDJ sequences:

```
                    1                                                             63
SEQ ID NO:64  HP1VDJ  AVTLDESGGGLQTPGGALSLVCKASGFTFSSNAMGWVRQAPGKGLEWVAGIDDDGSGTRYAPA
SEQ ID NO:65  FN14_FS10  ..............................YD.A....E..................R...
SEQ ID NO:68  FN14_PS4   ..............................YD.F....E..................R...
SEQ ID NO:66  FN14_FS17  ..............................YD.A....E..................R...
SEQ ID NO:67  FN14_FS24  ..............................YD.A....E..........X.......R...

64                                                            125
              HP1VDJ  VKGRATISRDNGQSTLRLQLNNLRAEDTGTYYCTKCAYSSGCDYEGGYIDAWGHGTEVIVSS
              FN14_FS10  ............................................................
              FN14_PS4   ........................................TG..................
              FN14_FS17  ........................................TG..................
              FN14_FS24  .......................................G.TG.................
```

Fig. 3A

Light Chain VJ sequences:

```
                              1                                                           60
SEQ ID NO:22   VJ_DT40        ALTQPASVSANLGGTVKITCSGGGS--YAGSYYYGWYQQKSPGSAPVTVIYDNDKRPSDI
SEQ ID NO:23   FN14_FS10      ...........................P.E.......SY.............A....L..Y.N.
SEQ ID NO:24   FN14_FS17      ...........................P.E.......SY.............A....L..Y.N.
SEQ ID NO:25   FN14_FS24      .................S.........P.E.......SY.............A....L..Y.N.
SEQ ID NO:27   FN14_PS4A      .................S.........P.E.......SY.............A....L..Y.N.
SEQ ID NO:26   FN14_PS4B      ...........................P.E.......SY..................Y.N.

61                                              109
               VJ_DT40        PSRFSGSLSGGSTNTLTITGVRADDEAVYFCGSADNSGAAFGAGTTLTVL
               FN14_10        ...............................I.................
               FN14_17        ...............................I.................
               FN14_24        ...............................I.................
               FN14_PS4A      ...............................I.................
               FN14_PS4B      ...............................I.................
```

```
                    10         20         30         40         50         60
          1234567890123456789012345678901234567890123456789012345678901234567890
SEQ ID NO:68 PS4H   AVTLDESGGGLQTPGGALSLVCKASGFTFSSYDMFWVRQBPGKGLEWVAGIDDDSGGRRYAPAVKG
SEQ ID NO:58 hPS4H  EVQLVESGGGLVQPGGSLRLSCAASGFTFSSYDMFWVRQAPGKGLEWVAGIDDDSGGRRYAPAVKG
SEQ ID NO:88 HII1   EVQLVESGGGLVQPGGSLRLSCAASGFTFS----WVRQAPGKGLEWVS----------------

70         80         90        100        110
          67890123456789012abc3456789012345678901234567890abcdefgh1234567890123
PS4H                RATISRDNGQSTLRLQLNNLRAEDTGTYYCTKCAYSSGCDYEGGYIDAWGHGTEVTVSS
hPS4H               RATISRDNSKNTLYLQMNSLRAEDTAVYYCTKCAYSSGCDYEGGYIDAWGQGTLVTVSS
HII1                RFTISRDNSKNTLYLQMNSLRAEDTAVYYCAR--------------WGQGTLVTVSS
```

VL

```
                    11         20         30         40         50
          1234567890123456789012345678901234567890123456789a0123456789012345 6
SEQ ID NO:26 PS4L  **ALTQPASVSANPGETVKITCSGGGSSYYAGSYYYGWYQQKSPGSAPVTVIYYNNKRPS
SEQ ID NO:56 hPS4L **ELTQPPSVSVSPGQTARITCSGGGSSYYAGSYYYGWYQQK*PGQAPVTVIYYNNKRPS
SEQ ID NO:87 LIII1  SYELTQPPSVSVSPGQTARITC--------------WYQQK*PGQAPVTVIY-------

60         70         80         90        100
          78901234567890123456789012345678901234567890123456a
PS4L                DIPSRFSGSLSGSTNTLTITGVRADDEAVYFCGSIDNSGAAFGAGTTLTVL
hPS4L               GIPERFSGSLSGSTNTLTITISGVQAEDEADYYCGSIDNSGAAFGGGTKLTVL
LIII1               GIPERFSGSGSNSGNTATLTITISGVQAEDEADYYC--------FGGGTKLTVL
```

| SEQ ID NO: | | |
|---|---|---|
| SEQ ID NO: 67 | FS24H | |
| SEQ ID NO: 90 | hFS24H | |
| SEQ ID NO: 88 | HIII | |

```
                1         2         3         4         5         6
       123456789012345678901234567890123456789012345678901234567890123a345
FS24H  AVTLDESGGGLQTPGGALSLVCKASGFTFSSYDMAWVRQEPGKGLEWVAGIDNDGSGRRYAPAVKG
hFS24H EVQLVESGGGLVQPGGSLRLSCAASGFTFSSYDMAWVRQAPGKGLEWVAGIDYDGSGRRYAPAVKG
HIII   EVQLVESGGGLVQPGGSLRLSCAASGFTFS------WVRQAPGKGLEWVS---------------

7         8         9         100        110
       6789012345678901234567890abcdefgh1234567890abcdefgh1234567890123
FS24H  RATISRDNGQSTLRLQLNNLRAEDTGTYYCTKCGYTGGCDYEGGYIDAWGBGTEVIVSS
hFS24H RATISRDNSKNTLYLQMNSLRAEDTAVYYCTKCGYTGGCDYEGGYIDAWGQGTLVTVSS
HIII   RFTISRDNSKNTLYLQMNSLRAEDTAVYYCAR----------------WGQGTLVTVSS
```

VL

| SEQ ID NO: | | |
|---|---|---|
| SEQ ID NO: 25 | FS24L | |
| SEQ ID NO: 91 | hFS24L | |
| SEQ ID NO: 87 | LIII | |

```
               1         2         3         4         5
       123456789012345678901234567abcd8901234567890123456789012345 6
FS24L  **ALTQPASVSANPGETVKITCSGGGSSYYAGSYYGWYQQKAPGSAPVTLIYNNKRPS
hFS24L **ELTQPPSVSVSPGQTARITCSGGGSSYYAGSYYGWYQQK*PGQAPVTLIYNNKRPS
LIII   SYELTQPPSVSVSPGQTARITC----------------WYQQK*PGQAPVLVIY---

6         7         8         9         100
       789012345678901234567890123456789012345678901234 56a
FS24L  DIPSRFSGSLSGSTNTLTITGVRADDEAVYFCGSIDNSGAAFGAGTTLTVL
hFS24L GIPERFSGSLSGSTNTLTITSGVQAEDEADYCCGSIDNSGAAFGGGTKLTVL
LIII   GIPERFSGSNSGNTATLTITSGVQAEDEADYC----------FGGGTKLTVL
```

*Fig. 8*

GENERATION OF ANTI-FN14 MONOCLONAL ANTIBODIES BY EX-VIVO ACCELERATED ANTIBODY EVOLUTION

SEQUENCE LISTING

The Sequence Listing associated with this application is provided in text format in lieu of a paper copy, and is hereby incorporated by reference into the specification. The name of the text file containing the Sequence Listing is 980087_403_SEQUENCE_LISTING.txt. The text file is about 68 KB, was created on Mar. 9, 2012, and is being submitted electronically via EFS-Web.

BACKGROUND

1. Technical Field

The present invention relates generally to anti-FN14 antibodies. In particular, the anti-FN14 antibodies described herein are useful for the treatment of diseases, such as a variety of cancers and inflammatory diseases, associated with expression of FN14.

2. Description of the Related Art

The TWEAK protein (gene name TNFSF12), which has also been called CD255 and Apo3L, is a member of the tumor necrosis factor (TNF) family and was isolated in a screen for RNA that hybridized to an erythropoietin probe (Chicheportiche et al., *J. Biol. Chem.* 272:32401-32410 (1997)). The mouse and human peptides have an unusually high degree of conservation, including 93% amino acid identity in the receptor binding domain. TWEAK, shown to be efficiently secreted from cells, is abundantly expressed in many tissues, including heart, brain, placenta, lung, liver, skeletal muscle, kidney, pancreas, spleen, lymph nodes, thymus, appendix, and peripheral blood lymphocytes.

TWEAK has been implicated in many biological processes. For instance, HT29 cells treated with IFN and TWEAK were shown to undergo apoptosis; however, TWEAK's ability to induce apoptosis is weak and only a small number of cell types are susceptible (Chicheportiche et al., *J. Biol. Chem.* 272:32401-32410 (1997)). In contrast, TWEAK has also been shown to induce angiogenesis and proliferation of endothelial cells in a VEGF-independent pathway (Lynch et al., *J. Biol. Chem.* 274:8455-8459 (1999)). Astrocytes are specifically bound and stimulated by TWEAK. TWEAK can infiltrate an inflamed brain to influence astrocyte behavior. Astrocytes exposed to TWEAK secrete high levels of IL-6 and IL-8, as well as upregulate ICAM-1 expression (Saas et al., *GLIA* 32:102-107 (2000)).

FN14 (gene name TNFRSF12A), also known as TWEAKR and CD266, is an inducible TWEAK receptor that is linked to numerous intracellular signaling pathways, including the NF-kB pathway. FN14 has been shown to be induced by FGF, calf serum and phorbol ester treatment and is expressed at relatively high levels in heart, kidney, lung, skin, skeletal muscle, ovary and pancreas tissues, as well as in hepatocellular carcinoma modules and other cancer cell lines, and at lower levels in normal liver tissues. The TWEAK-FN14 signaling pathway appears to play a role in tissue repair and it has been implicated in cancer, chronic autoimmune diseases and acute ischemic stroke (Winkles, J. A. *Nature Reviews* 7:411 (2008)).

FN14 is a growth factor-regulated immediate-early response gene that decreases cellular adhesion to the extracellular matrix and reduces serum-stimulated growth and migration (Meighan-Mantha et al., *J. Biol. Chem.* 274:33166-33176 (1999)). FN14 is the smallest member of the TNF receptor superfamily. Proteins in this superfamily are type I transmembrane proteins which belong to one of two subgroups. The first subgroup of proteins contains a death domain motif in the intracellular portion of the protein which interacts with cellular factors that activate the apoptotic pathway (P. W. Dempsey et al, *Cytokine Growth Factor Rev* 2003; 14:193-209). Proteins in the second subgroup, such as FN14, lack the death domain but possess a domain that interacts with TNF receptor-associated and other cellular factors that regulate a variety of responses including proliferation, differentiation, and in certain cell types, immunoregulatory functions (Bradley J R and Pober J S *Oncogene* 2001; 20:6482-91). FN14 has a highly conserved 53 amino acid extracellular domain (92.4% identity between mouse and human sequences) and is overexpressed in many but not all tumor types, making it a target of therapeutic interest (Feng, S. L. et al. *Am J Pathol* 156, 1253-1261 (2000); Han H et al. *Cancer Res* 62, 2890-2896 (2002); Tran N. L. et al. *Am J Pathol* 162, 1313-1321 (2003); Watts G. S. et al., *Int J Cancer* 121, 2132-2139 (2007); Willis A. L. et al., *Mol Cancer Res* 6, 725-734 (2008)).

BRIEF SUMMARY

In certain embodiments according to the present disclosure, there is provided an isolated antibody, or an antigen-binding fragment thereof, that binds to human FN14, comprising (a) a heavy chain variable region comprising the VHCDR1, VHCDR2 and VHCDR3 amino acid sequences set forth in SEQ ID NOs: 79, 92 and 93, respectively; and (b) a light chain variable region comprising the comprising the VLCDR1, VLCDR2 and VLCDR3 amino acid sequences set forth in SEQ ID NOs:86, 39 and 94, respectively.

In certain embodiments the VHCRD2 of the heavy chain variable region according to (a) comprises SEQ ID NO:82. In certain embodiments the heavy chain variable region according to (a) comprises SEQ ID NO:84. In certain embodiments the VHCRD2 of the heavy chain variable region according to (a) comprises SEQ ID NO:81. In certain embodiments the VHCRD3 of the heavy chain variable region according to (a) comprises SEQ ID NO:83. In certain embodiments the VHCRD3 of the heavy chain variable region according to (a) comprises SEQ ID NO:76. In certain embodiments the VLCDR3 of the light chain variable region according to (b) comprises SEQ ID NO:41. In certain embodiments the VLCDR3 of the light chain variable region according to (b) comprises SEQ ID NO:36. In certain embodiments the heavy chain variable region comprises the amino acid sequence set forth in SEQ ID NO:67. In certain embodiments the light chain variable region comprises the amino acid sequence set forth in SEQ ID NO:25. In certain embodiments the heavy chain variable region comprises the amino acid sequence set forth in SEQ ID NO:66.

According to certain other embodiments the above described isolated antibody, or antigen binding fragment thereof, is a humanized antibody or antigen binding fragment thereof. In certain further embodiments the light chain variable region comprises the amino acid sequence set forth in SEQ ID NO:91. In certain embodiments the heavy chain variable region comprises the amino acid set forth in SEQ ID NO:90.

In certain embodiments of the present invention, the herein described antibody is selected from a single chain antibody, a ScFv, a univalent antibody lacking a hinge region, and a minibody. In certain other embodiments of the present invention, the herein described antibody is selected from a Fab, a Fab' fragment, a F(ab')$_2$ fragment and a whole antibody. In certain other embodiments the antibody is conjugated to a drug or a toxin. In certain embodiments the herein described isolated antibody comprises a human IgG Fc domain. In certain further embodiments the human IgG Fc domain is modified such that the antibody has enhanced ADCC activity as compared to the antibody having the unmodified human IgG Fc domain.

According to certain other embodiments of the present invention there is provided an isolated antibody, or an antigen-binding fragment thereof, that binds to human FN14, comprising a heavy chain variable region comprising any one of the amino acid sequences set forth in SEQ ID NOs:67, 66 or 65. In certain further embodiments the heavy chain variable region comprises the amino acid sequence set forth in SEQ ID NO:67 and the antibody further comprises a light chain variable region comprising an amino acid sequence having at least 95% identity to the amino acid sequence set forth in SEQ ID NO:25. In certain other further embodiments the heavy chain variable region comprises the amino acid sequence set forth in SEQ ID NO:66 and the antibody further comprises a light chain variable region comprising an amino acid sequence having at least 95% identity to the amino acid sequence set forth in SEQ ID NO:24. In certain other embodiments the heavy chain variable region comprises the amino acid sequence set forth in SEQ ID NO:65 and the antibody further comprises a light chain variable region comprising an amino acid sequence having at least 95% identity to the amino acid sequence set forth in SEQ ID NO:23. In certain embodiments related to those just described the antibody is selected from a single chain antibody, a ScFv, a univalent antibody lacking a hinge region, and a minibody. In certain other embodiments the antibody is selected from a Fab, a Fab' fragment, a F(ab')$_2$ fragment and a whole antibody. In certain other embodiments the antibody is conjugated to a drug or a toxin.

In certain embodiments the isolated antibody described herein comprises a human IgG Fc domain. In certain embodiments the human IgG Fc domain is modified such that the antibody has enhanced ADCC activity as compared to the antibody having the unmodified human IgG Fc domain.

There is also provided, according to certain embodiments of the invention described herein, an isolated antibody, or an antigen-binding fragment thereof, that binds to human FN14, comprising a light chain variable region comprising any one of the amino acid sequences set forth in SEQ ID NOs:25, 24 or 23. In certain further embodiments the light chain variable region comprises SEQ ID NO:25 and the antibody further comprises a heavy chain variable region comprising an amino acid sequence having at least 95% identity to the amino acid sequence of SEQ ID NO:67. In certain other further embodiments the light chain variable region comprises SEQ ID NO:24 and the antibody further comprises a heavy chain variable region comprising an amino acid sequence having at least 95% identity to the amino acid sequence of SEQ ID NO:66. In certain other further embodiments the light chain variable region comprises SEQ ID NO:23 and the antibody further comprises a heavy chain variable region comprising an amino acid sequence having at least 95% identity to the amino acid sequence of SEQ ID NO:65. In certain other further embodiments the antibody is selected from a single chain antibody, a ScFv, a univalent antibody lacking a hinge region, and a minibody. In certain other further embodiments the antibody is selected from a Fab, a Fab' fragment, a F(ab')$_2$ fragment and a whole antibody.

In certain embodiments the antibody is conjugated to a drug or a toxin. In certain embodiments the antibody comprises a human IgG Fc domain. In certain further embodiments the human IgG Fc domain is modified such that the antibody has enhanced ADCC activity as compared to the antibody having the unmodified human IgG Fc domain.

Turning to another embodiment of the present invention, there is provided a composition comprising a physiologically acceptable carrier and a therapeutically effective amount of the isolated antibody or antigen-binding fragment thereof described above. According to certain other embodiments, there is provided a method for treating a patient having a cancer associated with FN14 expression, comprising administering to the patient the composition that comprises a physiologically acceptable carrier and a therapeutically effective amount of the isolated antibody or antigen-binding fragment thereof described above, thereby treating the cancer associated with FN14 expression. In certain further embodiments the cancer is selected from melanoma, salivary carcinoma, breast cancer, hepatocellular carcinoma, ovarian cancer, cervical cancer, colorectal cancer, non-small cell lung cancer, renal cancer, head and neck cancer, bladder cancer, uterine cancer, stomach cancer, esophageal cancer, pancreatic cancer, and glioblastoma multiforme.

In certain other embodiments there is provided a method for preventing or reducing the likelihood of occurrence of metastasis of a cancer associated with FN14 expression, comprising administering the composition that comprises a physiologically acceptable carrier and a therapeutically effective amount of the isolated antibody or antigen-binding fragment thereof described above to a patient having the cancer, and thereby preventing or reducing the likelihood of occurrence of metastasis of the cancer associated with FN14 expression. In certain embodiments the cancer is selected from melanoma, salivary carcinoma, breast cancer, hepatocellular carcinoma, ovarian cancer, cervical cancer, colorectal cancer, non-small cell lung cancer, renal cancer, head and neck cancer, bladder cancer, uterine cancer, stomach cancer, esophageal cancer, pancreatic cancer, and glioblastoma multiforme.

In certain embodiments according to the present disclosure, there is provided an isolated antibody, or an antigen-binding fragment thereof, that binds to human FN14, comprising: (a) a heavy chain variable region comprising the VHCDR1, VHCDR2 and VHCDR3 amino acid sequences set forth in SEQ ID NOs:77, 81, and 76, respectively, and a light chain variable region comprising the VLCDR1, VLCDR2 and VLCDR3 sequences set forth in SEQ ID NOs:86, 39 and 41, respectively; (b) a heavy chain variable region comprising the VHCDR1, VHCDR2 and VHCDR3 amino acid sequences set forth in SEQ ID NOs:79, 81 and 76, respectively, and a light chain variable region comprising the VLCDR1, VLCDR2 and VLCDR3 amino acid sequences set forth in SEQ ID NOs:86, 39 and 36, respectively; (c) a heavy chain variable region comprising the VHCDR1, VHCDR2 and VHCDR3 amino acid sequences set forth in SEQ ID NOs:79, 81 and 83, respectively, and a light chain variable region comprising the VLCDR1, VLCDR2 and VLCDR3 amino acid sequences set forth in SEQ ID NOs:86, 39 and 41, respectively; or (d) a heavy chain variable region comprising the VHCDR1, VHCDR2 and VHCDR3 amino acid sequences set forth in SEQ ID NOs:79, 82 and 84, respectively, and a light chain variable region comprising the VLCDR1, VLCDR2 and VLCDR3 amino acid sequences set forth in SEQ ID NOs:86, 39 and 41, respectively.

In one embodiment, the heavy chain variable region of the FN14-specific antibodies described herein comprises the VHCDR1, VHCDR2 and VHCDR3 amino acid sequences set forth in SEQ ID NOs:77, 81, and 76, respectively, and the light chain variable region comprises the VLCDR1, VLCDR2 and VLCDR3 amino acid sequences set forth in SEQ ID NOs:86, 39 and 41, respectively. In another embodiment, the heavy chain variable region of the FN14-specific antibodies described herein comprises the VHCDR1, VHCDR2 and VHCDR3 amino acid sequences set forth in SEQ ID NOs:77, 81, and 76, respectively, and the light chain variable region comprises the amino acid sequence set forth in SEQ ID NO:27. In another embodiment, the heavy chain variable region of the FN14-specific antibodies described herein comprises the VHCDR1, VHCDR2 and VHCDR3 amino acid sequences set forth in SEQ ID NOs:77, 81, and 76, respectively, and the light chain variable region comprises the amino acid sequence set forth in SEQ ID NO:26. In another embodiment, the heavy chain variable region comprises the amino acid sequence set forth in SEQ ID NO:68

In one embodiment, the heavy chain variable region of the FN14-specific antibodies described herein comprises the VHCDR1, VHCDR2 and VHCDR3 amino acid sequences set forth in SEQ ID NOs:79, 81 and 76, respectively, and the light chain variable region comprises the VLCDR1, VLCDR2 and VLCDR3 amino acid sequences set forth in SEQ ID NOs:86, 39 and 36, respectively. In another embodiment, the heavy chain variable region comprises the amino acid sequence set forth in SEQ ID NO: 65, and the light chain variable region comprises the VLCDR1, VLCDR2 and VLCDR3 amino acid sequences set forth in SEQ ID NOs:86, 39 and 36, respectively. In yet another embodiment, the heavy chain variable region of the FN14-specific antibodies described herein comprises the VHCDR1, VHCDR2 and VHCDR3 amino acid sequences set forth in SEQ ID NOs:79, 81 and 76, and the light chain variable region comprises the amino acid sequence set forth in SEQ ID NO:23.

In another embodiment, the heavy chain variable region of the FN14-specific antibodies described herein comprises the VHCDR1, VHCDR2 and VHCDR3 amino acid sequences set forth in SEQ ID NOs:79, 81 and 83, respectively, and the light chain variable region comprises the VLCDR1, VLCDR2 and VLCDR3 amino acid sequences set forth in SEQ ID NOs:86, 39 and 41, respectively. In one embodiment, the heavy chain variable region comprises the amino acid sequence set forth in SEQ ID NO:66, and the light chain variable region comprises the VLCDR1, VLCDR2 and VLCDR3 amino acid sequences set forth in SEQ ID NOs:86, 39 and 41. In another embodiment, the heavy chain variable region of the FN14-specific antibodies described herein comprises the VHCDR1, VHCDR2 and VHCDR3 amino acid sequences set forth in SEQ ID NOs:79, 81 and 83, and the light chain variable region comprises the amino acid sequence set forth in SEQ ID NO:24.

In one embodiment, the heavy chain variable region of the FN14-specific antibodies described herein comprises the VHCDR1, VHCDR2 and VHCDR3 amino acid sequences set forth in SEQ ID NOs:79, 82 and 84, respectively, and the light chain variable region comprises the VLCDR1, VLCDR2 and VLCDR3 amino acid sequences set forth in SEQ ID NOs:86, 39 and 41, respectively. In another embodiment, the heavy chain variable region comprises the amino acid sequence set forth in SEQ ID NO:67, and the light chain variable region comprises the VLCDR1, VLCDR2 and VLCDR3 amino acid sequences set forth in SEQ ID NOs:86, 39 and 41. In another embodiment, the heavy chain variable region of the FN14-specific antibodies described herein comprises the VHCDR1, VHCDR2 and VHCDR3 amino acid sequences set forth in SEQ ID NOs:79, 82 and 84, and the light chain variable region comprises the amino acid sequence set forth in SEQ ID NO:25.

In one embodiment of the disclosure, the antibodies described herein are humanized. In this regard, in one embodiment, the light chain variable region of an antibody described herein comprises the amino acid sequence set forth in SEQ ID NO:42 and the heavy chain variable region comprises the amino acid sequence set forth in SEQ ID NO:46.

In certain embodiments, an antibody as described herein may be provided in a particular form, such as, but not limited to, a single chain antibody, a ScFv, a univalent antibody lacking a hinge region, or a minibody. In one particular embodiment, an antibody of the present disclosure is a Fab, a Fab', or a F(ab')$_2$ fragment. In certain embodiments, the antibody is a whole antibody. In certain embodiments, the antibody is conjugated to a drug or a toxin. In this regard, one particular toxin contemplated for use herein is saporin.

In another embodiment, an antibody as described herein comprises a human IgG Fc domain. In this regard, in certain embodiments, the human IgG Fc domain is modified such that the antibody has enhanced ADCC activity as compared to the antibody having the unmodified human IgG Fc domain.

Turning to another embodiment, there is provided an isolated antibody, or an antigen-binding fragment thereof, that binds to human FN14, comprising a heavy chain variable region comprising any one of the amino acid sequences set forth in SEQ ID NOs:65-68. In one embodiment, the heavy chain variable region of an antibody as described herein comprises the amino acid sequence set forth in SEQ ID NO:65 and the antibody further comprises a light chain variable region comprising an amino acid sequence having at least 95% identity to the amino acid sequence set forth in SEQ ID NO:23. In one embodiment, the heavy chain variable region of an antibody as described herein comprises the amino acid sequence set forth in SEQ ID NO:65 and the antibody comprises the light chain variable region that comprises the amino acid sequence set forth in SEQ ID NO:23.

In another embodiment, an antibody as described herein comprises a heavy chain variable region that comprises the amino acid sequence set forth in SEQ ID NO:66 and the antibody further comprises a light chain variable region comprising an amino acid sequence having at least 95% identity to the amino acid sequence set forth in SEQ ID NO:24. In a further embodiment, an antibody as described herein comprises a heavy chain variable region that comprises the amino acid sequence set forth in SEQ ID NO:66 and the light chain variable region comprises the amino acid sequence set forth in SEQ ID NO:24.

In yet another embodiment, an antibody of the present disclosure comprises a heavy chain variable region that comprises the amino acid sequence set forth in SEQ ID NO:67 and the antibody further comprises a light chain variable region comprising an amino acid sequence having at least 95% identity to the amino acid sequence set forth in SEQ ID NO:25; and in certain other related embodiments, the light chain variable region comprises the amino acid sequence set forth in SEQ ID NO:25.

In another embodiment, an antibody of the present disclosure comprises a heavy chain variable region that comprises the amino acid sequence set forth in SEQ ID NO:68, and a light chain variable region comprising an amino acid sequence having at least 95% identity to the amino acid sequence set forth in SEQ ID NO:26. In certain embodiments, the light chain variable region comprises the amino acid sequence set forth in SEQ ID NO:26, or the light chain variable region comprises the amino acid sequence set forth in SEQ ID NO:27.

In another embodiment, an antibody of the present disclosure is selected from a single chain antibody, a ScFv, a univalent antibody lacking a hinge region and a minibody. In further embodiments, the antibody is a Fab, Fab' or F(ab')$_2$ fragment. In certain embodiments, the antibody is a whole antibody. In certain further embodiments, the antibodies of the present disclosure are conjugated to a drug or a toxin, such as saporin.

In another embodiment there is provided an isolated antibody, or an antigen-binding fragment thereof, that binds to human FN14, comprising a light chain variable region comprising any one of the amino acid sequences set forth in SEQ ID NOs:23-27. In one embodiment, the antibody that binds to human FN14 comprises a light chain variable region that comprises SEQ ID NO:23 and further comprises a heavy chain variable region comprising an amino acid sequence having at least 95% identity to the amino acid sequence of SEQ ID NO:65.

In another embodiment, the antibody that binds to human FN14 comprises a light chain variable region that comprises SEQ ID NO:24 and further comprises a heavy chain variable region comprising an amino acid sequence having at least 95% identity to the amino acid sequence of SEQ ID NO:66.

In another embodiment, the antibody that binds to human FN14 comprises a light chain variable region that comprises SEQ ID NO:25 and further comprises a heavy chain variable region comprising an amino acid sequence having at least 95% identity to the amino acid sequence of SEQ ID NO:67.

In yet another embodiment, the antibody that binds to human FN14 comprises a light chain variable region that comprises SEQ ID NO:26 and further comprises a heavy chain variable region comprising an amino acid sequence having at least 95% identity to the amino acid sequence of SEQ ID NO:68.

In another embodiment, the antibody that binds to human FN14 comprises a light chain variable region that comprises SEQ ID NO:27 and further comprises a heavy chain variable region comprising an amino acid sequence having at least 95% identity to the amino acid sequence of SEQ ID NO:68.

According to certain other embodiments, the present disclosure provides a composition comprising a physiologically acceptable carrier and a therapeutically effective amount of an isolated antibody that binds FN14, or an antigen-binding fragment thereof, as described herein.

In other embodiments, the present disclosure provides methods for treating a patient having a cancer associated with FN14 expression, comprising administering to the patient such a composition comprising a physiologically acceptable carrier and a therapeutically effective amount of an isolated antibody that binds FN14, or an antigen-binding fragment thereof, as described herein, thereby treating the cancer associated with FN14 expression.

In another embodiment there is provided a method for preventing or reducing the likelihood of occurrence of metastasis of a cancer associated with FN14 expression, comprising administering, to a patient having the cancer, a composition comprising a physiologically acceptable carrier and a therapeutically effective amount of an isolated antibody that binds FN14, or an antigen-binding fragment thereof, as described herein, and thereby preventing or reducing the likelihood of occurrence of metastasis of the cancer associated with FN14 expression. In certain embodiments, a cancer that can be treated with the antibodies as described herein includes but is not limited to one or more of melanoma, salivary carcinoma, breast cancer, hepatocellular carcinoma, ovarian cancer, cervical cancer, colorectal cancer, non-small cell lung cancer, renal cancer, head and neck cancer, bladder cancer, uterine cancer, stomach cancer, esophageal cancer, pancreatic cancer, and glioblastoma multiforme.

These and other aspects and embodiments of the herein described invention will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet are incorporated herein by reference in their entirety, as if each was incorporated individually. Aspects and embodiments of the invention can be modified, if necessary, to employ concepts of the various patents, applications and publications to provide yet further embodiments.

BRIEF DESCRIPTION OF THE DRAWINGS

FIG. 1. Clonal diversification rate accelerated in DTLacO cells.

FIG. 2. High affinity anti-FN14 mAb selected from DTLacO cells.

FIG. 3 shows sequence alignments of FN14-specific antibody VH (FIG. 3A) and VL (FIG. 3B) regions. The CDR regions are indicated by underlining. Heavy Chain VDJ sequences: HP1VDJ set forth in SEQ ID NO:64; FS10 set forth in SEQ ID NO:65; PS4 set forth in SEQ ID NO:68; FS17 set forth in SEQ ID NO:66; FS24 set forth in SEQ ID NO:67. Light Chain VJ sequences: VJDT40 set forth in SEQ ID NO:22; FS10 set forth in SEQ ID NO:23; FS17 set forth in SEQ ID NO:24; FS24 set forth in SEQ ID NO:25; PS4A set forth in SEQ ID NO:27; PS4B set forth in SEQ ID NO:26.

FIG. 6 shows sequence alignments of the humanized PS4 light and heavy chain variable regions (SEQ ID NOs: 56 and 58) with the corresponding chicken precursor sequences (SEQ ID NO: 26 and 68) and the human Vλ and VH subgroup III consensus sequences with CDRs indicated as dashes (SEQ ID NOs: 87 and 88). Sequence numbering is according to Kabat (Kabat, E. A., et al., 1991. Sequences of Proteins of Immunological Interest, 5th ed., Public Health Service, National Institutes of Health, Bethesda, Md.). CDRs are underlined. Asterisks indicate a gap in the alignment. Vernier zone positions in which the chicken residue was retained in the framework sequence are denoted by a double underline. hPS4H and hPS4L indicate humanized versions of PS4 VH and VL, respectively. HIII: human VH subgroup III consensus sequence. LIII: human Vλ subgroup III consensus sequence.

FIG. 8 shows sequence alignments of the humanized FS24 heavy and light chain variable region amino acid sequences (SEQ ID NOs: 90 and 91, respectively) with the corresponding chicken precursor sequences (SEQ ID NOs: 67 and 25) and the human Vλ and VH subgroup III consensus sequences with CDRs shown with dashes (SEQ ID NOs: 87 and 88). Sequence numbering is according to Kabat 1991, supra. CDRs are underlined. Asterisks indicate a gap in the alignment. Vernier zone positions in which the chicken residue was retained in the framework sequence are denoted by a double underline. hFS24H and hFS24L indicate humanized versions of FS24 VH and VL, respectively. HIII: human VH subgroup III consensus sequence. LIII: human Vλ subgroup III consensus sequence.

FIG. 10 shows that the FS24-toxin conjugate killed cancer cells.

BRIEF DESCRIPTION OF THE SEQUENCES

Figure 1A:
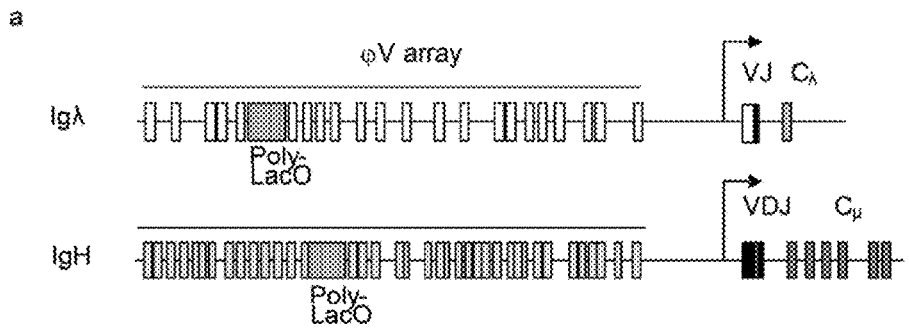
FIG. 1A is a diagram of rearranged and expressed Igλ (above) and IgH (below) loci with PolyLacO inserted within the ψV arrays. Arrows denote promoters.

SEQ ID NO:1: amino acid sequence of Parental DT40 HP1VH (parental DT40 population)
SEQ ID NO:2: amino acid sequence of FS10 VH
SEQ ID NO:3: amino acid sequence of FS17 VH
SEQ ID NO:4: amino acid sequence of FS24 VH
SEQ ID NO:5: amino acid sequence of PS4 VH
SEQ ID NO:6: polynucleotide sequence encoding HP1VH (parental DT40 population)
SEQ ID NO:7: polynucleotide sequence encoding FS10 VH
SEQ ID NO:8: polynucleotide sequence encoding FS17 VH
SEQ ID NO:9: polynucleotide sequence encoding FS24 VH
SEQ ID NO:10: polynucleotide sequence encoding PS4 VH
SEQ ID NO:11: amino acid sequence of VHCDR1 Parental DT40 HP1
SEQ ID NO:12: amino acid sequence of VHCDR2 Parental DT40 HP1
SEQ ID NO:13: amino acid sequence of VHCDR3 Parental DT40 HP1, FS10 and PS4
SEQ ID NO:14: amino acid sequence of VHCDR1 of PS4
SEQ ID NO:15: amino acid sequence of VHCDR1 of PS4 with downstream framework extension
SEQ ID NO:16: amino acid sequence of VHCDR1 of FS10, FS17, FS24
SEQ ID NO:17: amino acid sequence of VHCDR1 of FS10, FS17, FS24 with downstream framework extension
SEQ ID NO:18: amino acid sequence of VHCDR2 of PS4, FS10 and FS17
SEQ ID NO:19: amino acid sequence of VHCDR2 of FS24
SEQ ID NO:20: amino acid sequence of VHCDR3 of FS17
SEQ ID NO:21: amino acid sequence of VHCDR3 of FS24
SEQ ID NO:22: amino acid sequence of VJ (VL) DT40 (parental DT40 population)
SEQ ID NO:23: amino acid sequence of FS10 VL
SEQ ID NO:24: amino acid sequence of FS17 VL
SEQ ID NO:25: amino acid sequence of FS24 VL
SEQ ID NO:26: amino acid sequence of PS4B VL
SEQ ID NO:27: amino acid sequence of PS4A VL
SEQ ID NO:28: polynucleotide sequence encoding VJ (VL) DT40 (parental DT40 population)
SEQ ID NO:29: polynucleotide sequence encoding FS10 VL
SEQ ID NO:30: polynucleotide sequence encoding FS17 VL
SEQ ID NO:31: polynucleotide sequence encoding FS24 VL
SEQ ID NO:32: polynucleotide sequence encoding PS4B VL
SEQ ID NO:33: polynucleotide sequence encoding PS4A VL
SEQ ID NO:34: amino acid sequence of VLCDR1 of parental DT40
SEQ ID NO:35: amino acid sequence of VLCDR2 of parental DT40
SEQ ID NO:36: amino acid sequence of VLCDR3 of parental DT40 and FS10
SEQ ID NO:37: amino acid sequence of VLCDR1 of PS4A, PS4B, FS10, FS17, FS24
SEQ ID NO:38: amino acid sequence of VLCDR1 with upstream framework of PS4A, PS4B, FS10, FS17, FS24
SEQ ID NO:39: amino acid sequence of VLCDR2 of PS4A, PS4B, FS10, FS17, FS24
SEQ ID NO:40: amino acid sequence of VLCDR2 of PS4A, FS17, FS24 with upstream framework
SEQ ID NO:41: amino acid sequence of VLCDR3 of PS4A, PS4B, FS17, FS24
SEQ ID NO:42: amino acid sequence of humanized PS4 light chain, version L.9 with the human lambda light chain constant region SEQ ID NO:43: polynucleotide sequence encoding humanized PS4 light chain, version L.9 (including signal sequence)

SEQ ID NO:44: amino acid sequence of humanized PS4 light chain, version L.18

SEQ ID NO:45: polynucleotide sequence encoding humanized PS4 light chain, version L.18 (including signal sequence)

SEQ ID NO:46: amino acid sequence of humanized PS4 heavy chain, version H.1 with the human IgG1 constant region SEQ ID NO:47: polynucleotide sequence encoding humanized PS4 heavy chain, version H.1 (including signal sequence)

SEQ ID NOs:48-50 are illustrative linker sequences.

SEQ ID NO:51: polynucleotide sequence encoding human IgG1 constant region (CH1-hinge-CH2-CH3)

SEQ ID NO:52: amino acid sequence for human IgG1 constant region ($CH_1$-hinge-$CH_2$—$CH_3$)

SEQ ID NO:53: polynucleotide sequence encoding human lambda light chain constant region SEQ ID NO:54: amino acid sequence for human lambda light chain constant region SEQ ID NO:55: amino acid sequence of VLCDR2 of FS10 with upstream framework SEQ ID NO:56: amino acid sequence of humanized PS4 light chain variable region, version L.9

SEQ ID NO:57: amino acid sequence of human Vλ subgroup III consensus sequence with PS4 VL CDRs SEQ ID NO:58: amino acid sequence of humanized PS4 heavy chain variable region, version H.1

SEQ ID NO:59: amino acid sequence of human VH subgroup III consensus sequence with PS4 VH CDRs SEQ ID NO:60: amino acid sequence of the humanized FS24 light chain with the human lambda light chain constant region SEQ ID NO:61: nucleic acid sequence encoding the humanized FS24 light chain sequence set forth in SEQ ID NO:60

SEQ ID NO:62: amino acid sequence of the humanized FS24 heavy chain with human IgG1 constant region SEQ ID NO:63: nucleic acid sequence encoding the humanized FS24 heavy chain sequence set forth in SEQ ID NO:62

SEQ ID NO:64: amino acid sequence of Parental DT40 HP1VH (parental DT40 population) with amino acid "A" added at first position SEQ ID NO:65: amino acid sequence of FS10 VH with amino acid "A" added at first position SEQ ID NO:66: amino acid sequence of FS17 VH with amino acid "A" added at first position SEQ ID NO:67: amino acid sequence of FS24 VH with amino acid "A" added at first position SEQ ID NO:68: amino acid sequence of PS4 VH with amino acid "A" added at first position SEQ ID NO:69: polynucleotide sequence encoding HP1VH (parental DT40 population) amino acid sequence of SEQ ID NO:64

SEQ ID NO:70: polynucleotide sequence encoding FS10 VH amino acid sequence of SEQ ID NO:65

SEQ ID NO:71: polynucleotide sequence encoding FS17 VH amino acid sequence of SEQ ID NO:66

SEQ ID NO:72: polynucleotide sequence encoding FS24 VH amino acid sequence of SEQ ID NO:67

SEQ ID NO:73: polynucleotide sequence encoding PS4 VH amino acid sequence of SEQ ID NO:68

SEQ ID NO:74: amino acid sequence of VHCDR1 Parental DT40 HP1 (Kabat definition)

SEQ ID NO:75: amino acid sequence of VHCDR2 Parental DT40 HP1 (Kabat definition)

SEQ ID NO:76: amino acid sequence of VHCDR3 Parental DT40 HP1, FS10 and PS4 (Kabat definition)

SEQ ID NO:77: amino acid sequence of VHCDR1 of PS4 (Kabat definition)

SEQ ID NO:78: amino acid sequence of VHCDR1 of PS4 (Kabat definition) with downstream framework extension SEQ ID NO:79: amino acid sequence of VHCDR1 of FS10, FS17, FS24 (Kabat definition)

SEQ ID NO:80: amino acid sequence of VHCDR1 of FS10, FS17, FS24 (Kabat definition) with downstream framework extension SEQ ID NO:81: amino acid sequence of VHCDR2 of PS4, FS10 and FS17 (Kabat definition)

SEQ ID NO:82: amino acid sequence of VHCDR2 of FS24 (Kabat definition)

SEQ ID NO:83: amino acid sequence of VHCDR3 of FS17 (Kabat definition)

SEQ ID NO:84: amino acid sequence of VHCDR3 of FS24 (Kabat definition)

SEQ ID NO:85: amino acid sequence of VLCDR1 of parental DT40 (Kabat definition)

SEQ ID NO:86: amino acid sequence of VLCDR1 of PS4A, PS4B, FS10, FS17, FS24 (Kabat definition)

SEQ ID NO:87: amino acid sequence of human Vλ subgroup III consensus sequence with CDR amino acids denoted by "X"

SEQ ID NO:88: amino acid sequence of human VH subgroup III consensus sequence with CDR amino acids denoted by "X"

SEQ ID NO:89: a human FN14 amino acid sequence

SEQ ID NO:90 is the amino acid sequence of the humanized FS24 heavy chain variable region.

SEQ ID NO:91 is the amino acid sequence of the humanized FS24 light chain variable region.

SEQ ID NO:92 is a consensus sequence taken from FIG. 3 for VHCDR2 regions (Kabat definition) of FS17 (SEQ ID NO:81), FS10 (SEQ ID NO:81) and FS24 (SEQ ID NO:82).

SEQ ID NO:93 is a consensus sequence taken from FIG. 3 for VHCDR3 regions (Kabat definition) of FS17 (SEQ ID NO:83), FS10 (SEQ ID NO:76) and FS24 (SEQ ID NO:84).

SEQ ID NO:94 is a consensus sequence taken from FIG. 3 for VLCDR3 regions (Kabat definition) of FS17 (SEQ ID NO:41), FS10 (SEQ ID NO:36) and FS24 (SEQ ID NO:41).

DETAILED DESCRIPTION

Antibodies and Antigen-Binding Fragments Thereof

Embodiments of the present invention relate to antibodies that bind to FN14, the TWEAK receptor. In particular, the antibodies described herein specifically bind to FN14 with unexpectedly high affinity, mediate specific cellular toxicity and have therapeutic utility for the treatment of diseases associated with aberrant expression (in particular overexpression) of FN14. An illustrative amino acid sequence of human FN14 is set forth in SEQ ID NO:89. Amino acid sequences of illustrative antibodies, or antigen-binding fragments, or complementarity determining regions (CDRs) thereof, are set forth in SEQ ID NOs:2-5, 13-21, 23-27, 36-42, 44, 46, 55-60, 62, 65-68, 76-84, 86, and 90-91.

An "antibody" is an immunoglobulin molecule capable of specific binding to a target, such as a carbohydrate, polynucleotide, lipid, polypeptide, etc., through at least one epitope recognition site, located in the variable region (also referred to herein as the variable domain) of the immunoglobulin molecule. As used herein, the term encompasses not only intact polyclonal or monoclonal antibodies, but also fragments thereof (such as dAb, Fab, Fab', F(ab')$_2$, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity. "Diabodies", multivalent or multispecific fragments constructed by gene fusion (WO94/13804; P. Holliger et al, Proc. Natl. Acad. Sci. USA 90 6444-6448, 1993) are also a particular form of antibody contemplated herein. Minibodies comprising a scFv joined to a CH3 domain are also included herein (S. Hu et al, Cancer Res., 56, 3055-3061, 1996). See e.g., Ward, E. S. et al., Nature 341, 544-546 (1989); Bird et al, Science, 242, 423-426, 1988; Huston et al, PNAS USA, 85, 5879-5883, 1988); PCT/US92/09965; WO94/13804; P. Holliger et al, Proc. Natl. Acad. Sci. USA 90 6444-6448, 1993; Y. Reiter et al, Nature Biotech, 14, 1239-1245, 1996; S. Hu et al, Cancer Res., 56, 3055-3061, 1996.

The term "antigen-binding fragment" as used herein refers to a polypeptide fragment that contains at least one CDR of an immunoglobulin heavy and/or light chains that binds to the antigen of interest, in particular to the FN14 receptor. In this regard, an antigen-binding fragment of the herein described antibodies may comprise 1, 2, 3, 4, 5, or all 6 CDRs of a VH and VL sequence set forth herein from antibodies that bind FN14. An antigen-binding fragment of the herein described FN14-specific antibodies is capable of binding to FN14. In certain embodiments, an antigen-binding fragment or an antibody comprising an antigen-binding fragment, mediates killing of a target cell expressing FN14. In further embodiments, binding of an antigen-binding fragment prevents or inhibits binding of the FN14 ligand to its receptor, interrupting the biological response resulting from ligand binding to the receptor. In certain embodiments, the antigen-binding fragment binds specifically to and/or inhibits or modulates the biological activity of human FN14.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. In certain embodiments, an antibody is said to specifically bind an antigen when it preferentially recognizes its target antigen in a complex mixture of proteins and/or macromolecules. An antibody is said to specifically bind an antigen when the equilibrium dissociation constant is $\leq 10^{-7}$ or $10^{-8}$ M. In some embodiments, the equilibrium dissociation constant may be $\leq 10^{-9}$ M or $\leq 10^{-10}$ M.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091-4096.

In certain embodiments, single chain Fv or scFV antibodies are contemplated. For example, Kappa bodies (III et al., Prot. Eng. 10: 949-57 (1997); minibodies (Martin et al., EMBO J. 13: 5305-9 (1994); diabodies (Holliger et al., PNAS 90: 6444-8 (1993); or Janusins (Traunecker et al., EMBO J. 10: 3655-59 (1991) and Traunecker et al. Int. J. Cancer Suppl. 7: 51-52 (1992), may be prepared using standard molecular biology techniques following the teachings of the present application with regard to selecting antibodies having the desired specificity. In still other embodiments, bispecific or chimeric antibodies may be made that encompass the ligands of the present disclosure. For example, a chimeric antibody may comprise CDRs and framework regions from different antibodies, while bispecific antibodies may be generated that bind specifically to FN14 through one binding domain and to a second molecule through a second binding domain. These antibodies may be produced through recombinant molecular biological techniques or may be physically conjugated together.

A single chain Fv (sFv) polypeptide is a covalently linked $V_H$::$V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

A dAb fragment of an antibody consists of a VH domain (Ward, E. S. et al., Nature 341, 544-546 (1989)).

In certain embodiments, an antibody as herein disclosed (e.g., an FN14-specific antibody) is in the form of a diabody. Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Holliger, P. and Winter G. Current Opinion Biotechnol. 4, 446-449 (1993)), e.g. prepared chemically or from hybrid hybridomas, or may be any of the bispecific antibody fragments mentioned above. Diabodies and scFv can be constructed without an Fc region, using only variable regions, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (J. B. B. Ridgeway et al, *Protein Eng.*, 9, 616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US20090226421). This proprietary antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The UniBody® is about half the size of a regular IgG4 antibody. This small size can be a great benefit when treating some forms of cancer, allowing for better distribution of the molecule over larger solid tumors and potentially increasing efficacy.

In certain embodiments, the antibodies of the present disclosure may take the form of a nanobody. Nanobodies are encoded by single genes and are efficiently produced in almost all prokaryotic and eukaryotic hosts e.g. *E. coli* (see e.g. U.S. Pat. No. 6,765,087), moulds (for example *Aspergillus* or *Trichoderma*) and yeast (for example *Saccharomyces, Kluyvermyces, Hansenula* or *Pichia* (see e.g. U.S. Pat. No. 6,838,254). The production process is scalable and multi-kilogram quantities of nanobodies have been produced. Nanobodies may be formulated as a ready-to-use solution having a long shelf life. The Nanoclone method (see eg. WO 06/079372) is a proprietary method for generating Nanobodies against a desired target, based on automated high-throughput selection of B-cells.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable regions may be determined by reference to Kabat, E. A. et al, Sequences of Proteins of Immunological Interest. 4th Edition. US Department of Health and Human Services. 1987, and updates thereof, now available on the Internet (immuno.bme.nwu.edu).

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody".

"Humanized" antibodies refer to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable regions fused onto constant domains or only the CDRs grafted onto appropriate framework regions in the variable regions. Epitope binding sites may be wild type or modified by one or more amino acid substitutions. This eliminates the constant region as an immunogen in human individuals, but the possibility of an immune response to the foreign variable region remains (LoBuglio, A.

F. et al., (1989) *Proc Natl Acad Sci USA* 86:4220-4224; Queen et al., *PNAS* (1988) 86:10029-10033; Riechmann et al., *Nature* (1988) 332:323-327). Illustrative humanized antibodies according to certain embodiments of the present invention comprise the humanized sequences provided in SEQ ID NOs:42-47 and 60-63.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato, K., et al., (1993) *Cancer Res* 53:851-856. Riechmann, L., et al., (1988) *Nature* 332: 323-327; Verhoeyen, M., et al., (1988) *Science* 239:1534-1536; Kettleborough, C. A., et al., (1991) *Protein Engineering* 4:773-3783; Maeda, H., et al., (1991) *Human Antibodies Hybridoma* 2:124-134; Gorman, S. D., et al., (1991) *Proc Natl Acad Sci USA* 88:4181-4185; Tempest, P. R., et al., (1991) *Bio/Technology* 9:266-271; Co, M. S., et al., (1991) *Proc Natl Acad Sci USA* 88:2869-2873; Carter, P., et al., (1992) *Proc Natl Acad Sci USA* 89:4285-4289; and Co, M. S. et al., (1992) *J Immunol* 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies of the present disclosure may be chimeric antibodies. In this regard, a chimeric antibody is comprised of an antigen-binding fragment of an anti-FN14 antibody operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the anti-FN14 antigen-binding fragment of a chimeric antibody may comprise only one or more of the CDRs of the antibodies described herein (e.g., 1, 2, 3, 4, 5, or 6 CDRs of the antibodies described herein), or may comprise an entire variable region (VL, VH or both).

In certain embodiments, an FN14-binding antibody comprises one or more of the CDRs of the antibodies described herein. In this regard, it has been shown in some cases that the transfer of only the VHCDR3 of an antibody can be done while still retaining desired specific binding (Barbas et al., *PNAS* (1995) 92: 2529-2533). See also, McLane et al., *PNAS* (1995) 92:5214-5218, Barbas et al., *J. Am. Chem. Soc.* (1994) 116:2161-2162.

Marks et al (*Bio/Technology,* 1992, 10:779-783) describe methods of producing repertoires of antibody variable regions in which consensus primers directed at or adjacent to the 5' end of the variable region area are used in conjunction with consensus primers to the third framework region of human VH genes to provide a repertoire of VH variable regions lacking a CDR3. Marks et al further describe how this repertoire may be combined with a CDR3 of a particular antibody. Using analogous techniques, the CDR3-derived sequences of the presently described antibodies may be shuffled with repertoires of VH or VL domains lacking a CDR3, and the shuffled complete VH or VL domains combined with a cognate VL or VH domain to provide an antibody or antigen-binding fragment thereof that binds FN14. The repertoire may then be displayed in a suitable host system such as the phage display system of WO92/01047 so that suitable antibodies or antigen-binding fragments thereof may be selected. A repertoire may consist of at least from about $10^4$ individual members and upwards by several orders of magnitude, for example, to about from $10^6$ to $10^8$ or $10^{10}$ or more members. Analogous shuffling or combinatorial techniques are also disclosed by Stemmer (Nature, 1994, 370: 389-391), who describes the technique in relation to a β-lactamase gene but observes that the approach may be used for the generation of antibodies.

A further alternative is to generate novel VH or VL regions carrying one or more CDR-derived sequences of the herein described invention embodiments using random mutagenesis of one or more selected VH and/or VL genes to generate mutations within the entire variable region. Such a technique is described by Gram et al (1992, Proc. Natl. Acad. Sci., USA, 89:3576-3580), who used error-prone PCR. Another method which may be used is to direct mutagenesis to CDR regions of VH or VL genes. Such techniques are disclosed by Barbas et al, (1994, Proc. Natl. Acad. Sci., USA, 91:3809-3813) and Schier et al (1996, J. Mol. Biol. 263:551-567).

In certain embodiments, a specific VH and/or VL of the antibodies described herein may be used to screen a library of the complementary variable region to identify antibodies with desirable properties, such as increased affinity for FN14. Such methods are described, for example, in Portolano et al., J. Immunol. (1993) 150:880-887; Clarkson et al., Nature (1991) 352:624-628.

Other methods may also be used to mix and match CDRs to identify antibodies having desired binding activity, such as binding to FN14. For example: Klimka et al., *British Journal of Cancer* (2000) 83: 252-260, describe a screening process using a mouse VL and a human VH library with CDR3 and FR4 retained from the mouse VH. After obtaining antibodies, the VH was screened against a human VL library to obtain antibodies that bound antigen. Beiboer et al., J. Mol. Biol. (2000) 296:833-849 describe a screening process using an entire mouse heavy chain and a human light chain library. After obtaining antibodies, one VL was combined with a human VH library with the CDR3 of the mouse retained. Antibodies capable of binding antigen were obtained. Rader et al., PNAS (1998) 95:8910-8915 describe a process similar to Beiboer et al above.

These just-described techniques are, in and of themselves, known as such in the art. The skilled person will, however, be able to use such techniques to obtain antibodies or antigen-binding fragments thereof according to several embodiments of the invention described herein, using routine methodology in the art.

Also disclosed herein is a method for obtaining an antibody antigen binding domain specific for FN14 antigen, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a specific binding member or an antibody antigen binding domain specific for FN14 and optionally with one or more of preferred properties, preferably ability to mediate cytotoxicity of cells expressing FN14. Said VL domains may have an amino acid sequence which is substantially as set out herein. An analogous method may be employed in which one or more sequence variants of a VL domain disclosed herein are combined with one or more VH domains.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an FN14 epitope is an antibody that binds one FN14 epitope with greater affinity, avidity, more readily, and/or with greater duration than it binds to other FN14 epitopes or non-FN14 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439-473.

The term "immunologically active", with reference to an epitope being or "remaining immunologically active", refers to the ability of an antibody (e.g., anti-FN14 antibody) to bind to the epitope under different conditions, for example, after the epitope has been subjected to reducing and denaturing conditions.

An antibody or antigen-binding fragment thereof according to certain preferred embodiments of the present application may be one that competes for binding to FN14 with any antibody described herein which both (i) specifically binds to the antigen and (ii) comprises a VH and/or VL domain disclosed herein, or comprises a VH CDR3 disclosed herein, or a variant of any of these. Competition between binding members may be assayed easily in vitro, for example using ELISA and/or by tagging a specific reporter molecule to one binding member which can be detected in the presence of other untagged binding member(s), to enable identification of specific binding members which bind the same epitope or an overlapping epitope.

Thus, there is presently provided a specific antibody or antigen-binding fragment thereof, comprising a human antibody antigen-binding site which competes with an antibody described herein that binds to FN14, such as PS4 (A or B), FS17, or FS24, for binding to FN14.

The constant regions of immunoglobulins show less sequence diversity than the variable regions, and are responsible for binding a number of natural proteins to elicit important biochemical events. In humans there are five different classes of antibodies including IgA (which includes subclasses IgA1 and IgA2), IgD, IgE, IgG (which includes subclasses IgG1, IgG2, IgG3, and IgG4), and IgM. The distinguishing features between these antibody classes are their constant regions, although subtler differences may exist in the V region.

The Fc region of an antibody interacts with a number of Fc receptors and ligands, imparting an array of important functional capabilities referred to as effector functions. For IgG the Fc region comprises Ig domains CH2 and CH3 and the N-terminal hinge leading into CH2. An important family of Fc receptors for the IgG class are the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack.

The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). All FcγRs bind the same region on Fc, at the N-terminal end of the Cg2 (CH2) domain and the preceding hinge. This interaction is well characterized structurally (Sondermann et al., 2001, J Mol Biol 309:737-749), and several structures of the human Fc bound to the extracellular domain of human FcγRIIIb have been solved (pdb accession code 1E4K)(Sondermann et al., 2000, Nature 406:267-273.) (pdb accession codes 1I5 and 1 IIX)(Radaev et al., 2001, J Biol Chem 276:16469-16477.)

The different IgG subclasses have different affinities for the FcγRs, with IgG1 and IgG3 typically binding substantially better to the receptors than IgG2 and IgG4 (Jefferis et al., 2002, Immunol Lett 82:57-65). All FcγRs bind the same region on IgG Fc, yet with different affinities: the high affinity binder FcγRI has a Kd for IgG1 of $10^{-8}$ $M^{-1}$, whereas the low affinity receptors FcγRII and FcγRIII generally bind at $10^{-6}$ and $10^{-6}$ respectively. The extracellular domains of FcγRIIIa and FcγRIIIb are 96% identical, however FcγRIIIb does not have a intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. The receptors also differ in expression pattern and levels on different immune cells. Yet another level of complexity is the existence of a number of FcγR polymorphisms in the human proteome. A particularly relevant polymorphism with clinical significance is V158/F158 FcγRIIIa. Human IgG1 binds with greater affinity to the V158 allotype than to the F158 allotype. This difference in affinity, and presumably its effect on ADCC and/or ADCP, has been shown to be a significant determinant of the efficacy of the anti-CD20 antibody rituximab (Rituxan®, a registered trademark of IDEC Pharmaceuticals Corporation). Patients with the V158 allotype respond favorably to rituximab treatment; however, patients with the lower affinity F158 allotype respond poorly (Cartron et al., 2002, Blood 99:754-758). Approximately 10-20% of humans are V158N158 homozygous, 45% are V158/F158 heterozygous, and 35-45% of humans are F158/F158 homozygous (Lehrnbecher et al., 1999, Blood 94:4220-4232; Cartron et al., 2002, Blood 99:754-758). Thus 80-90% of humans are poor responders, that is they have at least one allele of the F158 FcγRIIIa.

The Fc region is also involved in activation of the complement cascade. In the classical complement pathway, C1 binds with its C1q subunits to Fc fragments of IgG or IgM, which has formed a complex with antigen(s). In certain embodiments of the invention, modifications to the Fc region comprise modifications that alter (either enhance or decrease) the ability of a herein described FN14-specific antibody to activate the complement system (see e.g., U.S. Pat. No. 7,740,847). To assess complement activation, a complement-dependent cytotoxicity (CDC) assay may be performed (See, e.g., Gazzano-Santoro et al., J. Immunol. Methods, 202:163 (1996)). For example, various concentrations of the (Fc) variant polypeptide and human complement may be diluted with buffer. Mixtures of (Fc) variant antibodies, diluted human complement and cells expressing the antigen (FN14) may be added to a flat bottom tissue culture 96 well plate and allowed to incubate for 2 hours at 37° C. and 5% $CO_2$ to facilitate complement mediated cell lysis. Fifty microliters of alamar blue (Accumed International) may then be added to each well and incubated overnight at 37° C. The absorbance may be measured using a 96-well fluorimeter with excitation at 530 nm and emission at 590 nm. The results may be expressed in relative fluorescence units (RFU). The sample concentrations may be computed from a standard curve and the percent activity as compared to nonvariant antibody may be reported for the variant antibody of interest.

Thus in certain embodiments, the present invention provides anti-FN14 antibodies having a modified Fc region with altered functional properties, such as enhanced ADCC, ADCP, CDC, or enhanced binding affinity for a specific FcγR. Illustrative modifications of the Fc region include those described in, e.g., Stavenhagen et al., 2007 Cancer Res. 67:8882. Other modified Fc regions contemplated herein are described, for example, in issued U.S. Pat. Nos. 7,317,091; 7,657,380; 7,662,925; 6,538,124; 6,528,624; 7,297,775; 7,364,731; Published U.S. Applications US2009092599; US20080131435; US20080138344; and published International Applications WO2006/105338; WO2004/063351; WO2006/088494; WO2007/024249.

The desired functional properties of anti-FN14 antibodies may be assessed using a variety of methods known to the skilled person, including but not limited to ADCC assays (see Example section), ADCP assays, affinity/binding assays (for example, surface plasmon resonance, competitive inhibition assays); cytotoxicity assays, cell viability assays (e.g., using dye exclusion such as Trypan Blue, propidium iodide, etc), cancer cell and/or tumor growth inhibition using in vitro or in vivo models (e.g., cell proliferation and/or colony formation assays; anchorage-dependent proliferation assays; standard human tumor xenograft models) (see, e.g., Culp P A, et al., Clin. Cancer Res. 16(2):497-508). Other assays may test the ability of antibodies described herein to block normal FN14-mediated responses, such as cell proliferation, differentiation, and in certain cell types, immunoregulatory functions (Bradley J R and Pober J S Oncogene 2001; 20:6482-91). Such assays may be performed using well-established protocols known to the skilled person (see e.g., Current Protocols in Molecular Biology (Greene Publ. Assoc. Inc. & John Wiley & Sons, Inc., NY, N.Y.); Current Protocols in Immunology (Edited by: John E. Coligan, Ada M. Kruisbeek, David H. Margulies, Ethan M. Shevach, Warren Strober 2001 John Wiley & Sons, NY, N.Y.); or commercially available kits.

The present invention further provides in certain embodiments an isolated nucleic acid encoding an antibody or antigen-binding fragment thereof as described herein, for instance, a nucleic acid which codes for a CDR or VH or VL domain. Nucleic acids include DNA and RNA. These and related embodiments may include polynucleotides encoding antibodies that bind FN14 as described herein. The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers. In certain embodiments, the nucleotides comprising the polynucleotide can be ribonucleotides or deoxyribonucleotides or a modified form of either type of nucleotide. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, Nucl. Acids Res., 14:9081; Stec et al., 1984, J. Am. Chem. Soc., 106:6077; Stein et al., 1988, Nucl. Acids Res., 16:3209; Zon et al., 1991, Anti-Cancer Drug Design, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al, U.S. Pat. No. 5,151,510; Uhlmann and Peyman, 1990, Chemical Reviews, 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell. The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

As will be understood by those skilled in the art, polynucleotides may include genomic sequences, extra-genomic and plasmid-encoded sequences and smaller engineered gene segments that express, or may be adapted to express, proteins, polypeptides, peptides and the like. Such segments may be naturally isolated, or modified synthetically by the skilled person.

As will be also recognized by the skilled artisan, polynucleotides may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide according to the present disclosure, and a polynucleotide may, but need not, be linked to other molecules and/or support materials. Polynucleotides may comprise a native sequence or may comprise a sequence that encodes a variant or derivative of such a sequence.

Therefore, according to these and related embodiments, polynucleotides are provided that comprise some or all of a polynucleotide sequence set forth in any one of SEQ ID NOs:6-10, 28-33, 43, 45, 47, 51, 53, 61, 63 and 69-73, complements of a polynucleotide sequence set forth in any one of SEQ ID NOs: 6-10, 28-33, 43, 45, 47, 51, 53, 61, 63 and 69-73, and degenerate variants of a polynucleotide sequence set forth in any one of SEQ ID NOs: 6-10, 28-33, 43, 45, 47, 51, 53, 61, 63 and 69-73. In certain preferred embodiments, the polynucleotide sequences set forth herein encode antibodies, or antigen-binding fragments thereof, which bind the FN14, as described elsewhere herein.

In other related embodiments, polynucleotide variants may have substantial identity to the sequences disclosed herein in SEQ ID NOs: 6-10, 28-33, 43, 45, 47, 51, 53, 61, 63 and 69-73, for example those comprising at least 70% sequence identity, preferably at least 75%, 80%, 85%, 90%, 95%, 96%, 97%, 98%, or 99% or higher, sequence identity compared to a reference polynucleotide sequence such as the sequences disclosed herein, using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the binding affinity of the antibody encoded by the variant polynucleotide is not substantially diminished relative to an antibody encoded by a polynucleotide sequence specifically set forth herein.

In certain other related embodiments, polynucleotide fragments may comprise or consist essentially of various lengths of contiguous stretches of sequence identical to or complementary to one or more of the sequences disclosed herein. For example, polynucleotides are provided that comprise or consist essentially of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110, 120, 130, 140, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of the disclosed sequence or at both ends of the disclosed sequence.

In another embodiment, polynucleotides are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In certain embodiments, the polynucleotides described above, e.g., polynucleotide variants, fragments and hybridizing sequences, encode antibodies that bind FN14, or antigen-binding fragments thereof. In other embodiments, such polynucleotides encode antibodies or antigen-binding fragments, or CDRs thereof, that bind to FN14 at least about 50%, preferably at least about 70%, and more preferably at least about 90% as well as an antibody sequence specifically set forth herein. In further embodiments, such polynucleotides encode antibodies or antigen-binding fragments, or CDRs thereof, that bind to FN14 with greater affinity than the antibodies set forth herein, for example, that bind quantitatively at least about 105%, 106%, 107%, 108%, 109%, or 110% as well as an antibody sequence specifically set forth herein.

Determination of the three-dimensional structures of representative polypeptides (e.g., variant FN14-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. See, for instance, Donate et al., 1994 *Prot. Sci.* 3:2378; Bradley et al., *Science* 309: 1868-1871 (2005); Schueler-Furman et al., Science 310:638 (2005); Dietz et al., *Proc. Nat. Acad. Sci. USA* 103:1244 (2006); Dodson et al., *Nature* 450:176 (2007); Qian et al., *Nature* 450:259 (2007); Raman et al. *Science* 327:1014-1018 (2010). Some additional non-limiting examples of computer algorithms that may be used for these and related embodiments, such as for rational design of FN14-specific antibodies antigen-binding domains thereof as provided herein, include NAMD, a parallel molecular dynamics code designed for high-performance simulation of large biomolecular systems, and VMD which is a molecular visualization program for displaying, animating, and analyzing large biomolecular systems using 3-D graphics and built-in scripting (see Phillips, et al., *Journal of Computational Chemistry,* 26:1781-1802, 2005; Humphrey, et al., "VMD—Visual Molecular Dynamics", *J. Molec. Graphics,* 1996, vol. 14, pp. 33-38; see also the website for the Theoretical and Computational Biophysics Group, University of Illinois at Urbana-Champagne, at ks.uiuc.edu/Research/vmd/). Many other computer programs are known in the art and available to the skilled person and which allow for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) *J. Comput. Chem.* 4:187-217) and AMBER (Weiner et al (1981) *J. Comput. Chem.* 106: 765), which assess force field calculations, and analysis (see also, Eisenfield et al. (1991) *Am. J. Physiol.* 261:C376-386; Lybrand (1991) *J. Pharm. Belg.* 46:49-54; Froimowitz (1990) *Biotechniques* 8:640-644; Burbam et al. (1990) *Proteins* 7:99-111; Pedersen (1985) *Environ. Health Perspect.* 61:185-190; and Kini et al. (1991) *J. Biomol. Struct. Dyn.* 9:475-488). A variety of appropriate computational computer programs are also commercially available, such as from Schrödinger (Munich, Germany).

The polynucleotides described herein, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J., *Unified Approach to Alignment and Phylogenes*, pp. 626-645 (1990); *Methods in Enzymology* vol. 183, Academic Press, Inc., San Diego, Calif.; Higgins, D. G. and Sharp, P. M., CABIOS 5:151-153 (1989); Myers, E. W. and Muller W., CABIOS 4:11-17 (1988); Robinson, E. D., Comb. Theor 11:105 (1971); Santou, N. Nes, M., Mol. Biol. Evol. 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity among two or more the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode an antibody as described herein. Some of these polynucleotides bear minimal sequence identity to the nucleotide sequence of the native or original polynucleotide sequence, such as those described herein that encode antibodies that bind to FN14. Nonetheless, polynucleotides that vary due to differences in codon usage are expressly contemplated by the present disclosure. In certain embodiments, sequences that have been codon-optimized for mammalian expression are specifically contemplated.

Therefore, in another embodiment of the invention, a mutagenesis approach, such as site-specific mutagenesis, may be employed for the preparation of variants and/or derivatives of the antibodies described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the inventors contemplate the mutagenesis of the disclosed polynucleotide sequences to alter one or more properties of the encoded polypeptide, such as the binding affinity of the antibody or the antigen-binding fragment thereof, or the ADCC function of a particular Fc region, or the affinity of the Fc region for a particular FcγR. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants, recursive sequence recombination, as described in U.S. Pat. No. 5,837,458, may be employed. In this approach, iterative cycles of recombination and screening or selection are performed to "evolve" individual polynucleotide variants having, for example, increased binding affinity. Certain embodiments also provide constructs in the form of plasmids, vectors, transcription or expression cassettes which comprise at least one polynucleotide as described herein.

According to certain related embodiments there is provided a recombinant host cell which comprises one or more constructs as described herein; a nucleic acid encoding any antibody, CDR, VH or VL domain, or antigen-binding fragment thereof; and a method of production of the encoded product, which method comprises expression from encoding nucleic acid therefor. Expression may conveniently be achieved by culturing under appropriate conditions recombinant host cells containing the nucleic acid. Following production by expression, an antibody or antigen-binding fragment thereof, may be isolated and/or purified using any suitable technique, and then used as desired.

Antibodies or antigen-binding fragments thereof as provided herein, and encoding nucleic acid molecules and vectors, may be isolated and/or purified, e.g. from their natural environment, in substantially pure or homogeneous form, or, in the case of nucleic acid, free or substantially free of nucleic acid or genes of origin other than the sequence encoding a polypeptide with the desired function. Nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli.

The expression of antibodies and antigen-binding fragments in prokaryotic cells such as E. coli is well established in the art. For a review, see for example Pluckthun, A. Bio/Technology 9: 545-551 (1991). Expression in eukaryotic cells in culture is also available to those skilled in the art as an option for production of antibodies or antigen-binding fragments thereof, see recent reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

The term "host cell" is used to refer to a cell into which has been introduced, or which is capable of having introduced into it, a nucleic acid sequence encoding one or more of the herein described antibodies, and which further expresses or is capable of expressing a selected gene of interest, such as a gene encoding any herein described antibody. The term includes the progeny of the parent cell, whether or not the progeny are identical in morphology or in genetic make-up to the original parent, so long as the selected gene is present. Accordingly there is also contemplated a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. In one embodiment, the nucleic acid is integrated into the genome (e.g. chromosome) of the host cell. Integration may be promoted by inclusion of sequences which promote recombination with the genome, in accordance-with standard techniques.

The present invention also provides, in certain embodiments, a method which comprises using a construct as stated above in an expression system in order to express a particular polypeptide such as an FN14-specific antibody as described herein. The term "transduction" is used to refer to the transfer of genes from one bacterium to another, usually by a phage. "Transduction" also refers to the acquisition and transfer of eukaryotic cellular sequences by retroviruses. The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, MOLECULAR CLONING, A LABORATORY MANUAL, Cold Spring Harbor Laboratories; Davis et al., 1986, BASIC METHODS IN MOLECULAR BIOLOGY, Elsevier; and Chu et al., 1981, Gene 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "naturally occurring" or "native" when used in connection with biological materials such as nucleic acid molecules, polypeptides, host cells, and the like, refers to materials which are found in nature and are not manipulated by a human. Similarly, "non-naturally occurring" or "non-native" as used herein refers to a material that is not found in nature or that has been structurally modified or synthesized by a human.

The terms "polypeptide" "protein" and "peptide" and "glycoprotein" are used interchangeably and mean a polymer of amino acids not limited to any particular length. The term does not exclude modifications such as myristylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the antibodies that bind to FN14 of the present disclosure, or sequences that have deletions from, additions to, and/or substitutions of one or more amino acid of an anti-FN14 antibody. Thus, a "polypeptide" or a "protein" can comprise one (termed "a monomer") or a plurality (termed "a multimer") of amino acid chains.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

The term "polypeptide fragment" refers to a polypeptide, which can be monomeric or multimeric, that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies. In the case of an anti-FN14 antibody, useful fragments include, but are not limited to: a CDR region, especially a CDR3 region of the heavy or light chain; a variable region of a heavy or light chain; a portion of an antibody chain or just its variable region including two CDRs; and the like.

Methods for Generating FN14-Specific Antibodies

The antibodies according to certain embodiments of the present invention may be generated using an in vitro system based on the DT40 chicken B cell lymphoma line. The DT40 chicken B cell lymphoma line has been used for antibody evolution ex vivo (Cumbers, S. J. et al. *Nat Biotechnol* 20, 1129-1134 (2002); Seo, H. et al. *Nat Biotechnol* 23, 731-735 (2005). DT40 cells command enormous potential V region sequence diversity, as they can access two distinct physiological pathways for diversification, gene conversion and somatic hypermutation, which create templated and nontemplated mutations, respectively (Maizels, N. Immunoglobulin gene diversification. *Annu Rev Genet.* 39, 23-46 (2005)). However, the utility of DT40 cells for antibody evolution has been limited in practice because—as in other transformed B cell lines—diversification occurs at less than 1% the physiological rate. Diversification can be accelerated several-fold by disabling the homologous recombination pathway (Cumbers et al., Supra), but cells thus engineered lose the ability to carry out efficient gene targeting. Diversification can also be accelerated by treatment of cells with the histone deacetylase inhibitor, trichostatin A (Seo et al., Supra), but resulting mutations are exclusively templated, which limits potential diversity and may not produce antibodies of required affinity or specificity.

In certain embodiments, the DT40 cells used herein to generate antibodies are modified to accelerate the rate of Ig gene diversification without sacrificing the capacity for further genetic modification or the potential for both gene conversion and somatic hypermutation to contribute to mutagenesis. This was accomplished by putting immunoglobulin (Ig) gene diversification under control of the potent *E. coli* lactose operator/repressor regulatory network. Multimers consisting of approximately 100 polymerized repeats of the potent *E. coli* lactose operator (PolyLacO) were inserted upstream of the rearranged and expressed Igλ and IgH genes by homologous gene targeting (See Example 1;

FIG. 1a). Regulatory factors fused to lactose repressor protein (LacI) can then be tethered to the LacO regulatory elements to regulate diversification, taking advantage of the high affinity ($K_D = 10^{-14}$ M) of lactose repressor for operator DNA. DT40 PolyLacO-$\lambda_R$ cells, in which PolyLacO was integrated only at Igλ, exhibited a 5-fold increase in Ig gene diversification rate relative to the parental DT40 cells prior to any engineering (Cummings, W. J. et al. *PLoS Biol* 5, e246 (2007)). Diversification was further elevated in cells engineered to carry PolyLacO targeted to both the Igλ and the IgH genes ("DTLacO"). As shown in the Examples herein, targeting PolyLacO elements to both the heavy and light chain genes accelerated diversification more than 20-fold relative to the DT40 parental cell line.

In one embodiment, the engineered DTLacO line, which carries PolyLacO at both the heavy and light chain genes, may be used as the starting point for antibody discovery ex vivo. For example, as described in the Examples, starting with a diversified population of between $10^7$-$10^{10}$ DTLacO LacI-HP1 cells, cells that bind to FN14 were enriched by rounds of selection on FN14-bearing solid matrices (Dynal magnetic beads) and by FACS. As would be recognized by the skilled artisan, other methods of selection (e.g., based on antibody binding specificity for FN14) may also be used. Recombinant chimeric monoclonal antibodies having desired binding characteristics are then generated using standard techniques as described herein.

In certain embodiments, (e.g., for generating variants of the anti-FN14 antibodies described herein; for generating antibodies that block binding of the anti-FN14 antibodies described herein) selection of antigen-specific DTLacO cells can then be tested using any of a variety of high throughput approaches including, but not limited to, panning and cell:target cell binding. For example, panning can be carried out by incubating a diverse DTLacO population that contains a low percentage of FN14-specific cells with an array of multiple soluble antigen targets bound to a plastic matrix. Panning significantly enriches FN14-specific DTLacO cells. DTLacO:target cell selection can be carried out by co-incubating a diverse DTLacO population that contained a low percentage of CFSE-labeled DTLacO FN14-binding cells or unselected DTLacO with target cells expressing the antigen of interest, e.g., FN14-expressing cells, which constitutively or transiently express either native or recombinant FN14 on the cell surface, then quantifying DTLacO cells bound to the target cells by flow cytometry. DTLacO interactions with target cells are evident as CFSE-positive events on a dot plot, with the signal from much smaller free DTLacO cells eliminated based on forward scatter.

In certain embodiments, (e.g., for generating antibodies that block binding of the anti-FN14 antibodies described herein) antibodies may similarly be prepared using an in vitro system for generating diversity of a particular polypeptide, as further described in WO2009029315 and US2010093033. In particular, these applications generally relate to the modified B cell, such as the DT40 cell line described herein above, that permits reversible induction of diversification of a target gene. The illustrative B cell is the DT40 B cell line, however the use of other B cells, including human B cells, is contemplated. DT40 is a chicken B cell line that is known to constitutively mutate its heavy and light chain immunoglobulin (Ig) genes in culture. Like other B cells, this constitutive mutagenesis targets mutations to the V region of Ig genes, and thus, the CDRs of the expressed antibody molecules. Constitutive mutagenesis in DT40 cells takes place by gene conversion using as donor sequences an array of non-functional V gene segments (pseudo-V genes; ψV) situated upstream of each functional V region. Deletion of the ψV region was previously shown to cause a switch in the mechanism of diversification from gene conversion to somatic hypermutation, the mechanism commonly observed in human B cells. DT40 has also been shown to support efficient homologous recombination which enables the creation of modified cells in which specific genes are modified, deleted or inserted or where specific genes of interest replace an endogenous gene, in particular an endogenous rearranged Ig gene.

The system described in WO2009029315 and US2010093033 takes advantage of these and other properties to create a platform for diversifying target sequences. More specifically, therein is described a modified B cell that permits reversible induction of diversification of a target gene. The cells are modified to include a "cis-regulatory element" operably linked to a target gene of interest. The cell is further modified to include a "diversification factor" that is fused to a "tethering factor". The function of the tethering factor is to bind to the cis-regulatory element, thereby bringing the diversification factor to the region that controls expression of the target gene. The role of the diversification factor is to accelerate or regulate diversification (mutation) of the target sequence. Since the target gene is inserted into an Ig locus, mutations are targeted to its coding region and controlled by the use of the diversification factor-tethering factor fusion protein. Generally, the cis-regulatory element may be any DNA sequence that allows binding of a tethering factor thereto in a sequence-specific manner and is positioned in a region that controls expression or diversification of a gene (the gene of interest). The cis-regulatory elements include a polymerized Lactose operator (PolyLacO) comprising approximately 100 repeats of the 20 base pair LacO binding site. The cis-regulatory element is positioned within the ψV region of the IgA light chain and the IgH loci. The tethering factor includes the Lac repressor (LacI) that binds with high affinity to the LacO. This insertion of the cis-regulatory element does not affect the normal process of templated mutagenesis (gene conversion) in the modified DT40 cell line.

The inducible aspect of the system of WO2009029315 and US2010093033 occurs through expression of tethering factor (LacI)-diversification factor fusion proteins and the use of IPTG, a small molecule which causes release of LacI from LacO. Culture of the modified DT40 cells with as little as 10 µM IPTG causes release of LacI from the PolyLacO and does not affect cell proliferation. Many different diversification factors are contemplated and include factors that affect chromatin structure, transcriptional activators and other gene regulators, deaminases, proteins involved in DNA repair and replication, resolvases and helicases, cell cycle regulators, proteins of the nuclear pore complex, and proteins involved in ubiquitylation. Different tethering factor-diversification factor constructs include: 1) LacI-HP1: The heterochromatin protein, HP1, promotes a closed chromatin structure of neighboring genes. Thus, when LacI was bound to the PolyLacO in the modified DT40 cells, the tethered HP1 protein caused a transition of the donor ψV sequences from an open to a nonpermissive chromatin state. This was functionally equivalent to the deletion of the ψV region and similarly resulted in the switch from a templated mutagenesis of the downstream Ig Vλ locus to a somatic hypermutation of this targeted region. 2) LacI-VP16: VP16 is a strong transcriptional activator which functions by recruiting histone acetyltransferase complexes. Binding of the LacI-VP16 fusion to the PolyLacO tract resulted in a permissive chromatin structure and an increase in mutagenesis of the Vλ targeted region by gene conversion. 3) LacI-Nup153: Nup153 is a nuclear pore protein and the LacI-Nup153 fusion protein functioned to tether the IgH locus in the modified DT40 cells to the nuclear pore. Since diversification of Ig genes was shown to initiate at the nuclear periphery, mediated by Activation Induced Deaminase (AID) which carries a nuclear export signal, the effect of binding of the LacI-Nup153 fusion protein to the PolyLacO tract was to accelerate diversification by increasing gene proximity to the nuclear pore. The experiments described show that the clonal diversification rate accelerated by 5.7-fold. 4) E47-LacI: E47 is an isoform of E2A, which is a regulator of many aspects of lymphocyte development. This protein is induced in activated murine B cells where it regulates class switch recombination as well as expression of the AID gene. Inactivation of the E2A gene impairs IgA gene diversification. Similarly, ectopic expression of E47 promotes IgA gene diversification. Thus, binding of the E47-

LacI fusion protein to the PolyLacO cis-regulatory element in the modified DT40 cells resulted in an increase in the diversification of the downstream targeted gene. 5) HIRA-LacI: HIRA is a histone chaperone. One of its functions is to assemble nucleosomes containing the H3.3 histone variant. Expression of the HIRA-LacIfusion protein in the PolyLacO modified DT40 cells increased diversification 11-fold. This acceleration was shown to be due to increased levels of templated mutation (gene conversion).

The modified B cells described in WO2009029315 and US2010093033 may be used to generate mutated proteins, and in certain embodiments may be used to generate anti-FN14 antibodies, such as antibodies that block specific binding of the antibodies described herein to their cognate antigens, for instance, by competitive inhibition.

FN14-binding antibodies or antigen-binding fragments thereof as described herein which are modulators, agonists or antagonists of FN14 function are expressly included within the contemplated embodiments. These agonists, antagonists and modulator antibodies or antigen-binding fragments thereof interact with one or more of the antigenic determinant sites of FN14, or epitope fragments or variants of FN14.

As would be recognized by the skilled person, there are many known methods for making antibodies that bind to a particular antigen, such as FN14, including standard technologies, see, e.g., Harlow and Lane, *Antibodies: A Laboratory Manual*, Cold Spring Harbor Laboratory, 1988. In general, antibodies, such as antibodies that specifically block binding of the FN14-binding antibodies expressly disclosed herein to their cognate antigens, can be produced by cell culture techniques, including the generation of monoclonal antibodies as described herein, or via transfection of antibody genes into suitable bacterial or mammalian cell hosts, in order to allow for the production of recombinant antibodies. In certain embodiments, an immunogen comprising a polypeptide antigen (e.g., human FN14 protein comprising amino acid sequence as set forth in SEQ ID NO:89) is initially injected into any of a wide variety of mammals (e.g., mice, rats, rabbits, sheep or goats). In this step, the polypeptide may serve as the immunogen without modification. Alternatively, particularly for relatively short polypeptides, a superior immune response may in some cases be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

In certain embodiments, monoclonal antibodies specific for an antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides may be used in the purification process in, for example, an affinity chromatography step.

Methods of Use and Pharmaceutical Compositions

Provided herein are methods of treatment using the antibodies that bind FN14. In one embodiment, an antibody of the present invention is administered to a patient having a disease involving inappropriate expression of FN14, which is meant in the context of the present disclosure to include diseases and disorders characterized by aberrant FN14, due for example to alterations (e.g., statistically significant increases or decreases) in the amount of a protein present, or the presence of a mutant protein, or both. An overabundance may be due to any cause, including but not limited to overexpression at the molecular level, prolonged or accumulated appearance at the site of action, or increased (e.g., in a statistically significant manner) activity of FN14 relative to that which is normally detectable. Such an overabundance of FN14 can be measured relative to normal expression, appearance, or activity of FN14, and said measurement may play an important role in the development and/or clinical testing of the antibodies described herein.

In particular, the present antibodies are useful for the treatment of a variety of cancers associated with the expression of FN14. For example, one embodiment of the invention provides a method for the treatment of a cancer including, but not limited to, melanoma, salivary carcinomas, breast cancer, hepatocellular carcinoma, ovarian cancer, cervical cancer, colorectal cancers, non-small cell lung cancer (NSCLC; both adenocarcinoma and squamous cell carcinoma), renal cancer, head and neck cancer, bladder cancer, uterine cancer, stomach cancer, esophageal cancer, pancreatic cancer, and glioblastoma multiforme, by administering to a cancer patient a therapeutically effective amount of a herein disclosed FN14-specific antibody. An amount that, following administration, inhibits, reduces the likelihood of occurrence of, prevents or delays the progression and/or metastasis of a cancer in a statistically significant manner (i.e., relative to an appropriate control as will be known to those skilled in the art) is considered effective.

Another embodiment provides a method for preventing or reducing the likelihood of occurrence of metastasis of a cancer including, but not limited to, melanoma, salivary carcinomas, breast cancer, hepatocellular carcinoma, ovarian cancer, cervical cancer, colorectal cancers, non-small cell lung cancer (NSCLC; both adenocarcinoma and squamous cell carcinoma), renal cancer, head and neck cancer, bladder cancer, uterine cancer, stomach cancer, esophageal cancer, pancreatic cancer, and glioblastoma multiforme, by administering to a cancer patient a therapeutically effective amount of a herein disclosed FN14-specific antibody (e.g., an amount that, following administration, inhibits, reduces the likelihood of occurrence of, prevents or delays metastasis of a cancer in a statistically significant manner, i.e., relative to an appropriate control as will be known to those skilled in the art).

Another embodiment provides a method for preventing or reducing the likelihood of occurrence of a cancer including, but not limited to, melanoma, salivary carcinomas, breast cancer, hepatocellular carcinoma, ovarian cancer, cervical cancer, colorectal cancers, non-small cell lung cancer (NSCLC; both adenocarcinoma and squamous cell carcinoma), renal cancer, head and neck cancer, bladder cancer, uterine cancer, stomach cancer, esophageal cancer, pancreatic cancer, and glioblastoma multiforme, by administering to a cancer patient a therapeutically effective amount of a herein disclosed FN14-specific antibody.

Another embodiment provides a method for treating, reducing the severity of, or reducing the likelihood of occurrence of, or preventing inflammation or an inflammatory disease associated with the expression of FN14 (see e.g., Hotta et al., 2010 Kidney International, PMID: 20927042). For example, one embodiment of the invention provides a method for the treatment of inflammation or an inflammatory disease including, but not limited to, Crohn's disease, colitis, dermatitis, psoriasis, diverticulitis, hepatitis, irritable bowel syndrom (IBS), lupus erythematous, nephritis, Parkinson's disease, ulcerative colitis, multiple sclerosis (MS), Alzheimer's disease, arthritis, rheumatoid arthritis, asthma, and various cardiovascular diseases such as atherosclerosis and vasculitis. In certain embodiments, the inflammatory disease is selected from the group consisting of rheumatoid arthritis, diabetes, gout, cryopyrin-associated periodic syndrome, and chronic obstructive pulmonary disorder. In this regard, one embodiment provides a method of treating, or reducing the likelihood of occurrence of, reducing the severity of or preventing inflammation or an inflammatory disease by administering to a patient in need thereof a therapeutically effective amount of a herein disclosed FN14-specific antibody.

In certain contemplated embodiments, an FN14-specific antibody as disclosed herein is the only therapeutically active agent administered to a patient. Alternatively, in certain other embodiments the presently disclosed antibody is administered in combination with one or more other therapeutic agents, including but not limited to cytotoxic agents, chemotherapeutic agents, cytokines, growth inhibitory agents, antihormonal agents, anti-inflammatory agents, kinase inhibitors, anti-angiogenic agents, cardioprotectants, or other therapeutic agents. Such molecules are suitably present in combination, in amounts that are effective for the purpose intended. The skilled medical practitioner can determine empirically the appropriate dose or doses of other therapeutic agents useful herein. The antibodies may be administered concomitantly with one or more other therapeutic regimens. For example, an antibody may be administered to the patient along with chemotherapy, radiation therapy, or both chemotherapy and radiation therapy. In one embodiment, the antibody may be administered in conjunction with one or more other antibodies known in the art to provide therapeutic benefit.

In one embodiment, the presently described antibodies are administered with a chemotherapeutic agent. By "chemotherapeutic agent" is meant a chemical compound useful in the treatment of cancer. Examples of chemotherapeutic agents include but are not limited to alkylating agents such as thiotepa and cyclophosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; thymidylate synthase inhibitor (such as Tomudex); cox-2 inhibitors, such as celicoxib (CELEBREX®.) or MK-0966 (VIOXX®); and pharmaceutically acceptable salts, acids or derivatives of any of the above. Also included are anti-hormonal agents that act to regulate or inhibit hormone action on tumors such as anti estrogens including, for example, tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

A chemotherapeutic or other cytotoxic agent may be administered as a prodrug. By "prodrug" as used herein is meant a precursor or derivative form of a pharmaceutically active substance that is less cytotoxic to tumor cells compared to the parent drug and is capable of being enzymatically activated or converted into the more active parent form. See, for example Wilman, 1986, Biochemical Society Transactions, 615th Meeting Belfast, 14:375-382; and Stella et al., "Prodrugs: A Chemical Approach to Targeted Drug Delivery," Directed Drug Delivery, Borchardt et al., (ed.): 247-267, Humana Press, 1985. The prodrugs that may find use, along with the herein described FN14-specific antibodies, in certain presently contemplated embodiments may include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use with the present FN14-specific antibodies include but are not limited to any of the aforementioned chemotherapeutic agents.

The present FN14-specific antibodies may be combined with other therapeutic regimens. For example, in one embodiment, the patient to be treated with the antibody may also receive radiation therapy. Radiation therapy can be administered according to protocols commonly employed in the art and known to the skilled artisan. Such therapy includes but is not limited to irradiating exposure to art accepted radioisotopes of cesium, iridium, iodine, or cobalt. The radiation therapy may be whole body irradiation, or may be directed locally to a specific site or tissue in or on the body, such as the lung, bladder, or prostate. Typically, radiation therapy is administered in pulses over a period of time from about 1 to 2 weeks. The radiation therapy may, however, be administered over longer periods of time. For instance, radiation therapy may be administered to patients having head and neck cancer for about 6 to about 7 weeks. Optionally, the radiation therapy may be administered as a single dose or as multiple, sequential doses. The skilled medical practitioner can determine empirically the appropriate dose or doses of radiation therapy useful herein. In accordance with another embodiment, the present FN14-specific antibody and one or more other anti-cancer therapies may be employed to treat cancer cells ex vivo. It is contemplated that such ex vivo treatment may be useful in bone marrow transplantation and particularly, autologous bone marrow transplantation. For instance, treatment of cells or tissue(s) containing cancer cells with antibody and one or more other anti-cancer therapies, such as described above, can be employed to deplete or substantially deplete the cancer cells prior to transplantation in a recipient patient. It is of course contemplated that the antibodies described herein can be employed in combination with still other therapeutic techniques such as surgery.

In an alternate embodiment, the herein described antibodies may be administered with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

A variety of other therapeutic agents may find use for administration with the FN14-specific antibodies described herein. In one embodiment, the antibody is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, immune selective anti-inflammatory derivatives (imSAIDS) (see e.g., Bao F, et al. Neuroscience. 2006 Jul. 7; 140(3):1011-22; Mathison R D, et al. BMC Immunol. 2003 Mar. 4; 4:3), methotrexate, sulfasalazine, leflunomide, anti-TNF medications, cyclophosphamide and mycophenolate.

A variety of other therapeutic agents may find use for administration with the FN14-specific antibodies described herein. In one embodiment, the antibody is administered with an anti-angiogenic agent. By "anti-angiogenic agent" as used herein is meant a compound that blocks, or interferes to some degree, the development of blood vessels. The anti-angiogenic factor may, for instance, be a small molecule or a protein, for example an antibody, or cytokine, that binds to a growth factor or growth factor receptor involved in promoting angiogenesis. The preferred anti-angiogenic factor herein is an antibody that binds to Vascular Endothelial Growth Factor (VEGF). In an alternate embodiment, the antibody is administered with a therapeutic agent that induces or enhances adaptive immune response, for example an antibody that targets CTLA-4. In an alternate embodiment, the antibody is administered with a tyrosine kinase inhibitor. By "tyrosine kinase inhibitor" as used herein is meant a molecule that inhibits to some extent tyrosine kinase activity of a tyrosine kinase. Examples of such inhibitors include but are not limited to quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo [2,3-d]pyrimidines; curcumin (diferuloyl methane, 4,5-bis(4-fluoroanilino)phthalimide); tyrphostines containing nitrothiophene moieties; PD-0183805 (Warner-Lambert); antisense molecules (e.g. those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering A G); pan-ErbB inhibitors such as C1-1033 (Pfizer); Affinitac (ISIS 3521; Isis/Lilly); Imatinib mesylate (ST1571, Gleevec®); Novartis); PKI 166 (Novartis); GW2016 (Glaxo SmithKline); C1-1033 (Pfizer); EKB-569 (Wyeth); Semaxinib (Sugen); ZD6474 (AstraZeneca); PTK-787 (Novartis/Schering AG); INC-1-C11 (Imclone); or as described in any of the following patent publications: U.S. Pat. No. 5,804,396; PCT WO 99/09016 (American Cyanimid); PCT WO 98/43960 (American Cyanamid); PCT WO 97/38983 (Warner-Lambert); PCT WO 99/06378 (Warner-Lambert); PCT WO 99/06396 (Warner- Lambert); PCT WO 96/30347 (Pfizer, Inc); PCT WO 96/33978 (AstraZeneca); PCT WO96/3397 (AstraZeneca); PCT WO 96/33980 (AstraZeneca), gefitinib (IRESSA™, ZD1839, AstraZeneca), and OSI-774 (Tarceva®, OSI Pharmaceuticals/Genentech).

In another contemplated embodiment, an FN14-specific antibody as described herein may be conjugated or operably linked to another therapeutic compound, referred to herein as a conjugate. The conjugate may be a cytotoxic agent, a chemotherapeutic agent, a cytokine, an anti-angiogenic agent, a tyrosine kinase inhibitor, a toxin, a radioisotope, or other therapeutically active agent. Chemotherapeutic agents, cytokines, anti-angiogenic agents, tyrosine kinase inhibitors, and other therapeutic agents have been described above, and all of these aforemention therapeutic agents may find use as antibody conjugates.

In an alternate embodiment, the antibody is conjugated or operably linked to a toxin, including but not limited to small molecule toxins and enzymatically active toxins of bacterial, fungal, plant or animal origin, including fragments and/or variants thereof. Small molecule toxins include but are not limited to saporin (Kuroda K, et al., The Prostate 70:1286-1294 (2010); Lip, W L. et al., 2007 Molecular Pharmaceutics 4:241-251; Quadros E V., et al., 2010 Mol Cancer Ther; 9(11); 3033-40; Polito L., et al. 2009 British Journal of Haematology, 147, 710-718), calicheamicin, maytansine (U.S. Pat. No. 5,208,020), trichothene, and CC1065. Toxins include but are not limited to RNase, gelonin, enediynes, ricin, abrin, diptheria toxin, cholera toxin, gelonin, *Pseudomonas* exotoxin (PE40), *Shigella* toxin, *Clostridium perfringens* toxin, and pokeweed antiviral protein.

In certain related embodiments, the antibody is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al., 1992, Cancer Research 52: 127-131) to generate a maytansinoid-antibody conjugate. Another conjugate of interest comprises an antibody conjugated to one or more calicheamicin molecules. The calicheamicin family of antibiotics are capable of producing double-stranded DNA breaks at sub-picomolar concentrations. Structural analogues of calicheamicin that may also be used (Hinman et al., 1993, Cancer Research 53:3336-3342; Lode et al., 1998, Cancer Research 58:2925-2928) (U.S. Pat. No. 5,714,586; U.S. Pat. No. 5,712,374; U.S. Pat. No. 5,264,586; U.S. Pat. No. 5,773, 001). Dolastatin 10 analogs such as auristatin E (AE) and monomethylauristatin E (MMAE) may find use as conjugates for the presently disclosed antibodies, or variants thereof (Doronina et al., 2003, Nat Biotechnol 21(7):778-84; Francisco et al., 2003 Blood 102(4):1458-65). Useful enzymatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, PCT WO 93/21232. The present disclosure further contemplates embodiments in which a conjugate or fusion is formed between an FN14-specific antibody as described herein and a compound with nucleolytic activity, for example a ribonuclease or DNA endonuclease such as a deoxyribonuclease (DNase).

In an alternate embodiment, a herein-disclosed antibody may be conjugated or operably linked to a radioisotope to form a radioconjugate. A variety of radioactive isotopes are available for the production of radioconjugate antibodies. Examples include, but are not limited to $^{90}Y$, $^{123}I$, $^{125}I$, $^{131}I$, $^{186}Re$, $^{188}Re$, $^{211}At$, and $^{212}Bi$.

Antibodies described herein may in certain other embodiments be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxel/paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. One preferred exemplary cytotoxin is saporin (available from Advanced Targeting Systems, San Diego, Calif.). Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine).

Moreover, an FN14-specific antibody (including a functional fragment thereof as provided herein such as an antigen-binding fragment) may in certain embodiments be conjugated to therapeutic moieties such as a radioactive materials or macrocyclic chelators useful for conjugating radiometal ions. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483-90; Peterson et al., 1999, Bioconjug. Chem. 10:553; and Zimmerman et al., 1999, Nucl. Med. Biol. 26:943-50.

In yet another embodiment, an antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the antibody is conjugated or operably linked to an enzyme in order to employ Antibody Dependent Enzyme Mediated Prodrug Therapy (ADEPT). ADEPT may be used by conjugating or operably linking the antibody to a prodrug-activating enzyme that converts a prodrug (e.g. a peptidyl chemotherapeutic agent, see PCT WO 81/01145) to an active anti-cancer drug. See, for example, PCT WO 88/07378 and U.S. Pat. No. 4,975,278. The enzyme component of the immunoconjugate useful for ADEPT includes any enzyme capable of acting on a prodrug in such a way so as to convert it into its more active, cytotoxic form. Enzymes that are useful in the method of these and related embodiments include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuramimidase useful for converting glycosylated prodrugs into free drugs; beta-lactamase useful for converting drugs derivatized with α-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", may be used to convert prodrugs into free active drugs (see, for example, Massey, 1987, Nature 328: 457-458). Antibody-abzyme conjugates can be prepared for delivery of the abzyme to a tumor cell population.

Other modifications of the FN14-specific antibodies described herein are also contemplated. For example, the antibody may be linked to one of a variety of nonproteinaceous polymers, e.g., polyethylene glycol (PEG), polypropylene glycol, polyoxyalkylenes, or copolymers of polyethylene glycol and polypropylene glycol. In another embodiment, the antibodies may be coupled to differentiation inducers or drugs, and derivatives thereof. Exemplary drugs may include, but are not limited to methotrexate, and pyrimidine and purine analogs. Exemplary differentiation inducers may include but are not limited to phorbol esters and butyric acid.

A variety of linkers may find use in certain embodiments of the present invention to generate antibody conjugates. By "linker", "linker sequence", "spacer", "tethering sequence" or grammatical equivalents thereof, herein is meant a molecule or group of molecules (such as a monomer or polymer) that connects two molecules and often serves to place the two molecules in a preferred configuration. A number of strategies may be used to covalently link molecules together. These include, but are not limited to polypeptide linkages between N- and C-termini of proteins or protein domains, linkage via disulfide bonds, and linkage via chemical cross-linking reagents.

In one such embodiment, the linker is a peptide bond, generated by recombinant techniques or peptide synthesis. Choosing a suitable linker for a specific case where two polypeptide chains are to be connected may depend on one or more various parameters, including but not limited to the nature of the two polypeptide chains (e.g., whether they naturally oligomerize), the distance between the N- and the C-termini to be connected if known, and/or the stability of the linker towards proteolysis and oxidation. Furthermore, the linker may contain amino acid residues that provide flexibility. Thus, the linker peptide may predominantly include one or more of the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 30 amino acid residues. Preferably, the linker is from about 1 to 30 amino acids in length, with linkers of 1, 2, 3, 4, 5, 6, 7, 8, 9, 10, 11, 12, 13, 14, 15, 16, 17, 18 19 and 20 amino acids in length being preferred.

The amino acid residues selected for inclusion in the linker peptide may desirably exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains. Useful linkers include glycine-serine polymers (including, for example, (GS)n, (GSGGS)n (SEQ ID NO:48), (GGGGS)n (SEQ ID NO:49) and (GGGS)n (SEQ ID NO:50), where n is an integer of at least one), glycine-alanine polymers, alanine-serine polymers, and other flexible linkers such as the tether for the shaker potassium channel, and a large variety of other flexible linkers, as will be appreciated by those in the art.

Glycine-serine polymers are preferred in some embodiments, since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies. Suitable linkers may also be identified by screening databases of known three-dimensional structures for naturally occurring motifs that can bridge the gap between two polypeptide chains.

In a preferred embodiment, the linker is not immunogenic when administered in a human patient. Thus linkers may be chosen such that they have low immunogenicity or are thought to have low immunogenicity. For example, a linker may be chosen that exists naturally in a human. In a preferred embodiment the linker has the sequence of the hinge region of an antibody, that is the sequence that links the antibody Fab and Fc regions; alternatively the linker has a sequence that comprises part of the hinge region, or a sequence that is substantially similar to the hinge region of an antibody. Another way of obtaining a suitable linker is by optimizing a simple linker, e.g., (Gly4Ser)n (SEQ ID NO:49), through random mutagenesis. Alternatively, once a suitable polypeptide linker is defined, additional linker polypeptides can be created to select amino acids that more optimally interact with the domains being linked.

Other types of linkers that may be used include artificial polypeptide linkers and inteins. In another embodiment, disulfide bonds are designed to link the two molecules. In another embodiment, linkers are chemical cross-linking agents. For example, a variety of bifunctional protein coupling agents may be used, including but not limited to N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., 1971, Science 238:1098.

Chemical linkers may permit chelation of an isotope. For example, Carbon-14-labeled 1-isothiocyanatobenzyl-3-methyldiethylene triaminepentaacetic acid (MX-DTPA) is an exemplary chelating agent for conjugation of radionuclide to the antibody (see PCT WO 94/11026). The linker may be cleavable, facilitating release of the cytotoxic drug in the cell. For example, an acid-labile linker, peptidase-sensitive linker, dimethyl linker or disulfide-containing linker (Chari et al., 1992, Cancer Research 52: 127-131) may be used. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use to link the antibodies disclosed herein to a fusion partner, or to link the antibodies to a desired conjugate moiety to form an immunoconjugate.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al. Where a therapeutic agent is more potent when free from the antibody portion of the immunoconjugate, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A therapeutic agent such as a toxin or drug may be coupled (e.g., covalently bonded) to an antibody either directly or indirectly (e.g., via a linker group as disclosed herein). For example, in one embodiment, the therapeutic agent is coupled indirectly via the avidin-biotin system or other similar systems. A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Techniques for conjugating therapeutic moieties to antibodies are well known; see, e.g., Amon et al., "Monoclonal Antibodies For Immunotargeting Of Drugs In Cancer Therapy", in Monoclonal Antibodies And Cancer Therapy, Reisfeld et al. (eds.), 1985, pp. 243-56, Alan R. Liss, Inc.); Hellstrom et al., "Antibodies For Drug Delivery", in Controlled Drug Delivery (2nd Ed.), Robinson et al. (eds.), 1987, pp. 623-53, Marcel Dekker, Inc.); Thorpe, "Antibody Carriers Of Cytotoxic Agents In Cancer Therapy: A Review", in Monoclonal Antibodies '84: Biological And Clinical Applications, Pinchera et al. (eds.), 1985, pp. 475-506); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), 1985, pp. 303-16, Academic Press; and Thorpe et al., Immunol. Rev., 62:119-58, 1982.

Administration of the FN14-specific antibodies described herein, in pure form or in an appropriate pharmaceutical composition, can be carried out via any of the accepted modes of administration of agents for serving similar utilities. The pharmaceutical compositions can be prepared by combining an antibody or antibody-containing composition (e.g., an immunoconjugate such as an FN14-specific antibody-saporin immunotoxin) with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition. Administration may be achieved by a variety of different routes, including oral, parenteral, nasal, intravenous, intradermal, subcutaneous or topical. Preferred modes of administration depend upon the nature of the condition to be treated or prevented. An amount that, following administration, reduces, inhibits, reduces the likelihood of occurrence of, prevents or delays the progression and/or metastasis of a cancer is considered effective.

In certain embodiments, the amount administered is sufficient to result in tumor regression, as indicated by a statistically significant decrease in the amount of viable tumor, for example, at least a 50% decrease in tumor mass, or by altered (e.g., decreased with statistical significance) scan dimensions. The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The FN14-specific antibody-containing compositions may be administered alone or in combination with other known cancer treatments, such as radiation therapy, chemotherapy, transplantation, immunotherapy, hormone therapy, photodynamic therapy, etc. The compositions may also be administered in combination with antibiotics used to treat bacterial infections, in particular intracellular bacterial infections.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described FN14-specific antibody in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of an antibody of the present disclosure, for treatment of a disease or condition of interest in accordance with teachings herein.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of an FN14-specific antibody as herein disclosed such that a suitable dosage will be obtained. Typically, this amount is at least 0.01% of the antibody in the composition. When intended for oral administration, this amount may be varied to be between 0.1 and about 70% of the weight of the composition. Certain oral pharmaceutical compositions contain between about 4% and about 75% of the antibody. In certain embodiments, pharmaceutical compositions and preparations according to the present invention are prepared so that a parenteral dosage unit contains between 0.01 to 10% by weight of the antibody prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the antibody of the invention and thereby assists in the delivery of the compound. Suitable agents that may act in this capacity include other monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises a herein-described FN14-specific antibody and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the antibody composition so as to facilitate dissolution or homogeneous suspension of the antibody in the aqueous delivery system.

The compositions may be administered in a therapeutically effective amount, which will vary depending upon a variety of factors including the activity of the specific compound (e.g., FN14-specific antibody) employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

Compositions comprising the herein described FN14-specific antibody may also be administered simultaneously with, prior to, or after administration of one or more other therapeutic agents. Such combination therapy may include administration of a single pharmaceutical dosage formulation which contains a compound of the invention and one or more additional active agents, as well as administration of compositions comprising antibodies of the invention and each active agent in its own separate pharmaceutical dosage formulation. For example, an antibody as described herein and the other active agent can be administered to the patient together in a single oral dosage composition such as a tablet or capsule, or each agent administered in separate oral dosage formulations. Where separate dosage formulations are used, the compositions comprising antibodies and one or more additional active agents can be administered at essentially the same time, i.e., concurrently, or at separately staggered times, i.e., sequentially and in any order; combination therapy is understood to include all these regimens.

The compositions comprising herein described FN14-specific antibodies may be administered to an individual afflicted with a disease as described herein, such as a cancer. For in vivo use for the treatment of human disease, the antibodies described herein are generally incorporated into a pharmaceutical composition prior to administration. A pharmaceutical composition comprises one or more of the antibodies described herein in combination with a physiologically acceptable carrier or excipient as described elsewhere herein. To prepare a pharmaceutical composition, an effective amount of one or more of the compounds is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof.

The compositions comprising FN14-specific antibodies as described herein may be prepared with carriers that protect the antibody against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used herein the singular forms "a", "an" and "the" include plural aspects unless the context clearly dictates otherwise. Thus, for example, reference to "a cell" includes a single cell, as well as two or more cells; reference to "an agent" includes one agent, as well as two or more agents; and so forth.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y.; Current Protocols in Molecular Biology (Greene Publ. Assoc. Inc. & John Wiley & Sons, Inc., NY, N.Y.); Current Protocols in Immunology (Edited by: John E. Coligan, Ada M. Kruisbeek, David H. Margulies, Ethan M. Shevach, Warren Strober 2001 John Wiley & Sons, NY, N.Y.); or other relevant Current Protocol publications and other like references. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

EXAMPLES

Example 1

Generation of FN14-Specific Antibodies Using Ex Vivo Diversification System

The DT40 chicken B cell lymphoma line has been shown to be a promising starting point for antibody evolution ex vivo (Cumbers, S. J. et al. *Nat Biotechnol* 20, 1129-1134 (2002); Seo, H. et al. *Nat Biotechnol* 23, 731-735 (2005)). DT40 cells proliferate robustly in culture, with an 8-10 hour doubling time (compared to 20-24 hr for human B cell lines), and they support very efficient homologous gene targeting (Buerstedde, J. M. et al. *Embo J* 9, 921-927 (1990)). DT40 cells command enormous potential V region sequence diversity, as they can access two distinct physiological pathways for diversification, gene conversion and somatic hypermutation, which create templated and nontemplated mutations, respectively (Maizels, N. *Annu Rev Genet.* 39, 23-46 (2005)). However, utility of DT40 cells for antibody evolution has been limited in practice because—as in other transformed B cell lines—diversification occurs at less than 1% the physiological rate. Diversification can be accelerated several-fold by disabling the homologous recombination pathway (Cumbers, S. J. et al. Supra), but cells thus engineered have lost ability to carry out efficient gene targeting. Diversification can also be accelerated by treatment of cells with the histone deacetylase inhibitor, trichostatin A (Seo et al., Supra), but resulting mutations are exclusively templated, which limits potential diversity and may not produce antibodies of required affinity or specificity.

In this Example, DT40 cells were engineered to accelerate the rate of Ig gene diversification without sacrificing the capacity for further genetic modification or the potential for both gene conversion and somatic hypermutation to contribute to mutagenesis. This was accomplished by putting Ig gene diversification under control of the potent *E. coli* lactose operator/repressor regulatory network.

Figure 1B:
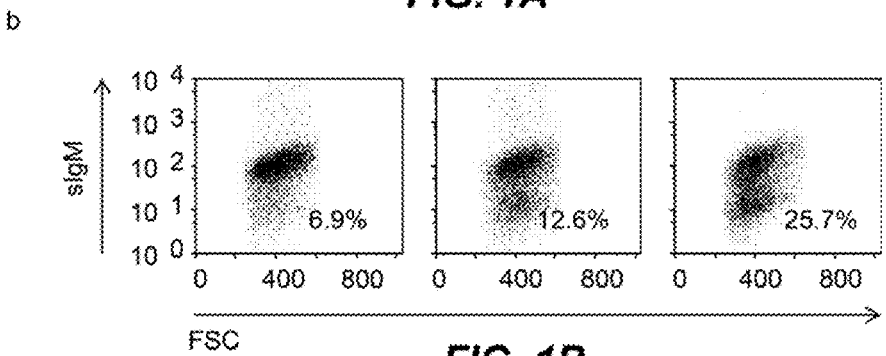
FIG. 1B shows a dot plot from a sIgM loss assay of three representative clonal DTLacO LacI-HP1 transfectants. Fraction of sIgM$^{31}$ cells in each culture indicated in each panel.
Figure 1C:
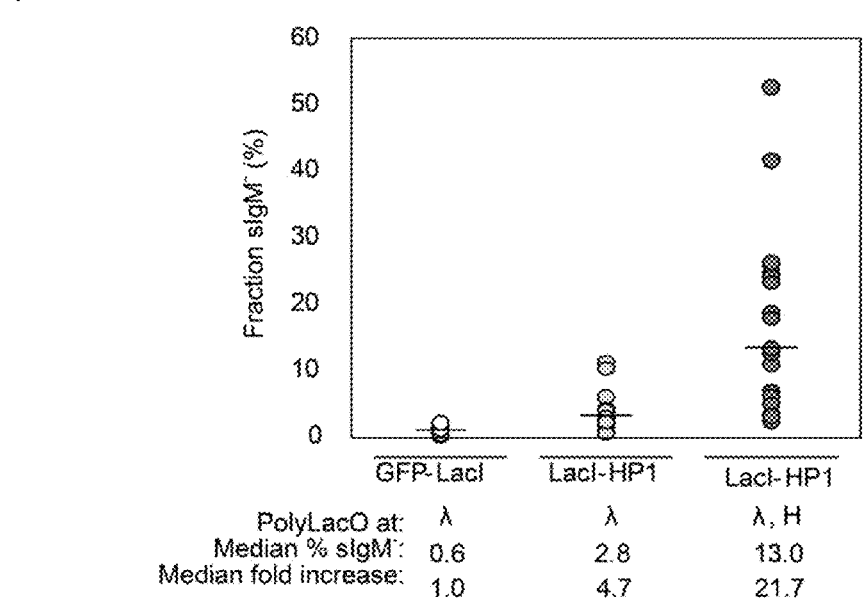
FIG. 1C is a plot summary of sIgM loss assays. Each dot represents the percentage of sIgM cells in one clonal transfectant, analyzed 3 weeks post-transfection. Cells analyzed were: DT40 PolyLacO-λ GFP-LacI control transfectants (n=27); DT40 PolyLacO-λ LacI-HP1 transfectants (n=16) and DTLacO LacI-HP1 transfectants (n=20). Below, median fraction sIgM$^{31}$ cells and median fold increase in sIgM loss of DT40 PolyLacO-λ LacI-HP1 and DTLacO LacI-HP1 transfectants relative to DT40 PolyLacO-λ GFP-LacI control cells.

Multimers consisting of approximately 100 polymerized repeats of the potent *E. coli* lactose operator (PolyLacO) were inserted upstream of the rearranged and expressed Igλ and IgH genes by homologous gene targeting (FIG. 1A). Regulatory factors fused to lactose repressor protein (LacI) can then be tethered to the LacO regulatory elements to regulate diversification, taking advantage of the high affinity ($k_D=10^{-14}$ M) of lactose repressor for operator DNA. DT40 PolyLacO-$\lambda_R$ cells, in which PolyLacO was integrated only at Igλ, exhibited a 5-fold increase in Ig gene diversification rate relative to the parental DT40 cells prior to any engineering (Cummings, W. J. et al. *PLoS Biol* 5, e246 (2007)). Diversification was predicted to be further elevated in cells engineered to carry PolyLacO targeted to both the Igλ and the IgH genes ("DTLacO"). This was confirmed for candidate engineered lines by assaying the fraction of sIgM cells 3 weeks post-transfection with the LacI-HP1 regulatory factor, which showed that diversification rates were 2.5- to 9.2-fold elevated relative to the 2.8% characteristic of the parental DT40 PolyLacO-$\lambda_R$ LacI-HP1 line (e.g. FIG. 1B). Acceleration was reconfirmed for one line by fluctuation assay of individual transfectants (FIG. 1C). Percentages of sIgM cells ranged from 2.5% to 52.5%, with a median of 13.0% in the DTLacO cells (FIG. 1C). This median value is 4.7-fold higher than in DT40 PolyLacO-$\lambda_R$ LacI-HP1 transfectants (2.8%), and 21.7-fold higher than in control cells (DT40 PolyLacO-$\lambda_R$ GFP-LacI (0.6%), comparable to the DT40 parental line (Cummings, W. J. et al. *PLoS Biol* 5, e246 (2007)). Some individual clones exhibited diversification rates considerably different than the median, as predicted because this fluctuation assay measures accumulated sIgM-loss variants (Luria, S. E. & Delbrück, M. *Genetics* 28, 492-511 (1943)). Thus, targeting PolyLacO elements to both the heavy and light chain genes accelerated diversification 21.7-fold relative to the DT40 parental cell line (FIG. 1C).

The engineered DTLacO line, which carried PolyLacO at both the heavy and light chain genes, was then used as the starting point for antibody discovery ex vivo.

The cell surface receptor FN14 is the smallest member of the TNF receptor family, with a highly conserved 53 amino acid extracellular domain (92.4% identity between mouse and human sequences). FN14 is overexpressed in many but not all tumor types, making it a target of therapeutic interest (Feng, S. L. et al. *Am J Pathol* 156, 1253-1261 (2000); Han, H. et al. *Cancer Res* 62, 2890-2896 (2002); Tran, N. L. et al. *Am J Pathol* 162, 1313-1321 (2003); Watts, G. S. et al. *Int J Cancer* 121, 2132-2139 (2007); Willis, A. L. et al. *Mol Cancer Res* 6, 725-734 (2008)). Amino acid and polynucleotide sequences of FN14 are known in the art and available in public databases such as GENBANK. An amino acid sequence of human FN14 is provided in SEQ ID NO: 89.

Figure 2A:
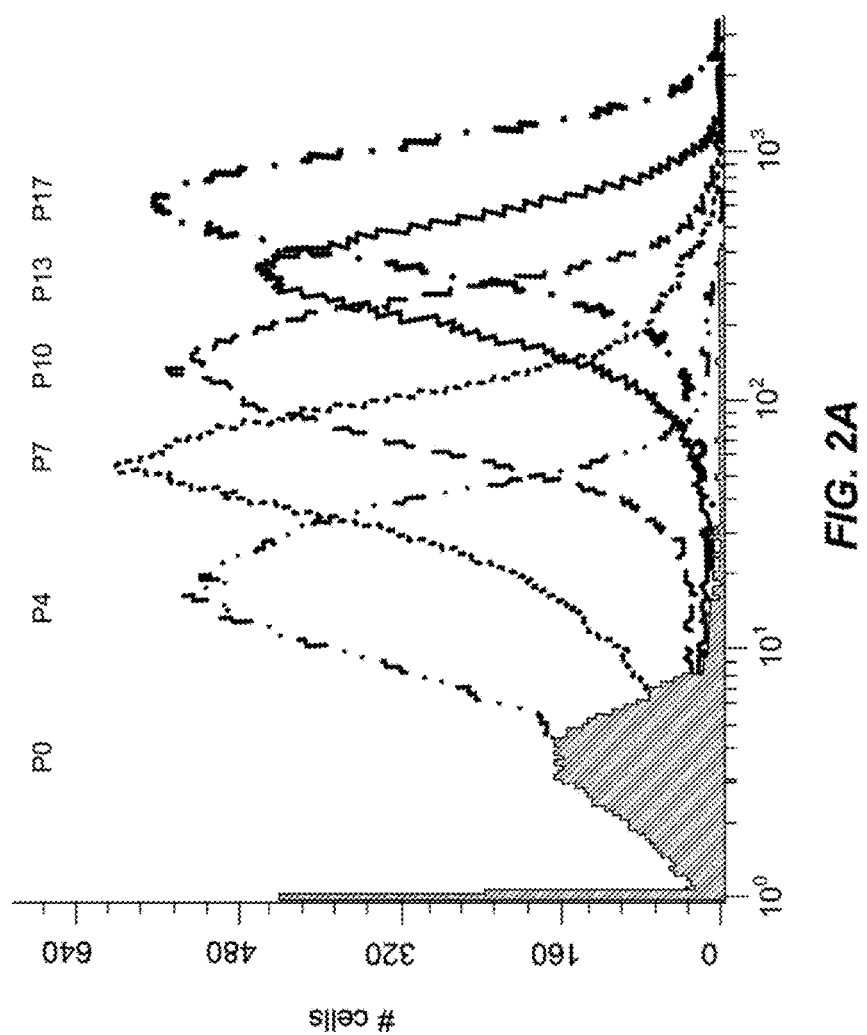
FIG. 2A is a histogram of the binding profile of successive selected DTLacO LacI-HP1 populations to recombinant human FN14-Fc fusion protein (rhFN14-Fc). Populations at indicated successive rounds of selection are designated above peaks (P0-P17).
Figure 2B:
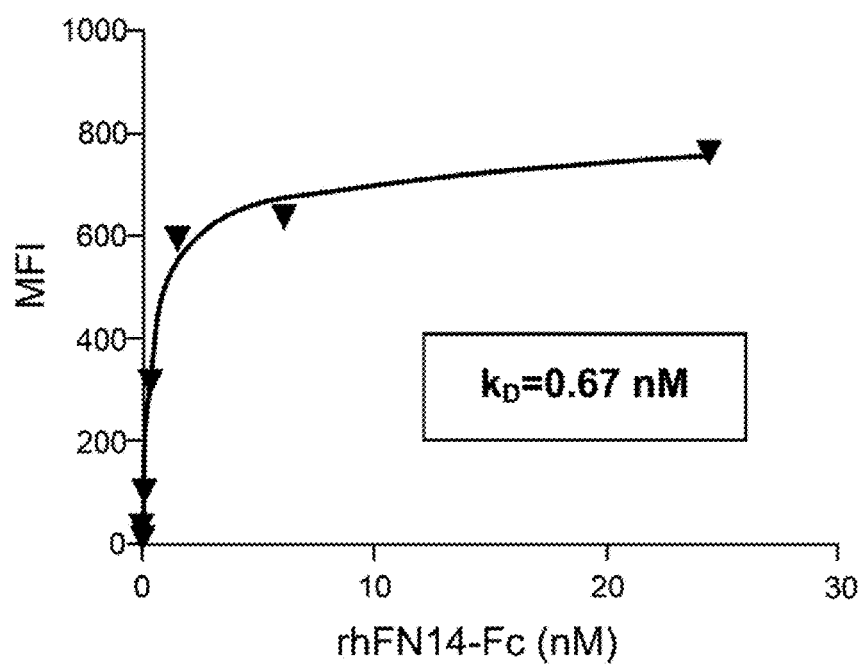
FIG. 2B is a graph showing saturation binding kinetics of FN14-binding subpopulation FS24.

Starting with a diversified population of $10^9$ DTLacO LacI-HP1 cells, binding to FN14 was enriched by selections on solid matrices (Dynal magnetic beads) and by FACS. Seventeen successive populations were characterized by increased affinity (FIG. 2A). Analysis of the saturation binding kinetics of PECy5-labelled soluble antigen to the FN14-specific DTLacO cells provided apparent affinity values of 25 nM and 0.7 nM for populations FS10 and FS17, respectively (not shown), and 0.67 nM for the final population in this lineage FS24 (FIG. 2B).

Figure 2C:
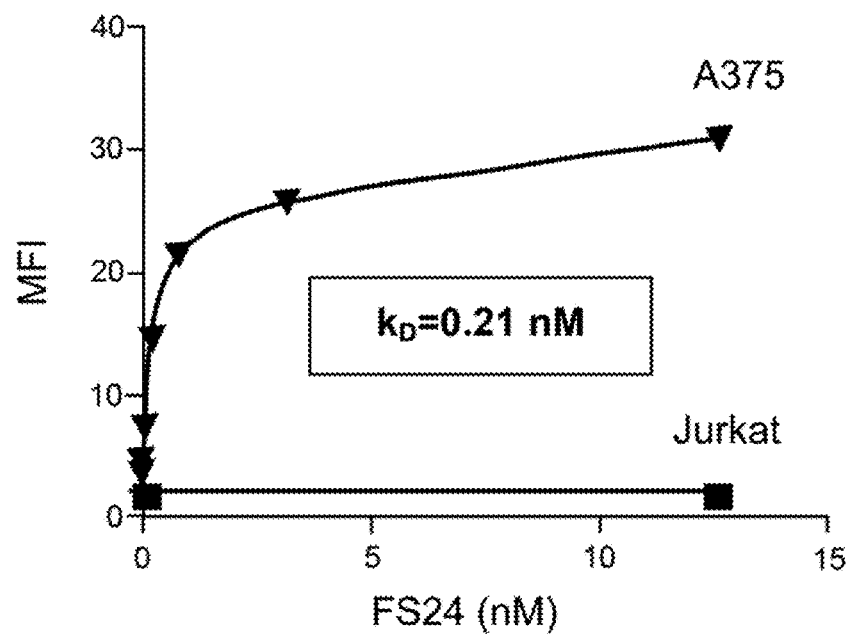
FIG. 2C is a graph showing saturation binding kinetics of mAb FS24 to FN14-expressing melanoma line (A375) and non-expressing T cell leukemia line (Jurkat). Apparent $K_D$=0.21 nM.
Figure 2D:
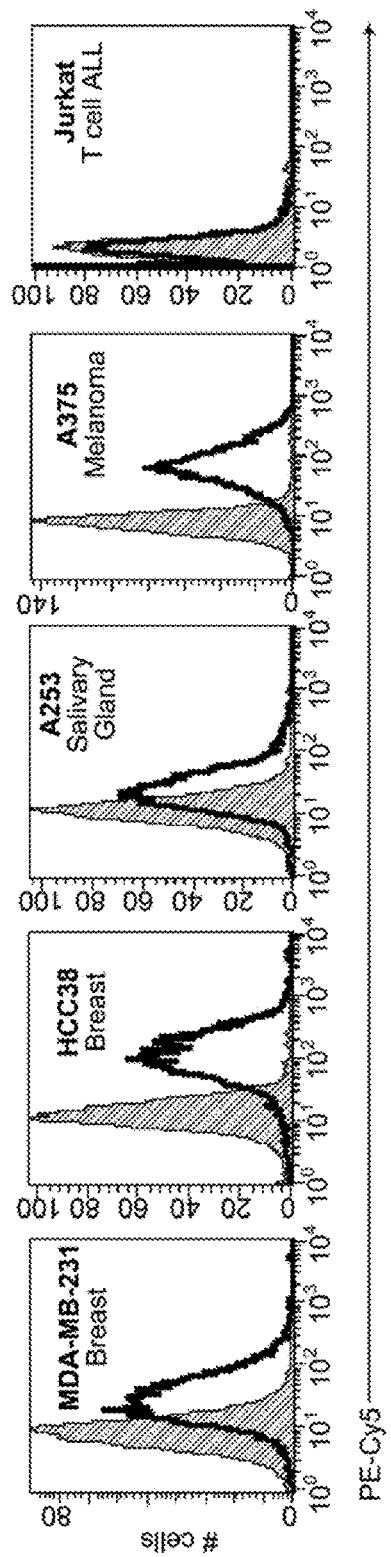
FIG. 2D shows histograms of mAb FS24 binding to cancer lines MDA-MB-231, breast adenocarcinoma; HCC38, breast ductal carcinoma; A253, salivary epidermoid carcinoma; A375, melanoma; Jurkat, T cell leukemia (does not express FN14). FS24 binding is shown in each unfilled curve; secondary antibody alone is shown in each filled curve.
Figure 2E:
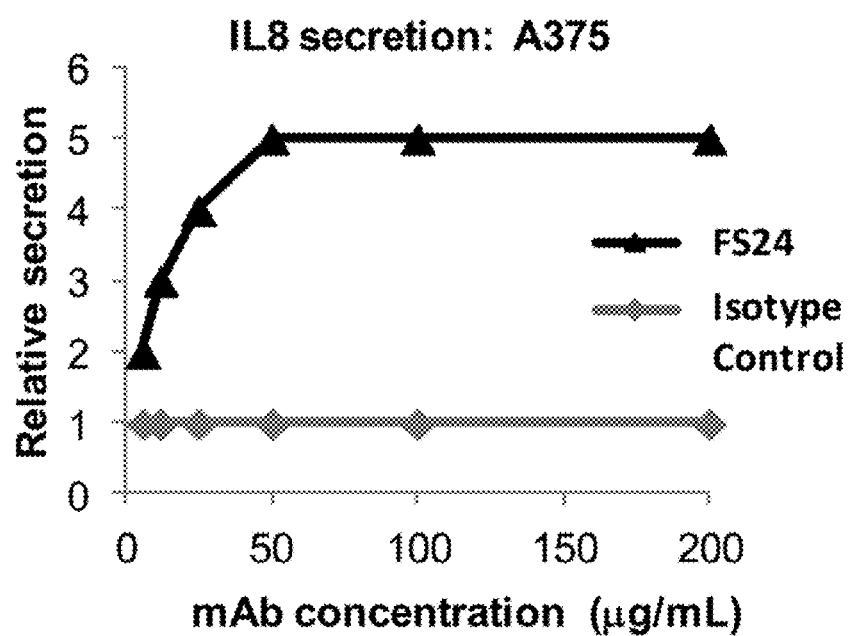
FIG. 2E is a graph showing induction of IL8 secretion by A375 melanoma cells targeted by mAb FS24 or an isotype control.
Figure 2F:
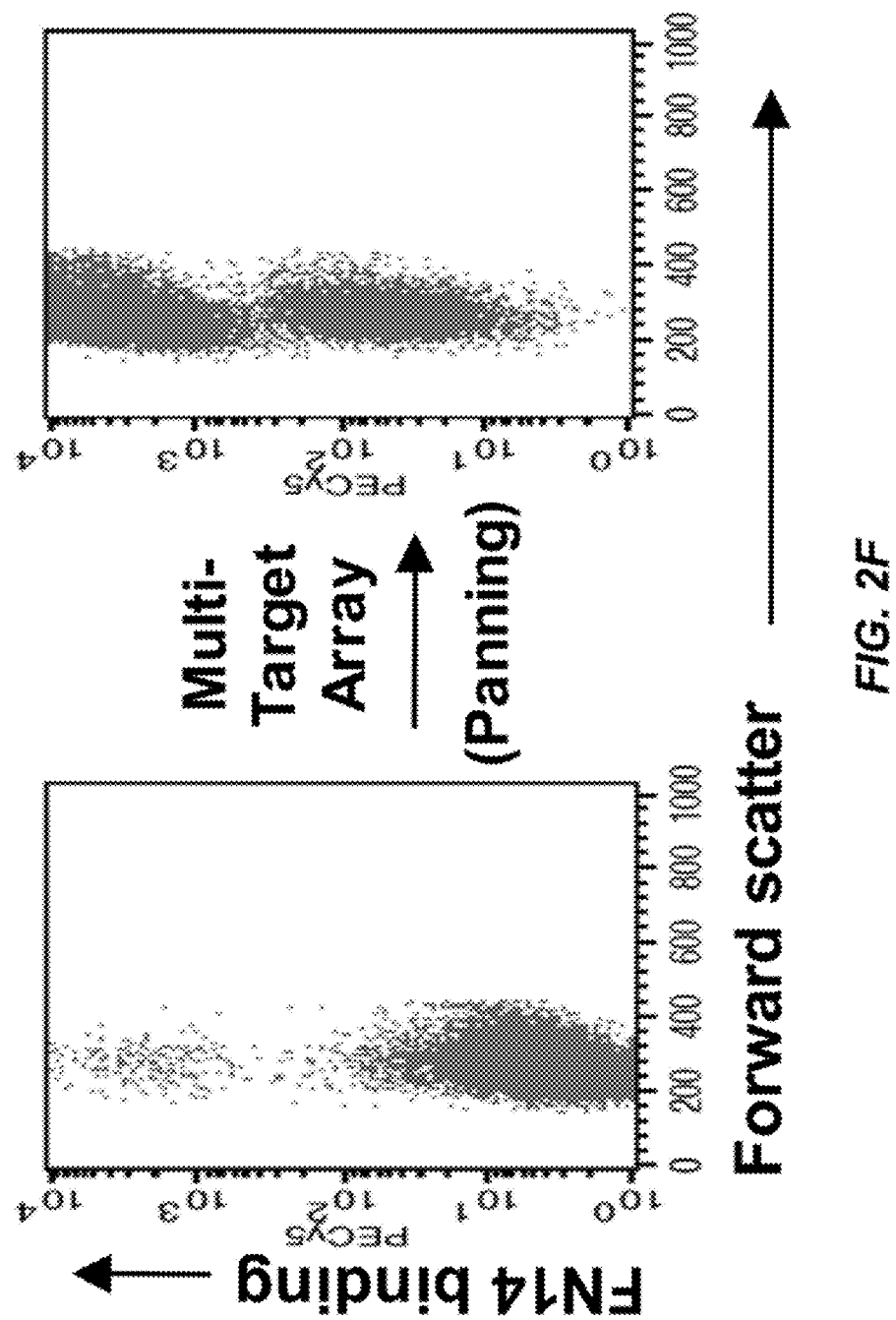
FIG. 2F is a dot plot showing enrichment of FN14 binders by panning on a multi-target array, as measured by binding to rhFN14-Fc. Left panel, diverse population prior to panning; right panel, population selected by panning.
Figure 2G:
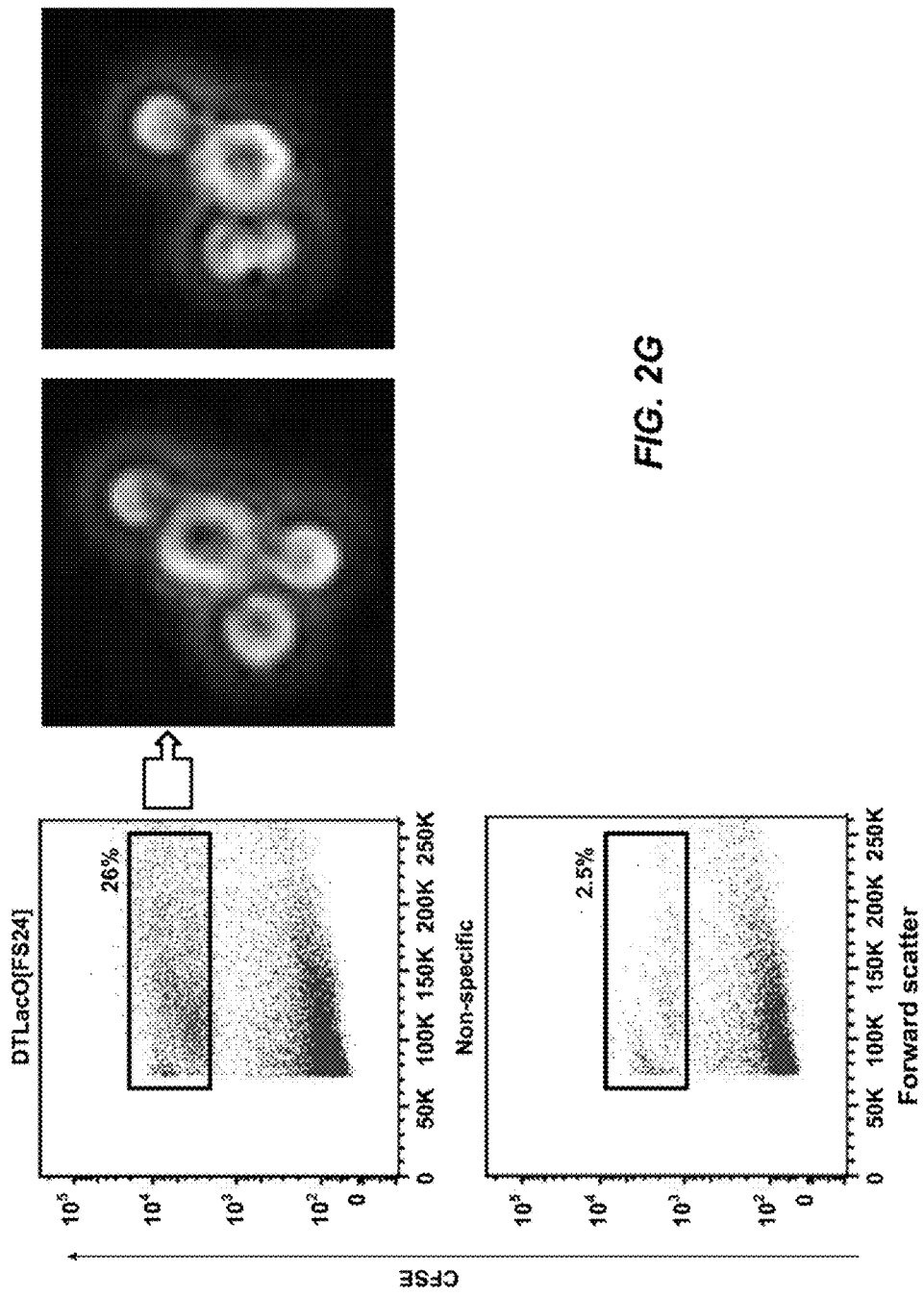
FIG. 2G shows a dot plot profile of interactions of 293F/FN14 target cells with DTLacO population spiked with CFSE-labeled DTLacO[FS24] (above) or non-specific DTLacO (below). The fraction of interacting cells is indicated as a percentage atop each plot. The photomicrograph illustrates the larger 293F/FN14 target cells bound to the smaller DTLacO cells.
Figure 4A:
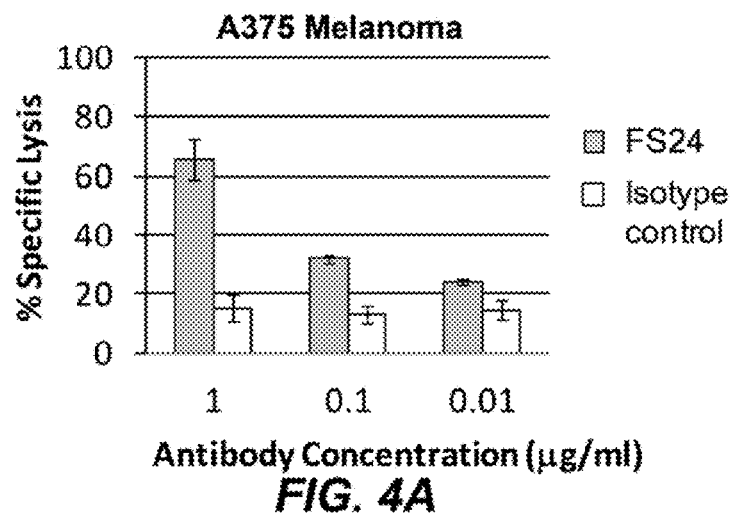
FIG. 4A, FIG. 4B and FIG. 4C are bar graphs showing ADCC killing of melanoma, breast, and pancreatic cancer cells, respectively, by the FS24 FN14-specific antibody.
Figure 4B:
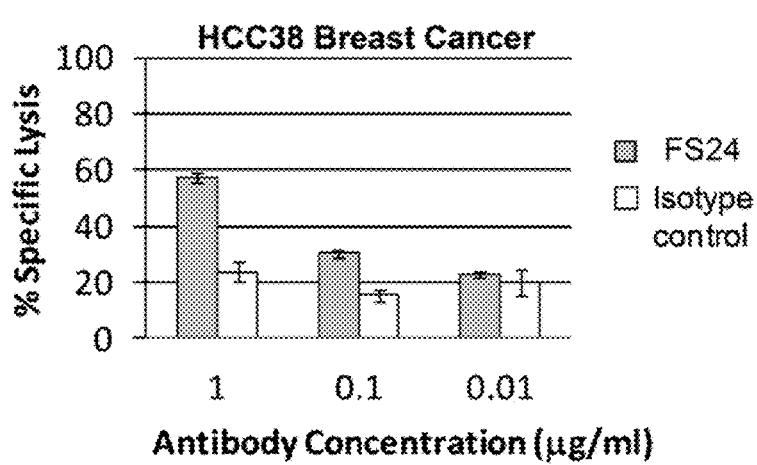
Figure 4C:
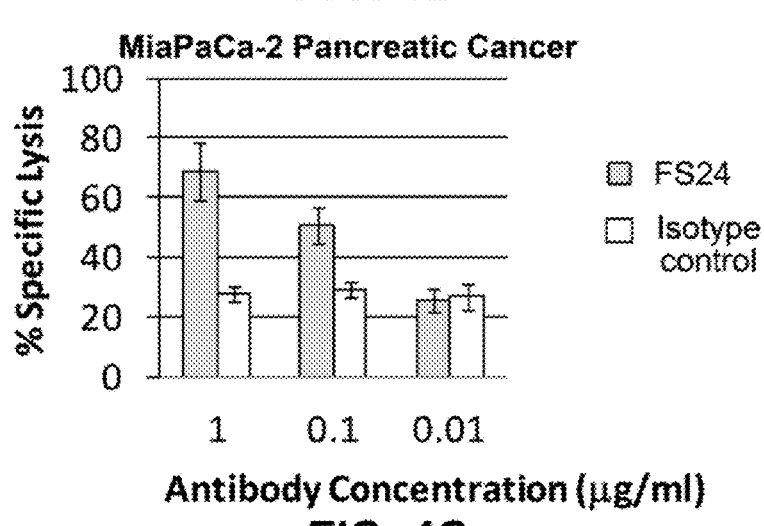

Two additional anti-FN14 populations, PS4A and PS4B, were obtained by panning FS10 cells on a target array that included FN14 (see FIG. 2F). Recombinant chimeric monoclonal antibodies representing these two populations as well as FS10, FS17, and FS24 were generated by fusing the chicken VDJ and VJ elements (see FIG. 3) to the human IgG1 and X, constant regions. The amino acid sequences for the human IgG1 and X, constant regions are set forth in SEQ ID NOs:52 and 54, respectively, which are encoded by the polynucleotide sequences set forth in SEQ ID NOs:51 and 53, respectively. The apparent affinities of these mAbs were determined by measuring saturation binding kinetics of the mAbs to cells expressing FN14 (summarized in Table 1). mAb FS24 did not bind control Jurkat T cells, which do not express FN14, but did bind to FN14-expressing A375 melanoma cells with 0.21 nM affinity (FIG. 2C), comparable to the affinity of the DTLacO[FS24] population for soluble FN14 (0.44 nM, FIG. 2B). mAb FS24 recognized FN14 on the surface of numerous cell types derived from tumors which overexpress FN14, including melanoma, breast, and salivary carcinomas, but not to control Jurkat T cells (FIG. 2D). mAb FS24 also exhibited functionality in cell-based assays. It exhibited weak agonist activity evident as stimulation of secretion of IL8 by A375 cells (FIG. 2E), although compared to TWEAK, the agonist activity was nearly undetectable (not shown). FS24 also promoted antibody-dependent cellular cytotoxicity (ADCC) of A375 melanoma, HCC38 breast carcinoma and MiaPaCa-2 pancreatic cancer cells (FIG. 4).

TABLE 1

Affinities of successive generations of FN14 antibodies

| Generation | Affinity $(K_D)$[1] |
|---|---|
| FS10 | 25 nM |
| FS17 | 0.36 nM |
| FS24 | 0.21 nM |
| PS4A | 0.21 nM |
| PS4B | 0.35 nM |

[1]Determined by measuring saturation binding kinetics of recombinant antibody on target-expressing cells.

The following methods were used in this Example.

Cell Culture and Gene Targeting.

Cell lines were purchased from ATCC unless otherwise indicated. DT40-derived cell lines were maintained and transfected as previously described (Yabuki, M., Fujii, M. M. & Maizels, N. *Nat Immunol* 6, 730-736 (2005)), and other cell lines as specified by the source of origin. The PolyLacO regulatory element (Robinett, C. C. et al. *J Cell Biol* 135, 1685-1700 (1996)), consisting of approximately 100 repeats of the lactose operator (LacO), was targeted to the rearranged and expressed heavy chain allele of DT40 PolyLacO-$\lambda_R$ cells, previously engineered to carry PolyLacO at the rearranged and expressed light chain allele (Cummings, W. J. et al. *PLoS Biol* 5, e246 (2007); Yabuki, M., Ordinario, E. G., Cummings, W. J., Fujii, M. M. & Maizels, N. *J Immunol* 182, 408-415 (2009); Cummings, W. J., Bednarski, D. W. & Maizels, N. *PLoS ONE* 3, e4075 (2008)). Gene targeting was carried out as described (Yabuki et al., supra), using the targeting construct, pPolyLacO-$\psi V_H$. To generate this construct, a 4-kb fragment from the $\psi V_H$ array was amplified from DT40 genomic DNA, cloned into the BglII-BamHI site of pSV40/Zeo2 vector (Invitrogen), and PolyLacO and histidinol-resistance marker fragments were inserted into the $\psi V_H$ fragment. The construct was verified by restriction analyses and partial sequencing, and propagated in recombination-deficient *E. coli* strains Stb12 (Invitrogen) to maintain repeat stability. Following transfection of DT40 PolyLacO-$\lambda_R$ cells, stable transfectants were selected and screened by Southern blotting. The loxP-flanked selection marker was deleted by transient expression of Cre recombinase, and accelerated diversification was tested in cells stably transfected with LacI-HP1 (Cummings, et al. 2007 supra). DTLacO cells stably expressing LacI-HP1 or E47-LacI (Yabuki et al., supra) were used for selection of antigen-specific lineages.

Quantitation of Diversification Rates and V Region Sequence Analysis.

Diversification rates were quantified using the sIgM loss assay, which measures the fraction of cells that have lost expression of IgM on the cell surface due to diversification events (Yabuki, M., Fujii, M. M. & Maizels, N. *Nat Immunol* 6, 730-736 (2005); Sale, J. E., Calandrini, D. M., Takata, M., Takeda, S. & Neuberger, M. S, *Nature* 412, 921-926 (2001)). In brief, panels of approximately 20 independent transfectants were expanded for 3 weeks, then cells (~1×10$^6$) from each panel member were stained with R-phycoerythrin (R-PE) or Spectral Red (SPRD) conjugated anti-chicken IgM (SouthernBiotech), and analyzed on a FACScan with CellQuest software (BD Biosciences). Cells with fluorescence intensity less than one-eighth the median of the sIgM$^+$ peak were scored as sIgM$^-$. Single-cell PCR and sequence analysis were performed as described (Cummings et al., 2007 supra).

Antigens and Selection for Antigen Binding.

Initial selections were performed by binding diversified DTLacO populations to beads complexed with antigen; and subsequent selections by FACS, using fluorescence-labeled soluble antigen (Cumbers et al. and Seo et al., supra). To select cells that recognized FN14, the antigen was recombinant human FN14-Fc fusion protein (rhFN14-Fc; R&D Systems) bound to Dynal magnetic Protein G beads or detected with PECy5-labeled anti-human IgG(Fc). For multi-target array panning, a population containing less than 1% of the FS10 FN14-binding population that had been allowed to further diversify in culture for several weeks was subjected to panning on multiple targets including rhFN14-Fc arrayed on plastic (see FIG. 2F).

Binding, Affinity and Functionality Assays.

Recombinant antibodies were generated by cloning PCR-amplified V regions (Cummings et al., 2007 Supra) into a vector that supported expression of human IgG1 in 293F cells. Saturation binding kinetics were determined by either staining FN14-specific DTLacO cells with various concentrations of fluorescent-labeled soluble antigen, or by staining FN14-transfected cells or cancer cell lines intrinsically expressing FN14 with various concentrations of the recombinant chimeric anti-FN14 mAbs. To assay cell surface FN14 binding, cells were stained with chimeric mAb FS24 at 1 µg/ml or secondary antibody alone and analyzed by FACS. To assay IL8 secretion, A375 melanoma cells were incubated with indicated concentrations of mAb FS24 or isotype control for 24 hours; medium was then assayed for the presence of IL8 using the IL8 CBA flex fluorescent bead assay (BD Biosciences); and mean fluorescent intensities were normalized to background signal.

Example 2

FS24 FN14-Specific Antibody Kills Cancer Cells Via ADCC

Further experiments showed that the FS24 FN14-specific antibody kills cancer cells via ADCC. To assay ADCC, cancer cells as noted in FIG. 4 were incubated with indicated concentrations of mAb FS24 or the isotype control antibody, followed by incubation with total human PBMCs (effector: target ratio 25:1), and the percent specific lysis was determined by europium release (Delfia EuTDA; Perkin Elmer) from the cancer cells.

As shown in FIG. 4, FN14-specific antibody, FS24, showed over 60% lysis of melanoma and pancreatic cancer cells at 1 ug/ml concentration and over 55% lysis of breast cancer cells at the same concentration.

Example 3

Humanization of the FS24 and PS4 Anti-FN14 Antibodies

The FS24 and PS4 chimeric antibodies were humanized using the CDR grafting approach first described for humanization of a mouse antibody (Queen, et al. *Proc Natl Acad Sci USA*. (1989) December; 86(24):10029-33) and recently reviewed by Tsurushita and Vasquez (2004) and Almagro and Fransson (2008) (Tsurushita et al., *J Immunol Methods*. 2004 December; 295(1-2):9-19; Almagro and Fransson, *J. Front Biosci*. (2008) 13:1619-33).

Consensus human framework sequences were chosen for both the VH and VL of PS4, and in both cases were the subgroup consensus sequence with the highest level of identity to the corresponding PS4 variable region sequence. To humanize the VH of PS4, a consensus sequence of human subgroup III VH sequences (Kabat E A, et al. (1991) *Sequences of Proteins of Immunological Interest*, Fifth Edition. NIH Publication No. 91-3242) was chosen as the acceptor framework sequence. To humanize the VL of PS4, a consensus sequence of human subgroup III lambda variable sequences (Kabat et al., supra) was chosen as the acceptor framework. However, a simple grafting of CDRs into an acceptor framework usually results in reduced affinity for ligand, suggesting the desirability of replacing one or more residues in the framework sequence with the amino acid found at that position in the original antibody. In particular, residues within the framework sequence that potentially contact antigen or alter the conformation of a neighboring CDR ("Vernier zone" residues) often may beneficially be reverted to the original residue to retain full affinity for ligand (Foote, J and Winter, G. J Mol. Biol. (1992) 224:487-99). Accordingly, all residues comprising the Vernier zone residues in the PS4 were made identical to those residues found in the original PS4 antibody. Thus, the human residue at each of positions 49, 67, 93 and 94 in humanized VH was changed to the residue found in PS4, while similar human to chicken replacements were also made at positions 46, 66, 69 and 71 in humanized VL (Kabat numbering system, Kabat et al., supra) (see FIG. 6).

Figure 5:
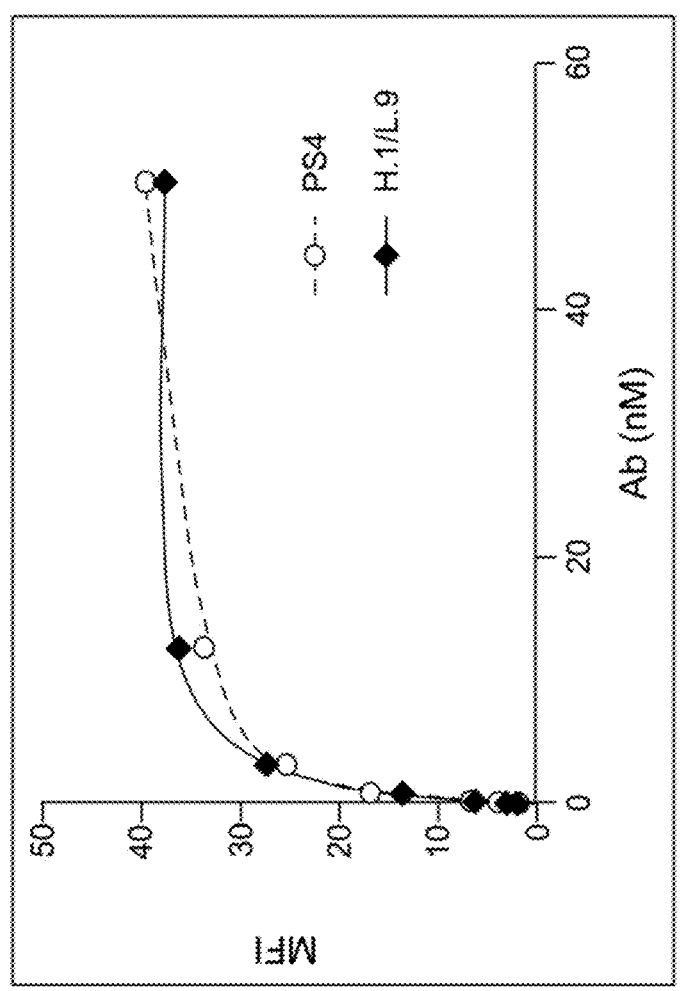
FIG. 5 shows a graph of binding affinity for PS4 and the humanized PS4 antibody H.1/L.9.

Surprisingly, the first humanized version of PS4 constructed using the above strategy (H.1/L.1) had an almost two-log reduced affinity for FN14 compared to the chimeric PS4 antibody (Table 2). As a possible explanation for this result, it was noted that chicken lambda light chains are missing the two amino-terminal residues found in human lambda light chains at positions 1 and 2 (Kabat numbering). Furthermore, the N-terminus of light chains in mammalian antibodies is proximal to L-CDR1. Thus, it seemed possible that the additional two residues at the N-terminus of humanized VL might interfere with antigen binding through steric interference. These two amino acids were deleted in the humanized light chain variant L.9. Also changed in variant L.9 was the new amino-terminal residue of the humanized light chain, which was changed from glutamate (present in the human consensus sequence) to alanine (present in PS4 VL). As shown in FIG. 5 and Table 2, the resulting humanized antibody (H.1/L.9) had an affinity essentially equivalent to that of the original chimeric antibody PS4. An additional variant of the humanized light chain was made (L.18) in which the N-terminal amino acid of the L.9 light chain variant was changed from alanine (PS4) to glutamate (human) and this variant also had an affinity very close to that of the original PS4 chimeric antibody. In contrast to these results, two previous reports describing humanization of a chicken antibody (Nishibori N, et al., *Molecular Immunology* 43 (2006) 634-642; Tsurushita N, et al. *J Immunol Methods.* 2004 December; 295(1-2):9-19) did not require deletion of residues from the N-terminus of the humanized light chain. This difference could be explained if light chain CDR1 in the antibodies described by Nishibori and Tsurushita did not contact antigen and thus was not affected by the two additional N-terminal residues present in humanized light chain and not present in the original chicken antibody.

Humanized sequences of the PS4 antibody are provided in FIG. 6 and SEQ ID NOs:42-47. As summarized in Table 2 below, the H.1/L.9 humanized version of PS4 maintained FN14 binding nearly equivalent to the parent chimeric PS4 antibody (see also FIG. 5).

TABLE 2

Binding affinity of humanized PS4 antibodies

| Antibody | Affinity ($K_D$) |
|---|---|
| Chicken PS4 | 0.21 nM |
| Humanized PS4: H.1/L.1 | 15 nM |
| Humanized PS4: H.9/L.1 | 11 nM |
| Humanized PS4: H.1/L.9 | 0.24 nM |
| Humanized PS4: H.9/L.9 | 0.40 nM |

The polynucleotide sequence for H.1 (including the leader sequence) is provided in SEQ ID NO:47, encoding the amino acid sequence provided in SEQ ID NO:46. The L.9 polynucleotide sequence is provided in SEQ ID NO:43 (including the leader sequence), and encodes the amino acid sequence provided in SEQ ID NO:42. The framework sequence of humanized PS4 VL.9 was 94% human. The framework sequence of humanized PS4 VH.1 was 95% human (see FIG. 6).

A second anti-FN14 antibody, FS24, was humanized using the same strategy. As for PS4, the acceptor framework sequence for humanized FS24 VH was a consensus sequence of human subgroup III VH sequences (Kabat, supra). To humanize the VL of FS24, a consensus sequence of human subgroup III lambda variable sequences (Kabat et al., supra) was chosen as the acceptor framework. As for PS4, the human residue at each of the Vernier Zone residues 49, 67, 93 and 94 in humanized FS24 VH was changed to the residue found in FS24, while similar human-to-chicken replacements were also made at positions 46, 47, 66, 69 and 71 in humanized FS24 VL (Kabat numbering system, Kabat et al., supra).

Figure 7:
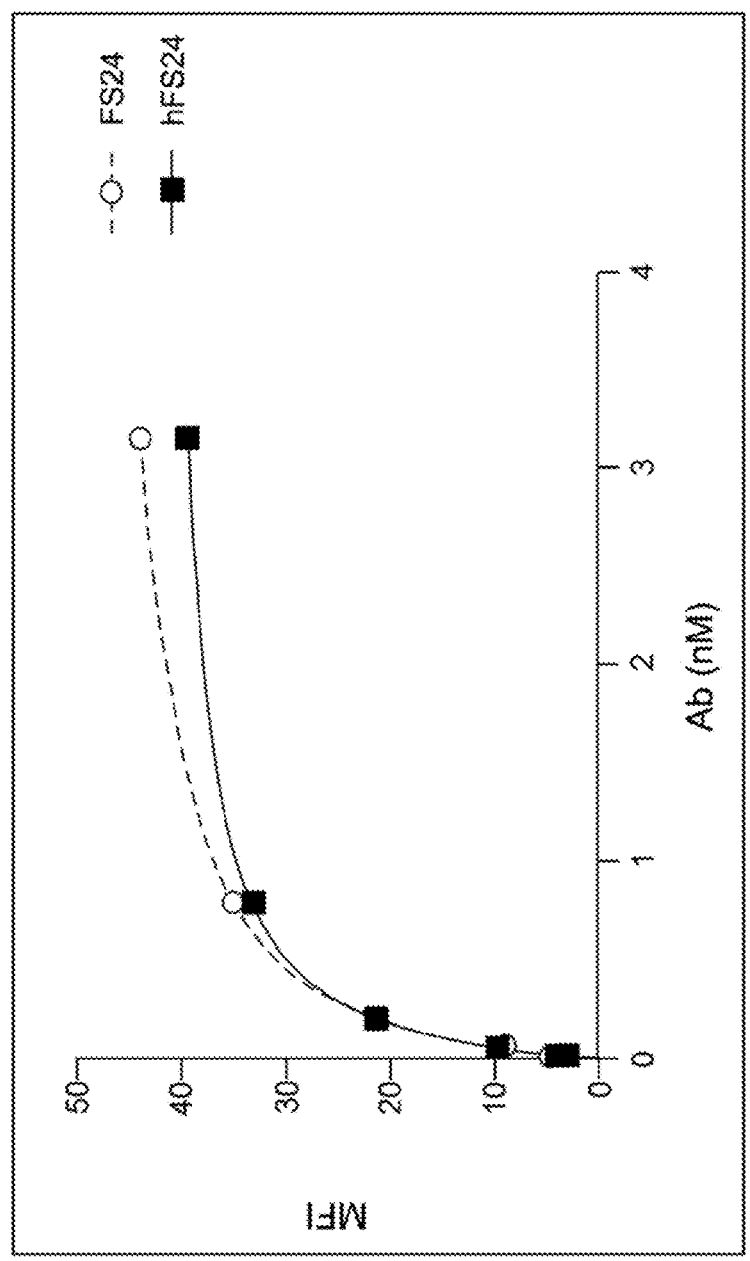
FIG. 7 shows a graph of binding affinity for FS24 and the humanized FS24 antibody hFS24.

As summarized in Table 3 below, the humanized version of FS24 maintained FN14 binding essentially equivalent to the parent chimeric FS24 antibody (see also FIG. 7).

TABLE 3

Binding affinity of humanized FS24 antibodies

| Antibody | Affinity ($K_D$) |
|---|---|
| Chicken FS24 | 0.26 nM |
| Humanized FS24 | 0.21 nM |

Humanized sequences of the FS24 antibody are shown in FIG. 8 and are set forth in SEQ ID NOs:60-63 and 90-91. The polynucleotide sequence for humanized FS24 heavy chain (including the leader sequence) is provided in SEQ ID NO:63, encoding the amino acid sequence provided in SEQ ID NO:62. The humanized FS24 light chain polynucleotide sequence is provided in SEQ ID NO:61 (including the leader sequence), and the encoded amino acid sequence is provided in SEQ ID NO:60. The amino acid sequences of the humanized FS24 heavy and light chain variable regions are provided in SEQ ID NOs:90 and 91, respectively. The framework sequence of humanized FS24 VL was 95% human. The framework sequence of humanized FS24 VH was 95% human (see FIG. 8).

Example 4

FS24 Internalization Upon Binding to Cancer Cells

Figure 9A:
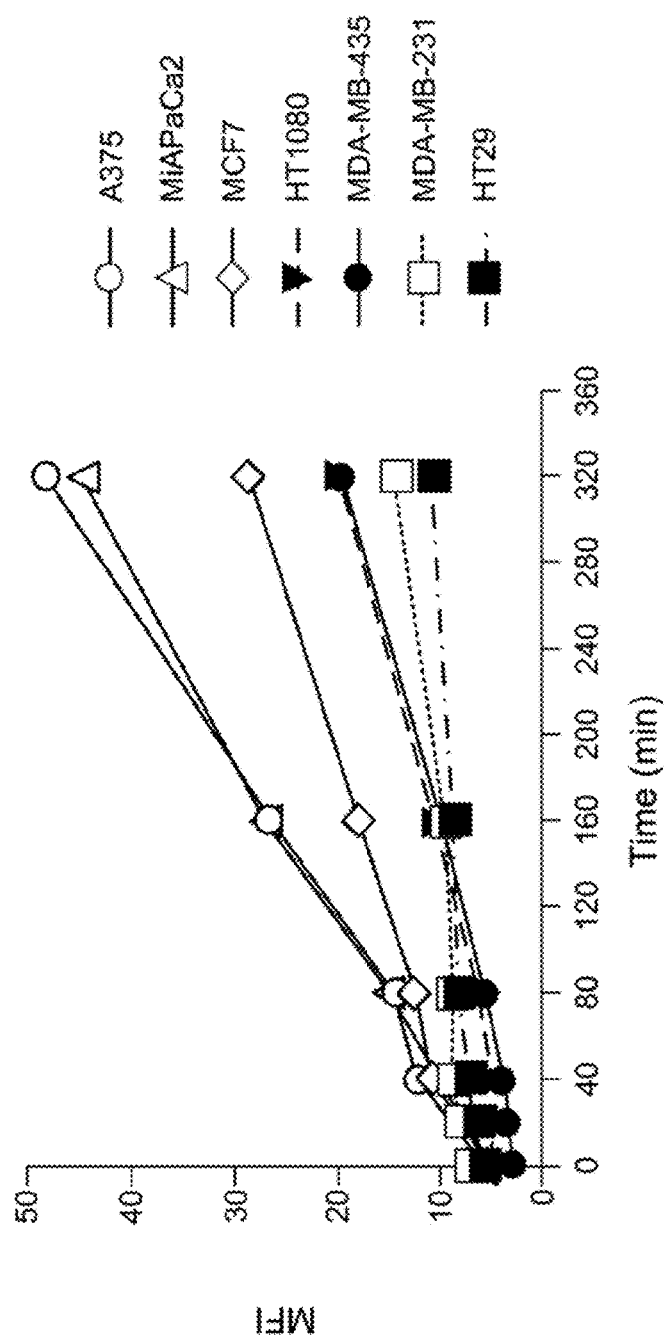
FIG. 9 shows time-dependent internalization of the FS24 antibody (FIG. 9A) and relative FN14 expression levels (FIG. 9B) by various cancer cell lines.
Figure 9B:
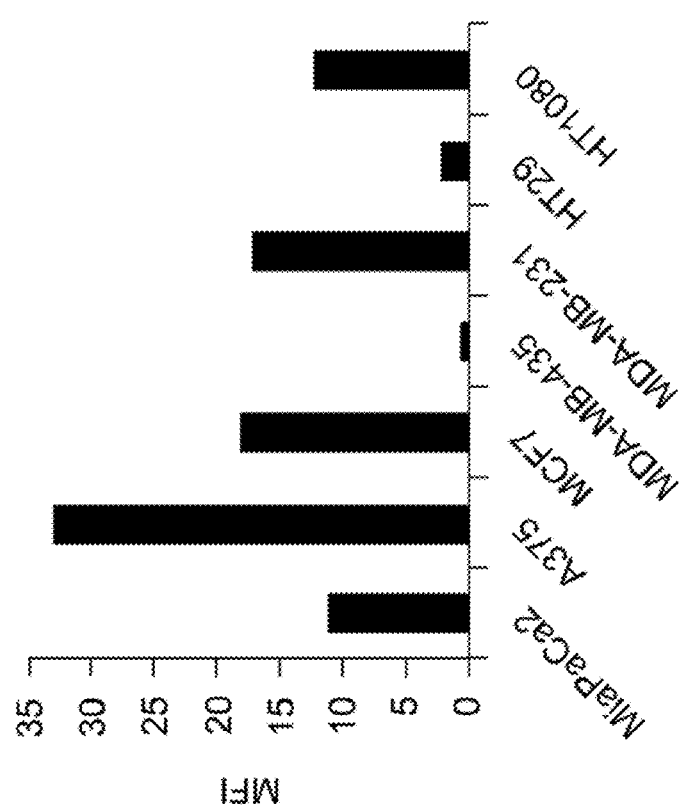

Internalization of cell surface receptors, initiated by antibody binding, is the basis of antibody-drug conjugate (ADC)-mediated cytotoxicity. To measure internalization of FN14-specific antibody FS24, this antibody was conjugated with AlexaFluor-488 (Invitrogen). The conjugate was added to the medium of cancer cell cultures in a 96-well plate and incubated for several hours at 37° C. At specific time points, cells were washed and dissociated. The cell surface fluorescence was then quenched with Anti-AlexaFluor488 (Invitrogen). Finally, the intracellular fluorescence, signifying accumulated FS24 conjugate, was measured by flow cytofluorimetry. Mean fluorescence intensity (MFI) for each time point was then plotted for each cell line (FIG. 9A). To determine relative levels of FN14 on the surfaces of the cell lines, cells were incubated with a saturating concentration (20 µg/ml) of FS24 or an isotype control antibody. Mean fluorescence intensity (MFI) was determined by flow cytofluorimetry, and relative levels were expressed as MFI of FS24 stained cells—MFI of isotype control (FIG. 9B).

As shown in FIG. 9A, there was considerable variability in the rate at which cells of distinct origins internalized the labeled antibody. The melanoma line, A375, and the pancreatic cancer line, MiaPaCa2, accumulated substantially more of the FS24-AlexaFluor488 over time than did HT1080, MDA-MB-435, or HT29 cells. MCF7 internalized an intermediate amount of antibody-conjugate. The internalization rate did not necessarily correlate with the cell surface levels of FN14. For example, while A374 cells expressed relatively high levels of FN14 on the cell surface (FIG. 9B) and also internalized high levels of the labeled antibody (FIG. 9A), MiaPaCa2 cells expressed only about 30% of the levels that were expressed by A375 cells (FIG. 9B) but accumulated labeled antibody internally at the same rate (FIG. 9A).

Example 5

FS24-Toxin Conjugated Antibody Killing of Cancer Cells

The ribosome-inactivating protein, saporin (molecular weight 30 kDa), is toxic to tumor cells when delivered by an antibody that is internalized (see e.g., Flavell, D. J. et al. *British J Cancer* 83, 1755-1761 (2000); Yip, W. L. et al. *Mol Pharmaceutics* 4, 241-251 (2007); Daniels, T. R. et al. *Mol Cancer Ther* 6, 2995-3008 (2007); Kuroda, K et al. *Prostate* 70, 1286-1294 (2010)). A chemical conjugate of streptavidin and saporin (Streptavidin-ZAP) was purchased from Advanced Targeting Systems (San Diego, Calif.). An FS24-saporin conjugate was generated by the following procedure: FS24 was biotinylated using EZ-Link Sulfo-NHS-LC-Biotinylation Kit (Thermo Fisher Scientific, Rockford, Ill.) in accordance with the manufacturer's instructions. Streptavidin-ZAP was linked to biotinylated FS24 by incubating the components at room temperature for 30 min at a 1:1 molar ratio. An isotype control was prepared by linking an irrelevant chimeric antibody to Streptavidin-ZAP in the same manner.

Figure 10A:
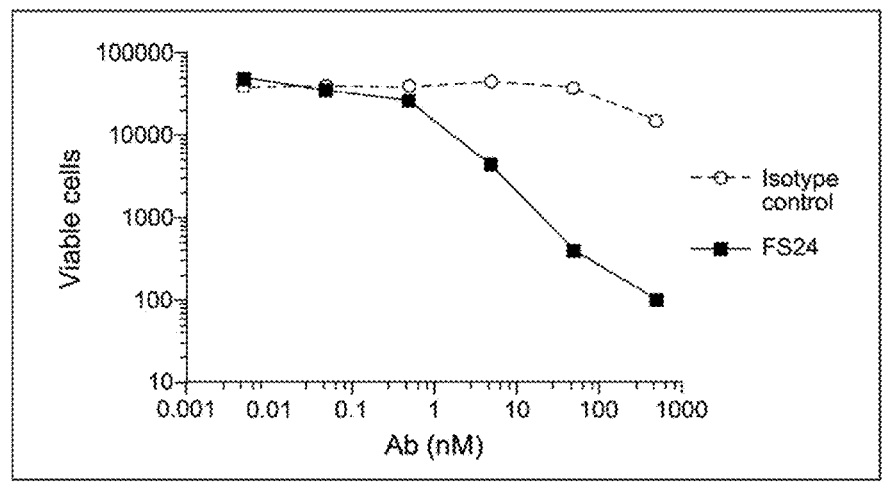
FIG. 10A shows a dose-dependent decrease in A375 melanoma cell viability in the presence of increasing concentrations of FS24-saporin conjugate; whereas an isotype-matched, irrelevant antibody conjugated to saporin did not affect cell viability.
Figure 10B:
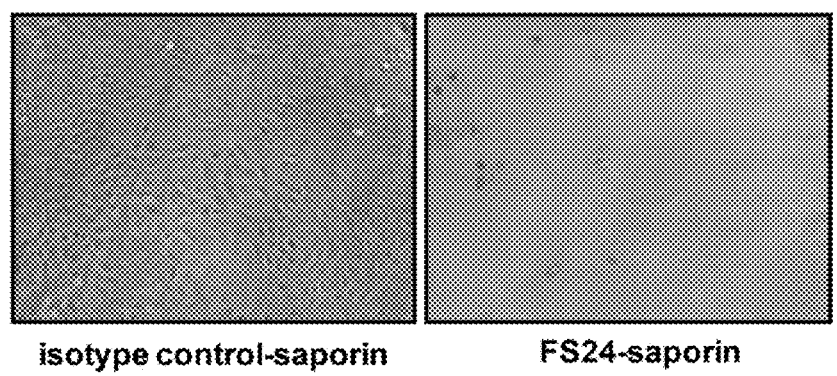
FIG. 10B is a light microscopy image of A375 cells exposed to 500 nM isotype control-saporin (left panel) or the FS24-saporin conjugate (right panel).
Figure 11A:
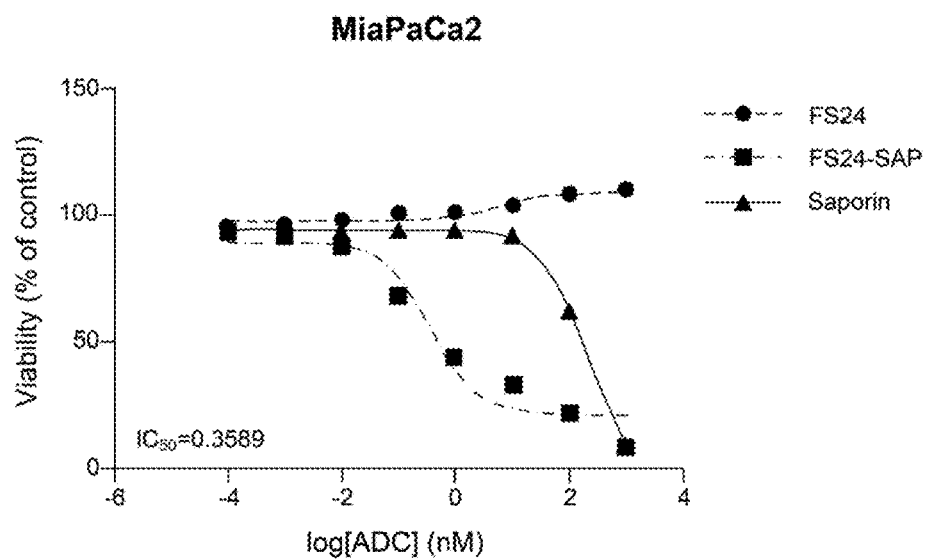
FIG. 11 shows variable FS24-toxin conjugate-mediated killing of twelve cancer cell lines. Changes in the viability of cells treated with either FS24-saporin or unconjugated saporin are shown. Cell lines were MiaPaCa2 (FIG. 11A), A375 (FIG. 11B), MCF7 (FIG. 11C), MDA-MB-435 (FIG. 11D), CaPan2 (FIG. 11E), SKOV-3 (FIG. 11F), HT29 (FIG. 11G), MDA-MB-231 (FIG. 11H), PC3 (FIG. 11I), HT1080 (FIG. 11J), BxPC-3 (FIG. 11K), and AsPC1 (FIG. 11L)
Figure 11B:
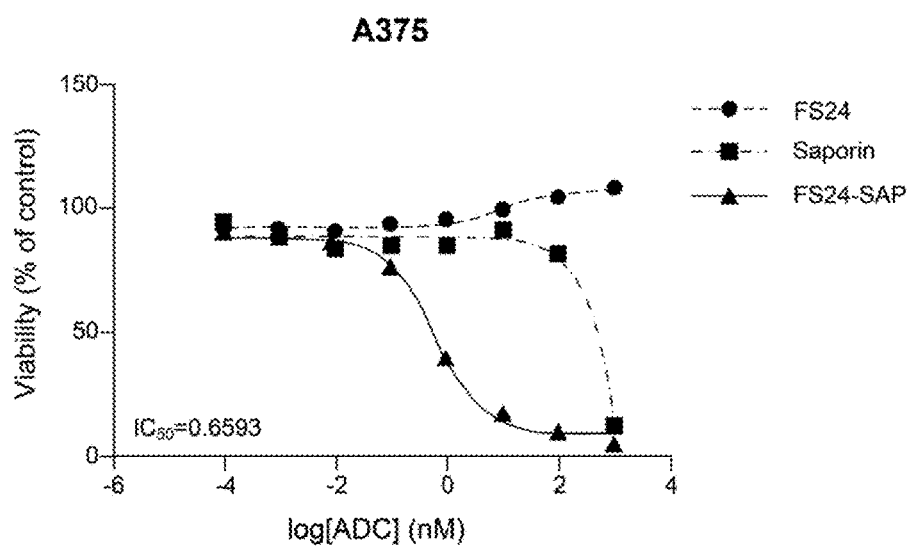
Figure 11C:
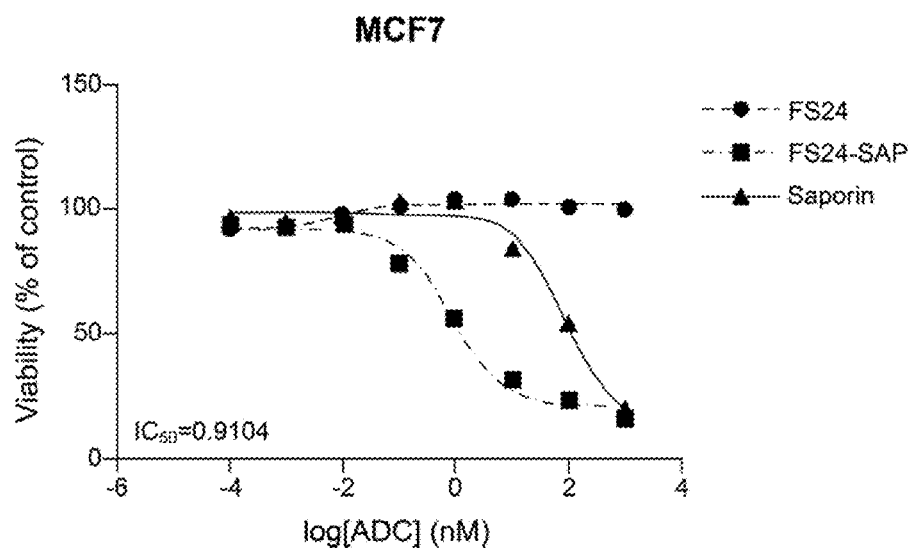
Figure 11D:
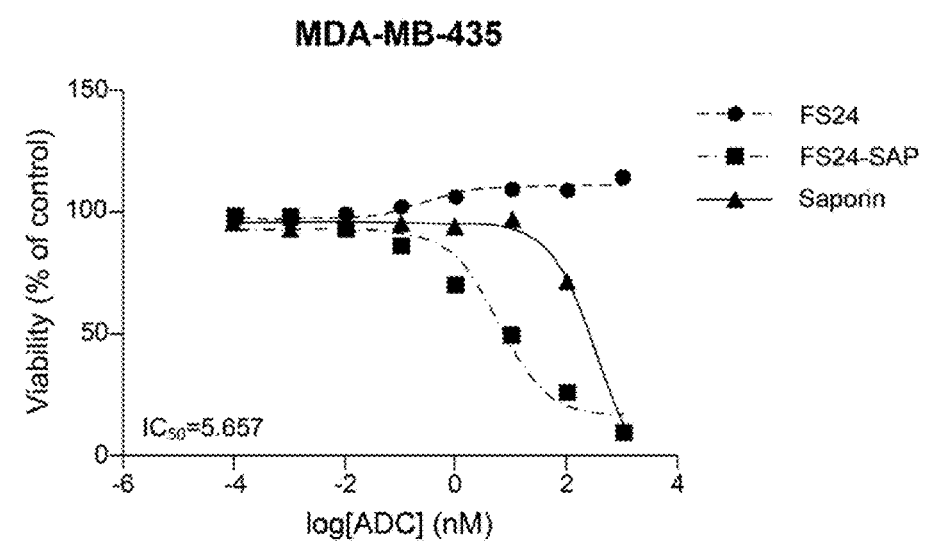
Figure 11E:
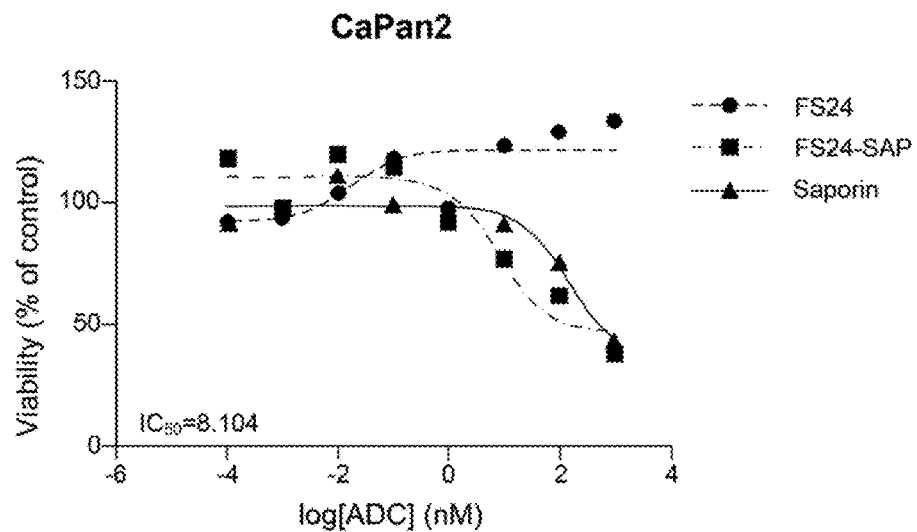
Figure 11F:
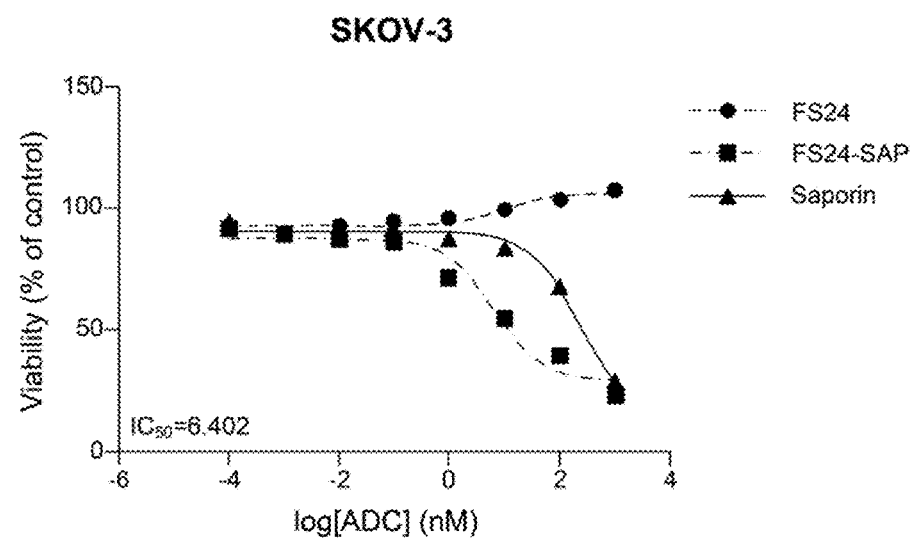
Figure 11G:
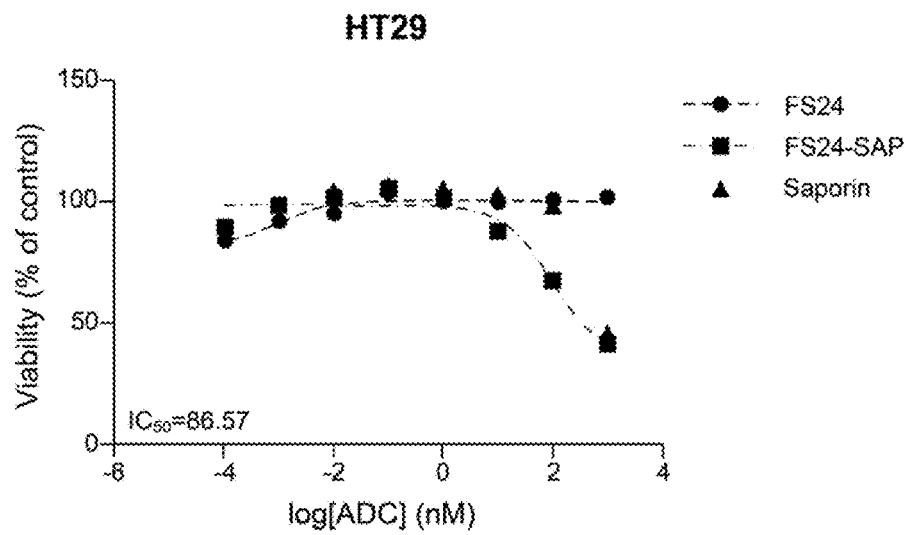
Figure 11H:
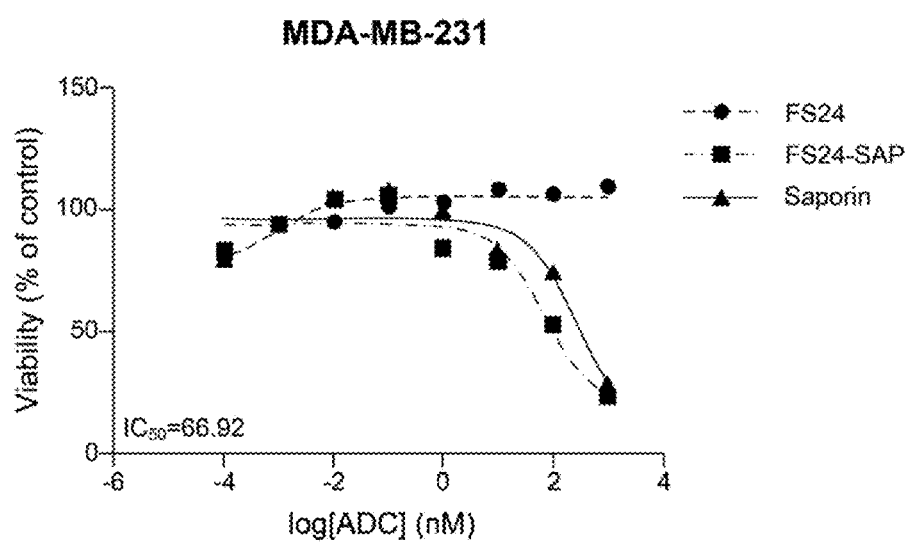
Figure 11I:
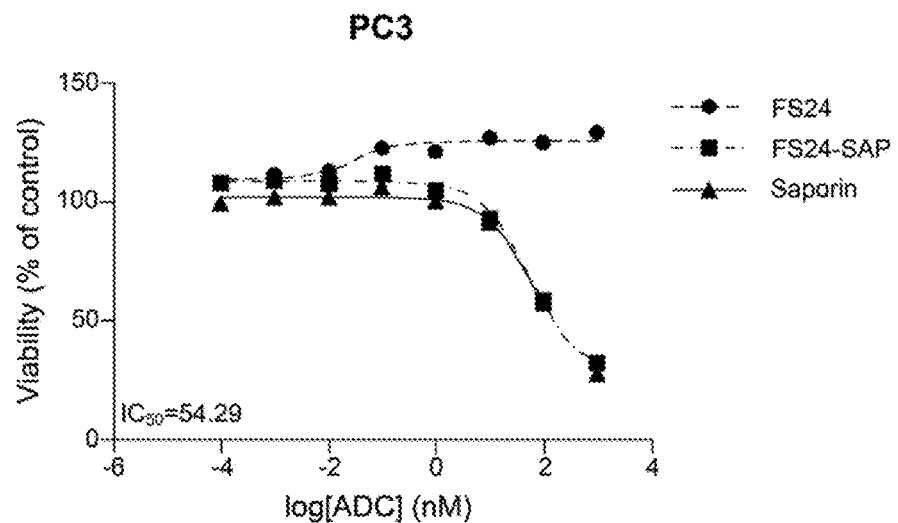
Figure 11J:
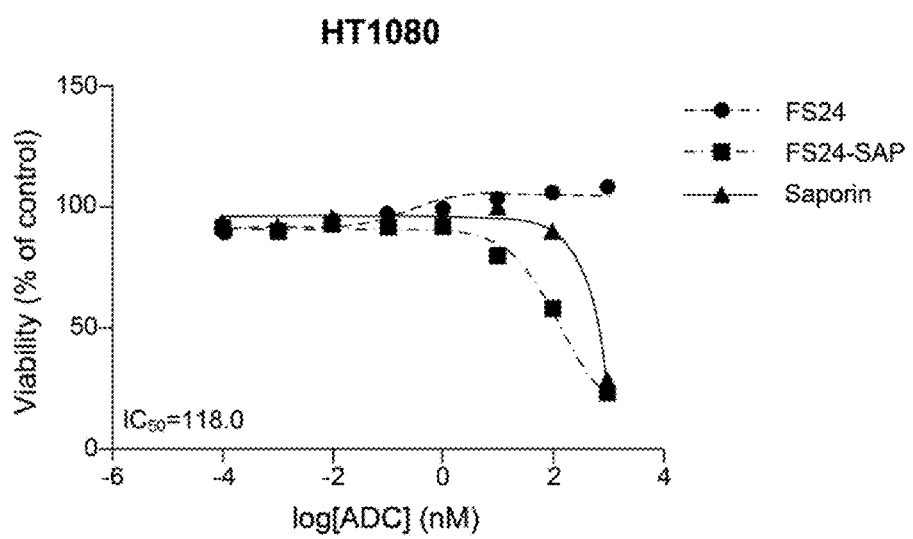
Figure 11K:
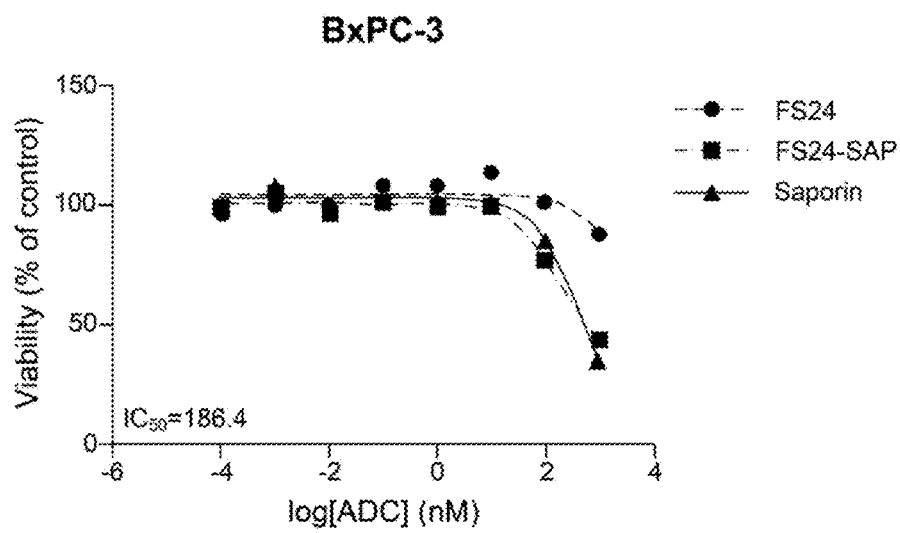
Figure 11L:
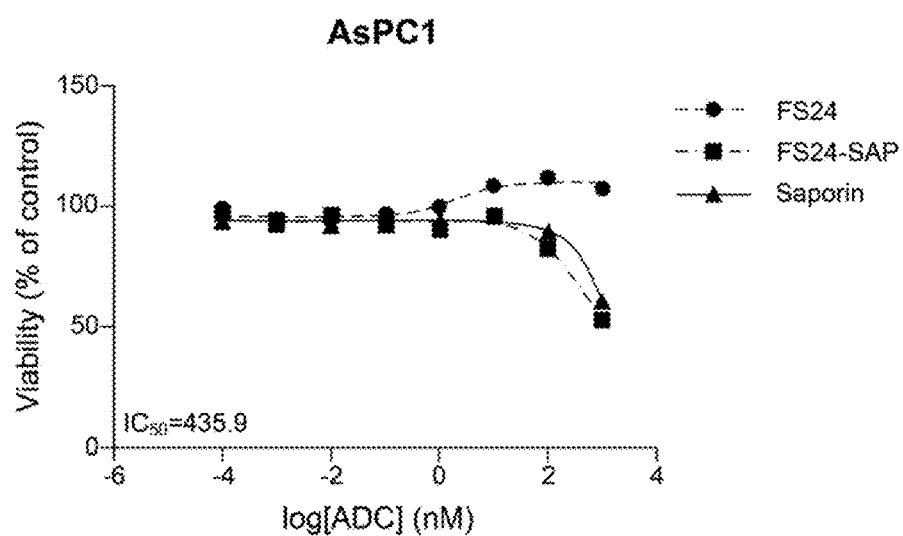

To test the specific toxicity of FS24-saporin, the FS24 or isotype control conjugates were added to A375 melanoma cells at varying concentrations and cell viability was determined. Briefly, 2500 cells were seeded into each well of a 96-well tissue culture plate. After an overnight incubation, the cells were washed twice with culture medium. Subsequently, concentrations of FS24- or isotype control-saporin ranging from 0.005 to 500 nM in culture medium were added into triplicate wells and the plate was incubated for 72 hours at 37° C., 5% $CO_2$. For a quantitative assessment of cell viability, surviving cells were released with dissociation buffer (Invitrogen, Carlsbad, Calif.) and counted in the presence of trypan blue dye. As shown in FIG. 10, FS24-saporin conjugate killed A375 melanoma cells in a dose-dependent manner, with an $IC_{50}$ of approximately 1 nM.

To further characterize ADC-mediated cell death by FS24, a direct chemical conjugate of antibody-saporin was generated (FS24-SAP; Advanced Targeting Systems). ADC-mediated cytotoxicity experiments were set up as above with twelve cancer cell lines (Table 4, FIG. 11) and FS24-SAP (1 µM to $1 \times 10^{-4}$ nM). After a 72-hour incubation, viability was determined with the CellTiter-Glo viability assay (Promega, Madison, Wis.), and $IC_{50}$ calculated with Prism (GraphPad; Table 4).

TABLE 4

Cytotoxic activity of FS24-SAP on cancer cell lines

| | $IC_{50}$ (nM) | |
|---|---|---|
| Cell line | FS24-SAP | Saporin |
| MiaPaCa2 | 0.3589 | 227.9 |
| A375 | 0.6593 | ~1.157e + 006 |
| MCF7 | 0.9104 | 83.6 |
| MDA-MB-435 | 5.657 | 389.1 |
| SKOV-3 | 6.402 | 216.9 |
| CaPan2 | 8.104 | 156.3 |
| PC3 | 54.29 | 72.34 |
| MDA-MB-231 | 66.92 | 267.8 |
| HT29 | 86.57 | NC |
| HT1080 | 118 | ~1.558e + 006 |
| BxPC-3 | 186.4 | 439.9 |
| AsPC1 | 435.9 | 6050 |
| MiaPaCa2 | 0.3589 | 227.9 |

As shown in FIG. 11, efficacy of FS24-SAP correlated well with internalization. For example, both internalization and ADC-mediated cytotoxicity were highest in MiaPaCa2 and A375 cells. Low nanomolar $IC_{50}$ values were also observed for MCF7, MDA-MB-435, SKOV-3, and CaPan2 cells.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated antibody, or an antigen-binding fragment thereof, that binds to human FN14, comprising:
   (a) a heavy chain variable region comprising the VHCDR1 amino acid sequence set forth in SEQ ID NO:79, and the VHCDR2 amino acid sequence set forth in SEQ ID NO:92 wherein Xaa at position 4 is Asp or Tyr and the VHCDR3 amino acid sequence set forth in SEQ ID NO:93, wherein Xaa at position 2 is Ala or Gly, Xaa at position 4 is Ser or Thr, and Xaa at position 5 is Ser or Gly; and
   (b) a light chain variable region comprising the VLCDR1 amino acid sequence set forth in SEQ ID NO:86, and the VLCDR2 amino acid sequence set forth in SEQ ID NO:39 and the VLCDR3 amino acid sequence set forth in SEQ ID NO:94,wherein Xaa at position 3 is Ala or Ile.

2. The isolated antibody of claim 1 wherein the VHCRD2 of the heavy chain variable region according to (a) comprises SEQ ID NO:82.

3. The isolated antibody of claim 1 wherein the VHCRD3 of the heavy chain variable region according to (a) comprises SEQ ID NO:84.

4. The isolated antibody of claim 1 wherein the VHCRD2 of the heavy chain variable region according to (a) comprises SEQ ID NO:81.

5. The isolated antibody of claim 1 wherein the VHCRD3 of the heavy chain variable region according to (a) comprises SEQ ID NO:83.

6. The isolated antibody of claim 1 wherein the VHCRD3 of the heavy chain variable region according to (a) comprises SEQ ID NO:76.

7. The isolated antibody of claim 1 wherein the VHCDR3 of the light chain variable region according to (b) comprises SEQ ID NO:41.

8. The isolated antibody of claim 1 wherein the VHCDR3 of the light chain variable region according to (b) comprises SEQ ID NO:36.

9. The isolated antibody of claim 1 wherein the heavy chain variable region comprises the amino acid sequence set forth in SEQ ID NO:67.

10. The isolated antibody of claim 1 wherein the light chain variable region comprises the amino acid sequence set forth in SEQ ID NO:25.

11. The isolated antibody of claim 1 wherein the heavy chain variable region comprises the amino acid sequence set forth in SEQ ID NO:66.

12. The isolated antibody of claim 1 wherein the antibody is humanized.

13. The isolated antibody, or antigen binding fragment thereof, of claim 12 wherein the light chain variable region comprises the amino acid sequence set forth in SEQ ID NO:91.

14. The isolated antibody, or antigen binding fragment thereof, of claim 12 wherein the heavy chain variable region comprises the amino acid set forth in SEQ ID NO:90.

15. The isolated antibody of claim 1 wherein the antibody is selected from the group consisting of a single chain antibody, a ScFv, a univalent antibody lacking a hinge region, and a minibody.

16. The isolated antibody of claim 1 wherein the antibody is selected from the group consisting of a Fab, a Fab' fragment, a F(ab')$_2$ fragment and a whole antibody.

17. The isolated antibody of claim 1 wherein the antibody is conjugated to a drug or a toxin.

18. The isolated antibody of claim 1 comprising a human IgG Fc domain.

19. The isolated antibody of claim 18 wherein the human IgG Fc domain is modified such that the antibody has enhanced .ADCC activity as compared to the antibody having the unmodified human IgG Fc domain.

20. An isolated antibody, or an antigen-binding fragment thereof, that binds to human FN14, comprising a heavy chain variable region comprising any one of the amino acid sequences set forth in SEQ ID NOs:67, 66 or 65.

21. The isolated antibody of claim 20 wherein the heavy chain variable region comprises the amino acid sequence set forth in SEQ ID NO:67 and wherein said antibody further comprises a light chain variable region comprising the amino acid sequence set forth in SEQ ID NO:25.

22. The isolated antibody of claim 20 wherein the heavy chain variable region comprises the amino acid sequence set forth in SEQ ID NO:66 and wherein said antibody further comprises a light chain variable region comprising the amino acid sequence set forth in SEQ ID NO:24.

23. The isolated antibody of claim 20 wherein the heavy chain variable region comprises the amino acid sequence set forth in SEQ ID NO:65 and wherein said antibody further comprises a light chain variable region comprising the amino acid sequence set forth in SEQ ID NO:23.

24. The isolated antibody of claim 20 wherein the antibody is selected from the group consisting of a single chain antibody, a ScFv, a univalent antibody lacking a hinge region, and a minibody.

25. The isolated antibody of claim 20 wherein the antibody is selected from the group consisting of a Fab, a Fab' fragment, a F(ab')$_2$ fragment and a whole antibody.

26. The isolated antibody of claim 20 wherein the antibody is conjugated to a drug or a toxin.

27. The isolated antibody of claim 20 comprising a human IgG Fc domain.

28. The isolated antibody of claim 27 wherein the human IgG Fc domain is modified such that the antibody has enhanced ADCC activity as compared to the antibody having the unmodified human IgG Fc domain.

29. An isolated antibody, or an antigen-binding fragment thereof, that binds to human FN14, comprising a light chain variable region comprising any one of the amino acid sequences set forth in SEQ ID NOs:25, 24 or 23.

30. The isolated antibody of claim 29 wherein the light chain variable region comprises SEQ ID NO:25 and wherein said antibody further comprises a heavy chain variable region comprising the amino acid sequence of SEQ ID NO:67.

31. The isolated antibody of claim 29 wherein the light chain variable region comprises SEQ ID NO:24 and wherein said antibody further comprises a heavy chain variable region comprising the amino acid sequence of SEQ ID NO:66.

32. The isolated antibody of claim 29 wherein the light chain variable region comprises SEQ ID NO:23 and wherein said antibody further comprises a heavy chain variable region comprising the amino acid sequence of SEQ ID NO:65.

33. The isolated antibody of claim 29 wherein the antibody is selected from the group consisting of a single chain antibody, a ScFv, a univalent antibody lacking a hinge region, and a minibody.

34. The isolated antibody of claim 29 Wherein the antibody is selected from the group consisting of a Fab, a Fab' fragment, a F(ab')$_2$ fragment and a whole antibody.

35. The isolated antibody of claim 29 wherein the antibody is conjugated to a drug or a toxin.

36. The isolated antibody of claim 29 comprising a human IgG Fc domain.

37. The isolated antibody of claim 36 wherein the human IgG Fc domain is modified such that the antibody has enhanced ADCC activity as compared to the antibody having the unmodified human IgG Fc domain.

38. A composition comprising a physiologically acceptable carrier and a therapeutically effective amount of the isolated antibody or antigen-binding fragment thereof according to claim 1.

* * * * *

SEQUENCE LISTING

<160> NUMBER OF SEQ ID NOS: 94

<210> SEQ ID NO 1
<211> LENGTH: 124
<212> TYPE: PRT
<213> ORGANISM: Gallus gallus

<400> SEQUENCE: 1

Val Thr Leu Asp Glu Ser Gly Gly Gly Leu Gln Thr Pro Gly Gly Ala
 1               5                   10                  15

Leu Ser Leu Val Cys Lys Ala Ser Gly Phe Thr Phe Ser Ser Asn Ala
            20                  25                  30

Met Gly Trp Val Arg Gln Ala Pro Gly Lys Gly Leu Glu Trp Val Ala
            35                  40                  45

Gly Ile Asp Asp Asp Gly Ser Gly Thr Arg Tyr Ala Pro Ala Val Lys
 50                  55                  60

Gly Arg Ala Thr Ile Ser Arg Asp Asn Gly Gln Ser Thr Leu Arg Leu
 65                  70                  75                  80

Gln Leu Asn Asn Leu Arg Ala Glu Asp Thr Gly Thr Tyr Tyr Cys Thr
            85                  90                  95

Lys Cys Ala Tyr Ser Ser Gly Cys Asp Tyr Glu Gly Tyr Ile Asp
            100                 105                 110

Ala Trp Gly His Gly Thr Glu Val Ile Val Ser Ser
            115                 120

<210> SEQ ID NO 2
<211> LENGTH: 124
<212> TYPE: PRT
<213> ORGANISM: Gallus gallus

<400> SEQUENCE: 2

Val Thr Leu Asp Glu Ser Gly Gly Gly Leu Gln Thr Pro Gly Gly Ala
 1               5                   10                  15

Leu Ser Leu Val Cys Lys Ala Ser Gly Phe Thr Phe Ser Ser Tyr Asp
            20                  25                  30

Met Ala Trp Val Arg Gln Glu Pro Gly Lys Gly Leu Glu Trp Val Ala
            35                  40                  45

Gly Ile Asp Asp Asp Gly Ser Gly Arg Arg Tyr Ala Pro Ala Val Lys
 50                  55                  60

Gly Arg Ala Thr Ile Ser Arg Asp Asn Gly Gln Ser Thr Leu Arg Leu
 65                  70                  75                  80

Gln Leu Asn Asn Leu Arg Ala Glu Asp Thr Gly Thr Tyr Tyr Cys Thr
            85                  90                  95

Lys Cys Ala Tyr Ser Ser Gly Cys Asp Tyr Glu Gly Tyr Ile Asp
            100                 105                 110

Ala Trp Gly His Gly Thr Glu Val Ile Val Ser Ser
            115                 120

<210> SEQ ID NO 3
<211> LENGTH: 124
<212> TYPE: PRT
<213> ORGANISM: Gallus gallus

<400> SEQUENCE: 3

Val Thr Leu Asp Glu Ser Gly Gly Gly Leu Gln Thr Pro Gly Gly Ala
 1               5                   10                  15

Leu Ser Leu Val Cys Lys Ala Ser Gly Phe Thr Phe Ser Ser Tyr Asp
            20                  25                  30

Met Ala Trp Val Arg Gln Glu Pro Gly Lys Gly Leu Glu Trp Val Ala
            35                  40                  45

Gly Ile Asp Asp Asp Gly Ser Gly Arg Arg Tyr Ala Pro Ala Val Lys
 50                  55                  60

Gly Arg Ala Thr Ile Ser Arg Asp Asn Gly Gln Ser Thr Leu Arg Leu
 65                  70                  75                  80

Gln Leu Asn Asn Leu Arg Ala Glu Asp Thr Gly Thr Tyr Tyr Cys Thr
            85                  90                  95

```
Lys Cys Ala Tyr Thr Gly Gly Cys Asp Tyr Glu Gly Tyr Ile Asp
            100                 105                 110
Ala Trp Gly His Gly Thr Glu Val Ile Val Ser Ser
            115                 120
```

<210> SEQ ID NO 4
<211> LENGTH: 124
<212> TYPE: PRT
<213> ORGANISM: Gallus gallus

<400> SEQUENCE: 4

```
Val Thr Leu Asp Glu Ser Gly Gly Leu Gln Thr Pro Gly Gly Ala
 1               5                  10                  15
Leu Ser Leu Val Cys Lys Ala Ser Gly Phe Thr Phe Ser Ser Tyr Asp
                20                  25                  30
Met Ala Trp Val Arg Gln Glu Pro Gly Lys Gly Leu Glu Trp Val Ala
            35                  40                  45
Gly Ile Asp Tyr Asp Gly Ser Gly Arg Arg Tyr Ala Pro Ala Val Lys
        50                  55                  60
Gly Arg Ala Thr Ile Ser Arg Asp Asn Gly Gln Ser Thr Leu Arg Leu
65                  70                  75                  80
Gln Leu Asn Asn Leu Arg Ala Glu Asp Thr Gly Thr Tyr Tyr Cys Thr
                85                  90                  95
Lys Cys Gly Tyr Thr Gly Gly Cys Asp Tyr Glu Gly Tyr Ile Asp
            100                 105                 110
Ala Trp Gly His Gly Thr Glu Val Ile Val Ser Ser
            115                 120
```

<210> SEQ ID NO 5
<211> LENGTH: 124
<212> TYPE: PRT
<213> ORGANISM: Gallus gallus

<400> SEQUENCE: 5

```
Val Thr Leu Asp Glu Ser Gly Gly Leu Gln Thr Pro Gly Gly Ala
 1               5                  10                  15
Leu Ser Leu Val Cys Lys Ala Ser Gly Phe Thr Phe Ser Ser Tyr Asp
                20                  25                  30
Met Phe Trp Val Arg Gln Glu Pro Gly Lys Gly Leu Glu Trp Val Ala
            35                  40                  45
Gly Ile Asp Asp Asp Gly Ser Gly Arg Arg Tyr Ala Pro Ala Val Lys
        50                  55                  60
Gly Arg Ala Thr Ile Ser Arg Asp Asn Gly Gln Ser Thr Leu Arg Leu
65                  70                  75                  80
Gln Leu Asn Asn Leu Arg Ala Glu Asp Thr Gly Thr Tyr Tyr Cys Thr
                85                  90                  95
Lys Cys Ala Tyr Ser Ser Gly Cys Asp Tyr Glu Gly Tyr Ile Asp
            100                 105                 110
Ala Trp Gly His Gly Thr Glu Val Ile Val Ser Ser
            115                 120
```

<210> SEQ ID NO 6
<211> LENGTH: 372
<212> TYPE: DNA
<213> ORGANISM: Gallus gallus

<400> SEQUENCE: 6

```
gtgacgttgg acgagtccgg gggcggcctc cagacgcccg ggggagcgct cagcctcgtc      60
```

```
tgcaaggcct ccgggttcac cttcagcagt aacgccatgg gttgggtgcg acaggcgccc    120
ggcaaggggc tggagtgggt cgctggtatt gatgatgatg gtagtggcac aagatacgcg    180
ccggcggtga agggccgtgc caccatctcg agggacaacg ggcagagcac actgaggctg    240
cagctgaaca acctcagggc tgaggacacc ggcacctact actgcacgaa atgtgcttac    300
agtagtggtt gtgattatga aggtggttat atcgacgcat ggggccacgg gaccgaagtc    360
atcgtctcct cc                                                         372

<210> SEQ ID NO 7
<211> LENGTH: 372
<212> TYPE: DNA
<213> ORGANISM: Gallus gallus

<400> SEQUENCE: 7
gtgacgttgg acgagtccgg gggcggcctc cagacgcccg ggggagcgct cagcctcgtc    60
tgcaaggcct ccgggttcac cttcagcagt tacgacatgg cctgggtgcg acaggagccc    120
ggcaaggggc tggagtgggt cgctggtatt gatgatgatg gtagtggcag aagatacgcg    180
ccggcggtga agggccgtgc caccatctcg agggacaacg ggcagagcac actgaggctg    240
cagctgaaca acctcagggc tgaggacacc ggcacctatt actgcacgaa atgtgcttac    300
agtagtggtt gtgattatga aggtggttat atcgacgcat ggggccacgg gaccgaagtc    360
atcgtctcct cc                                                         372

<210> SEQ ID NO 8
<211> LENGTH: 372
<212> TYPE: DNA
<213> ORGANISM: Gallus gallus

<400> SEQUENCE: 8
gtgacgttgg acgagtccgg gggcggcctc cagacgcccg ggggagcgct cagcctcgtc    60
tgcaaggcct ccgggttcac cttcagcagt tacgacatgg cctgggtgcg acaggagccc    120
ggcaaggggc tggagtgggt cgctggtatt gatgatgatg gtagtggcag aagatacgcg    180
ccggcggtga agggccgtgc caccatctcg agggacaacg ggcagagcac actgaggctg    240
cagctgaaca acctcagggc tgaggacacc ggcacctatt actgcacgaa atgtgcttac    300
actggtggtt gtgattatga aggtggttat atcgacgcat ggggccacgg gaccgaagtc    360
atcgtctcct cc                                                         372

<210> SEQ ID NO 9
<211> LENGTH: 372
<212> TYPE: DNA
<213> ORGANISM: Gallus gallus

<400> SEQUENCE: 9
gtgacgttgg acgagtccgg gggcggcctc cagacgcccg ggggagcgct cagcctcgtc    60
tgcaaggcct ccgggttcac cttcagcagt tacgacatgg cctgggtgcg acaggagccc    120
ggcaaggggc tggagtgggt cgctggtatt gattatgatg gtagtggcag aagatacgcg    180
ccggcggtga agggccgtgc caccatctcg agggacaacg ggcagagcac actgaggctg    240
cagctgaaca acctcagggc tgaggacacc ggcacctatt actgcacgaa atgtggttac    300
actggtggtt gtgattatga aggtggttat atcgacgcat ggggccacgg gaccgaagtc    360
atcgtctcct cc                                                         372

<210> SEQ ID NO 10
```

```
<211> LENGTH: 372
<212> TYPE: DNA
<213> ORGANISM: Gallus gallus

<400> SEQUENCE: 10
gtgacgttgg acgagtccgg gggcggcctc cagacgcccg ggggagcgct cagcctcgtc      60
tgcaaggcct ccgggttcac cttcagcagt tacgacatgt tctgggtgcg acaggagccc     120
ggcaaggggc tggagtgggt cgctggtatt gatgatgatg gtagtggcag aagatacgcg     180
ccggcggtga agggccgtgc caccatctcg agggacaacg gcagagcac actgaggctg      240 cagctgaaca acctcaggc tgaggacacc ggcacctatt actgcacgaa atgtgcttac      300
agtagtggtt gtgattatga aggtggttat atcgacgcat ggggccacgg gaccgaagtc     360
atcgtctcct cc                                                         372

<210> SEQ ID NO 11
<211> LENGTH: 6
<212> TYPE: PRT
<213> ORGANISM: Gallus gallus

<400> SEQUENCE: 11

Ser Ser Asn Ala Met Gly
1               5

<210> SEQ ID NO 12
<211> LENGTH: 16
<212> TYPE: PRT
<213> ORGANISM: Gallus gallus

<400> SEQUENCE: 12

Gly Ile Asp Asp Asp Gly Ser Gly Thr Arg Tyr Ala Pro Ala Val Lys
1               5                   10                  15

<210> SEQ ID NO 13
<211> LENGTH: 15
<212> TYPE: PRT
<213> ORGANISM: Gallus gallus

<400> SEQUENCE: 13

Thr Lys Cys Ala Tyr Ser Ser Gly Cys Asp Tyr Glu Gly Gly Tyr
1               5                   10                  15

<210> SEQ ID NO 14
<211> LENGTH: 6
<212> TYPE: PRT
<213> ORGANISM: Gallus gallus

<400> SEQUENCE: 14

Ser Ser Tyr Asp Met Phe
1               5

<210> SEQ ID NO 15
<211> LENGTH: 11
<212> TYPE: PRT
<213> ORGANISM: Gallus gallus

<400> SEQUENCE: 15

Ser Ser Tyr Asp Met Phe Trp Val Arg Gln Glu
1               5                   10

<210> SEQ ID NO 16
<211> LENGTH: 6
<212> TYPE: PRT
<213> ORGANISM: Gallus gallus
```

```
<400> SEQUENCE: 16

Ser Ser Tyr Asp Met Ala
1               5

<210> SEQ ID NO 17
<211> LENGTH: 11
<212> TYPE: PRT
<213> ORGANISM: Gallus gallus

<400> SEQUENCE: 17

Ser Ser Tyr Asp Met Ala Trp Val Arg Gln Glu
1               5                   10

<210> SEQ ID NO 18
<211> LENGTH: 16
<212> TYPE: PRT
<213> ORGANISM: Gallus gallus

<400> SEQUENCE: 18

Gly Ile Asp Asp Asp Gly Ser Gly Arg Arg Tyr Ala Pro Ala Val Lys
1               5                   10                  15

<210> SEQ ID NO 19
<211> LENGTH: 16
<212> TYPE: PRT
<213> ORGANISM: Gallus gallus

<400> SEQUENCE: 19

Gly Ile Asp Tyr Asp Gly Ser Gly Arg Arg Tyr Ala Pro Ala Val Lys
1               5                   10                  15

<210> SEQ ID NO 20
<211> LENGTH: 15
<212> TYPE: PRT
<213> ORGANISM: Gallus gallus

<400> SEQUENCE: 20

Thr Lys Cys Ala Tyr Thr Gly Gly Cys Asp Tyr Glu Gly Gly Tyr
1               5                   10                  15

<210> SEQ ID NO 21
<211> LENGTH: 15
<212> TYPE: PRT
<213> ORGANISM: Gallus gallus

<400> SEQUENCE: 21

Thr Lys Cys Gly Tyr Thr Gly Gly Cys Asp Tyr Glu Gly Gly Tyr
1               5                   10                  15

<210> SEQ ID NO 22
<211> LENGTH: 107
<212> TYPE: PRT
<213> ORGANISM: Gallus gallus

<400> SEQUENCE: 22

Ala Leu Thr Gln Pro Ala Ser Val Ser Ala Asn Leu Gly Gly Thr Val
1               5                   10                  15

Lys Ile Thr Cys Ser Gly Gly Gly Ser Tyr Ala Gly Ser Tyr Tyr Tyr
                20                  25                  30

Gly Trp Tyr Gln Gln Lys Ser Pro Gly Ser Ala Pro Val Thr Val Ile
        35                  40                  45

Tyr Asp Asn Asp Lys Arg Pro Ser Asp Ile Pro Ser Arg Phe Ser Gly
    50                  55                  60
```

Ser Leu Ser Gly Ser Thr Asn Thr Leu Thr Ile Thr Gly Val Arg Ala
65                  70                  75                  80

Asp Asp Glu Ala Val Tyr Phe Cys Gly Ser Ala Asp Asn Ser Gly Ala
                85                  90                  95

Ala Phe Gly Ala Gly Thr Thr Leu Thr Val Leu
            100                 105

<210> SEQ ID NO 23
<211> LENGTH: 109
<212> TYPE: PRT
<213> ORGANISM: Gallus gallus

<400> SEQUENCE: 23

Ala Leu Thr Gln Pro Ala Ser Val Ser Ala Asn Pro Gly Glu Thr Val
1               5                   10                  15

Lys Ile Thr Cys Ser Gly Gly Gly Ser Ser Tyr Tyr Ala Gly Ser Tyr
                20                  25                  30

Tyr Tyr Gly Trp Tyr Gln Gln Lys Ala Pro Gly Ser Ala Leu Val Thr
            35                  40                  45

Leu Ile Tyr Tyr Asn Asn Lys Arg Pro Ser Asp Ile Pro Ser Arg Phe
50                  55                  60

Ser Gly Ser Leu Ser Gly Ser Thr Asn Thr Leu Thr Ile Thr Gly Val
65                  70                  75                  80

Arg Ala Asp Asp Glu Ala Val Tyr Phe Cys Gly Ser Ala Asp Asn Ser
                85                  90                  95

Gly Ala Ala Phe Gly Ala Gly Thr Thr Leu Thr Val Leu
            100                 105

<210> SEQ ID NO 24
<211> LENGTH: 109
<212> TYPE: PRT
<213> ORGANISM: Gallus gallus

<400> SEQUENCE: 24

Ala Leu Thr Gln Pro Ala Ser Val Ser Ala Asn Pro Gly Glu Thr Val
1               5                   10                  15

Lys Ile Thr Cys Ser Gly Gly Gly Ser Ser Tyr Tyr Ala Gly Ser Tyr
                20                  25                  30

Tyr Tyr Gly Trp Tyr Gln Gln Lys Ala Pro Gly Ser Ala Pro Val Thr
            35                  40                  45

Leu Ile Tyr Tyr Asn Asn Lys Arg Pro Ser Asp Ile Pro Ser Arg Phe
50                  55                  60

Ser Gly Ser Leu Ser Gly Ser Thr Asn Thr Leu Thr Ile Thr Gly Val
65                  70                  75                  80

Arg Ala Asp Asp Glu Ala Val Tyr Phe Cys Gly Ser Ile Asp Asn Ser
                85                  90                  95

Gly Ala Ala Phe Gly Ala Gly Thr Thr Leu Thr Val Leu
            100                 105

<210> SEQ ID NO 25
<211> LENGTH: 109
<212> TYPE: PRT
<213> ORGANISM: Gallus gallus

<400> SEQUENCE: 25

Ala Leu Thr Gln Pro Ser Ser Val Ser Ala Asn Pro Gly Glu Thr Val
1               5                   10                  15

Lys Ile Thr Cys Ser Gly Gly Gly Ser Ser Tyr Tyr Ala Gly Ser Tyr

```
                    20                  25                  30
Tyr Tyr Gly Trp Tyr Gln Gln Lys Ala Pro Gly Ser Ala Pro Val Thr
            35                  40                  45

Leu Ile Tyr Tyr Asn Asn Lys Arg Pro Ser Asp Ile Pro Ser Arg Phe
        50                  55                  60

Ser Gly Ser Leu Ser Gly Ser Thr Asn Thr Leu Thr Ile Thr Gly Val
65                  70                  75                  80

Arg Ala Asp Asp Glu Ala Val Tyr Phe Cys Gly Ser Ile Asp Asn Ser
                85                  90                  95

Gly Ala Ala Phe Gly Ala Gly Thr Thr Leu Thr Val Leu
            100                 105

<210> SEQ ID NO 26
<211> LENGTH: 109
<212> TYPE: PRT
<213> ORGANISM: Gallus gallus

<400> SEQUENCE: 26

Ala Leu Thr Gln Pro Ala Ser Val Ser Ala Asn Pro Gly Glu Thr Val
1               5                   10                  15

Lys Ile Thr Cys Ser Gly Gly Ser Ser Tyr Tyr Ala Gly Ser Tyr
            20                  25                  30

Tyr Tyr Gly Trp Tyr Gln Gln Lys Ser Pro Gly Ser Ala Pro Val Thr
            35                  40                  45

Val Ile Tyr Tyr Asn Asn Lys Arg Pro Ser Asp Ile Pro Ser Arg Phe
        50                  55                  60

Ser Gly Ser Leu Ser Gly Ser Thr Asn Thr Leu Thr Ile Thr Gly Val
65                  70                  75                  80

Arg Ala Asp Asp Glu Ala Val Tyr Phe Cys Gly Ser Ile Asp Asn Ser
                85                  90                  95

Gly Ala Ala Phe Gly Ala Gly Thr Thr Leu Thr Val Leu
            100                 105

<210> SEQ ID NO 27
<211> LENGTH: 109
<212> TYPE: PRT
<213> ORGANISM: Gallus gallus

<400> SEQUENCE: 27

Ala Leu Thr Gln Pro Ser Ser Val Ser Ala Asn Pro Gly Glu Thr Val
1               5                   10                  15

Lys Ile Thr Cys Ser Gly Gly Ser Ser Tyr Tyr Ala Gly Ser Tyr
            20                  25                  30

Tyr Tyr Gly Trp Tyr Gln Gln Lys Ala Pro Gly Ser Ala Pro Val Thr
            35                  40                  45

Leu Ile Tyr Tyr Asn Asn Lys Arg Pro Ser Asp Ile Pro Ser Arg Phe
        50                  55                  60

Ser Gly Ser Leu Ser Gly Ser Thr Asn Thr Leu Thr Ile Thr Gly Val
65                  70                  75                  80

Arg Ala Asp Asp Glu Ala Val Tyr Phe Cys Gly Ser Ile Asp Asn Ser
                85                  90                  95

Gly Ala Ala Phe Gly Ala Gly Thr Thr Leu Thr Val Leu
            100                 105

<210> SEQ ID NO 28
<211> LENGTH: 322
<212> TYPE: DNA
<213> ORGANISM: Gallus gallus
```

```
<400> SEQUENCE: 28
gcgctgactc agccggcctc ggtgtcagca aacctgggag gaaccgtcaa gatcacctgc      60 tccggggggtg gcagctatgc tggaagttac tattatggct ggtaccagca gaagtctcct    120
ggcagtgccc ctgtcactgt gatctatgac aacgacaaga gaccctcgga catcccttca    180
cgattctccg gttccctatc cggctccaca aacacattaa ccatcactgg ggtccgagcc    240
gatgacgagg ctgtctattt ctgtgggagt gcagacaaca gtggtgctgc atttggggcc    300
gggacaaccc tgaccgtcct ag                                              322

<210> SEQ ID NO 29
<211> LENGTH: 328
<212> TYPE: DNA
<213> ORGANISM: Gallus gallus

<400> SEQUENCE: 29
gcgctgactc agccggcctc ggtgtcagca aacccaggag aaaccgtcaa gatcacctgc      60 tccggggggtg gtagcagcta ctatgctgga agttactatt atggctggta ccagcagaag    120
gcacctggca gtgcccttgt cactctgatc tattacaaca caagagacc ctcggacatc     180 ccttcacgat tctccggttc cctatccggc tccacaaaca cattaaccat cactggggtc    240
cgagccgatg acgaggctgt ctatttctgt gggagtgcag acaacagtgg tgctgcattt    300
ggggccggga caaccctgac cgtcctag                                        328

<210> SEQ ID NO 30
<211> LENGTH: 328
<212> TYPE: DNA
<213> ORGANISM: Gallus gallus

<400> SEQUENCE: 30
gcgctgactc agccggcctc ggtgtcagca aacccaggag aaaccgtcaa gatcacctgc      60 tccggggggtg gtagcagcta ctatgctgga agttactatt atggctggta ccagcagaag    120
gcacctggca gtgcccctgt cactctgatc tattacaaca caagagacc ctcggacatc     180 ccttcacgat tctccggttc cctatccggc tccacaaaca cattaaccat cactggggtc    240
cgagccgatg acgaggctgt ctatttctgt gggagcatag acaacagtgg tgctgcattt    300
ggggccggga caaccctgac cgtcctag                                        328

<210> SEQ ID NO 31
<211> LENGTH: 328
<212> TYPE: DNA
<213> ORGANISM: Gallus gallus

<400> SEQUENCE: 31
gcgctgactc agccgtcctc ggtgtcagca aacccaggag aaaccgtcaa gatcacctgc      60 tccggggggtg gtagcagcta ctatgctgga agttactatt atggctggta ccagcagaag    120
gcacctggca gtgcccctgt cactctgatc tattacaaca caagagacc ctcggacatc     180 ccttcacgat tctccggttc cctatccggc tccacaaaca cattaaccat cactggggtc    240
cgagccgatg acgaggctgt ctatttctgt gggagcatag acaacagtgg tgctgcattt    300
ggggccggga caaccctgac cgtcctag                                        328

<210> SEQ ID NO 32
<211> LENGTH: 328
<212> TYPE: DNA
<213> ORGANISM: Gallus gallus
```

<400> SEQUENCE: 32

```
gcgctgactc agccggcctc ggtgtcagca aacccaggag aaaccgtcaa gatcacctgc      60
tccgggggtg gtagcagcta ctatgctgga agttactatt atggctggta tcagcagaag     120
tcacctggca gtgcccctgt cactgtgatc tattacaaca acaagagacc ctcggacatc     180
ccttcacgat tctccggttc cctatccggc tccacaaaca cattaaccat cactggggtc     240
cgagccgatg acgaggctgt ctatttctgt gggagcatag acaacagtgg tgctgcattt     300
ggggccggga caaccctgac cgtcctag                                        328
```

<210> SEQ ID NO 33
<211> LENGTH: 328
<212> TYPE: DNA
<213> ORGANISM: Gallus gallus

<400> SEQUENCE: 33

```
gcgctgactc agccgtcctc ggtgtcagca aacccaggag aaaccgtcaa gatcacctgc      60
tccgggggtg gtagcagcta ctatgctgga agttactatt atggctggta ccagcagaag     120
gcacctggca gtgcccctgt cactctgatc tattacaaca acaagagacc ctcggacatc     180
ccttcacgat tctccggttc cctatccggc tccacaaaca cattaaccat cactggggtc     240
cgagccgatg acgaggctgt ctatttctgt gggagcatag acaacagtgg tgctgcattt     300
ggggccggga caaccctgac cgtcctag                                        328
```

<210> SEQ ID NO 34
<211> LENGTH: 12
<212> TYPE: PRT
<213> ORGANISM: Gallus gallus

<400> SEQUENCE: 34

```
Gly Gly Gly Ser Tyr Ala Gly Ser Tyr Tyr Tyr Gly
 1               5                  10
```

<210> SEQ ID NO 35
<211> LENGTH: 7
<212> TYPE: PRT
<213> ORGANISM: Gallus gallus

<400> SEQUENCE: 35

```
Asp Asn Asp Lys Arg Pro Ser
 1               5
```

<210> SEQ ID NO 36
<211> LENGTH: 9
<212> TYPE: PRT
<213> ORGANISM: Gallus gallus

<400> SEQUENCE: 36

```
Gly Ser Ala Asp Asn Ser Gly Ala Ala
 1               5
```

<210> SEQ ID NO 37
<211> LENGTH: 14
<212> TYPE: PRT
<213> ORGANISM: Gallus gallus

<400> SEQUENCE: 37

```
Gly Gly Gly Ser Ser Tyr Tyr Ala Gly Ser Tyr Tyr Tyr Gly
 1               5                  10
```

-continued

<210> SEQ ID NO 38
<211> LENGTH: 24
<212> TYPE: PRT
<213> ORGANISM: Gallus gallus

<400> SEQUENCE: 38

Pro Gly Glu Thr Val Lys Ile Thr Cys Ser Gly Gly Ser Ser Tyr
1               5                   10                  15

Tyr Ala Gly Ser Tyr Tyr Tyr Gly
            20

<210> SEQ ID NO 39
<211> LENGTH: 7
<212> TYPE: PRT
<213> ORGANISM: Gallus gallus

<400> SEQUENCE: 39

Tyr Asn Asn Lys Arg Pro Ser
1               5

<210> SEQ ID NO 40
<211> LENGTH: 18
<212> TYPE: PRT
<213> ORGANISM: Gallus gallus

<400> SEQUENCE: 40

Ala Pro Gly Ser Ala Pro Val Thr Leu Ile Tyr Tyr Asn Asn Lys Arg
1               5                   10                  15

Pro Ser

<210> SEQ ID NO 41
<211> LENGTH: 9
<212> TYPE: PRT
<213> ORGANISM: Gallus gallus

<400> SEQUENCE: 41

Gly Ser Ile Asp Asn Ser Gly Ala Ala
1               5

<210> SEQ ID NO 42
<211> LENGTH: 214
<212> TYPE: PRT
<213> ORGANISM: Artificial Sequence
<220> FEATURE:
<223> OTHER INFORMATION: Humanized PS4 light chain sequence

<400> SEQUENCE: 42

Ala Leu Thr Gln Pro Pro Ser Val Ser Val Ser Pro Gly Gln Thr Ala
1               5                   10                  15

Arg Ile Thr Cys Ser Gly Gly Ser Ser Tyr Tyr Ala Gly Ser Tyr
            20                  25                  30

Tyr Tyr Gly Trp Tyr Gln Gln Lys Pro Gly Gln Ala Pro Val Thr Val
        35                  40                  45

Ile Tyr Tyr Asn Asn Lys Arg Pro Ser Gly Ile Pro Glu Arg Phe Ser
    50                  55                  60

Gly Ser Leu Ser Gly Ser Thr Asn Thr Leu Thr Ile Ser Gly Val Gln
65                  70                  75                  80

Ala Glu Asp Glu Ala Asp Tyr Tyr Cys Gly Ser Ile Asp Asn Ser Gly
                85                  90                  95

Ala Ala Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln

```
                     115                 120                 125
Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 43
<211> LENGTH: 702
<212> TYPE: DNA
<213> ORGANISM: Artificial Sequence
<220> FEATURE:
<223> OTHER INFORMATION: Coding sequence for humanized PS4 light chain

<400> SEQUENCE: 43
atggcctgga ttcctctact tctccccctc ctcactctct gcacaggatc cgaggccgcc       60
ctcacgcagc cccttccgt  atcagtgtcg ccgggtcaga ccgcgaggat cacatgctcg      120
ggtggagggt cgagctatta cgccgggtcc tattactatg gtggtaccag caaaaaccc      180
ggacaggcgc cagtgactgt catctactat aacaacaagc gccccagcgg gattccggaa     240
agattctcgg gaagcctttc cggatcgacg aataccctga ctatttcggg ggtacaggcc     300
gaagatgagg ctgactacta ttgtggctca atcgacaatt ccggagcggc atttggaggc     360
ggtacaaagt tgacggtcct ggtcagccc  aaggctgccc cctcggtcac cctgttcccg     420
ccctcctctg aggagcttca agccaacaag gccacactgg tgtgtctcat aagtgacttc     480
tacccgggag ccgtgacagt ggcctggaag gcagatagca gccccgtcaa ggcgggagtg     540
gagaccacca cacctccaa  acaaagcaac aacaagtacg cggccagcag ctatctgagc     600
ctgacgcctg agcagtggaa gtcccacaga agctacagct gccaggtcac gcatgaaggg     660
agcaccgtgg agaagacagt ggccccctaca gaatgttcat ag                        702

<210> SEQ ID NO 44
<211> LENGTH: 214
<212> TYPE: PRT
<213> ORGANISM: Artificial Sequence
<220> FEATURE:
<223> OTHER INFORMATION: Humanized PS4 light chain sequence

<400> SEQUENCE: 44

Glu Leu Thr Gln Pro Pro Ser Val Ser Val Ser Pro Gly Gln Thr Ala
1               5                   10                  15

Arg Ile Thr Cys Ser Gly Gly Gly Ser Ser Tyr Tyr Ala Gly Ser Tyr
            20                  25                  30

Tyr Tyr Gly Trp Tyr Gln Gln Lys Pro Gly Gln Ala Pro Val Thr Val
        35                  40                  45

Ile Tyr Tyr Asn Asn Lys Arg Pro Ser Gly Ile Pro Glu Arg Phe Ser
    50                  55                  60

Gly Ser Leu Ser Gly Ser Thr Asn Thr Leu Thr Ile Ser Gly Val Gln
65                  70                  75                  80

Ala Glu Asp Glu Ala Asp Tyr Tyr Cys Gly Ser Ile Asp Asn Ser Gly
```

```
            85                  90                  95
Ala Ala Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 45
<211> LENGTH: 702
<212> TYPE: DNA
<213> ORGANISM: Artificial Sequence
<220> FEATURE:
<223> OTHER INFORMATION: Coding sequence for humanized PS4 light chain

<400> SEQUENCE: 45
atggcctgga ttcctctact ctcccccctc ctcactctct gcacaggatc cgaggccgag      60
ctcacgcagc ccccttccgt atcagtgtcg ccgggtcaga ccgcgaggat cacatgctcg     120
ggtggagggt cgagctatta cgccgggtcc tattactatg ggtggtacca gcaaaaaccc     180
ggacaggcgc cagtgactgt catctactat aacaacaagc gccccagcgg gattccggaa     240
agattctcgg gaagccttc cggatcgacg aatacctga ctatttcggg ggtacaggcc     300
gaagatgagg ctgactacta ttgtggctca atcgacaatt ccggagcggc atttggaggc     360
ggtacaaagt tgacggtcct tggtcagccc aaggctgccc cctcggtcac cctgttcccg     420
ccctcctctg aggagcttca agccaacaag gccacactgg tgtgtctcat aagtgacttc     480
tacccgggag ccgtgacagt ggcctggaag gcagatagca gccccgtcaa ggcgggagtg     540
gagaccacca cccctccaa caaagcaac aacaagtacg cggccagcag ctatctgagc     600
ctgacgcctg agcagtggaa gtcccacaga agctacagct gccaggtcac gcatgaaggg     660
agcaccgtgg agaagacagt ggcccctaca gaatgttcat ag                       702

<210> SEQ ID NO 46
<211> LENGTH: 455
<212> TYPE: PRT
<213> ORGANISM: Artificial Sequence
<220> FEATURE:
<223> OTHER INFORMATION: Humanized PS4 heavy chain sequence

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Phe Trp Val Arg Gln Ala Pro Gly Lys Gly Leu Glu Trp Val
        35                  40                  45

Ala Gly Ile Asp Asp Asp Gly Ser Gly Arg Arg Tyr Ala Pro Ala Val
```

```
              50                  55                  60
Lys Gly Arg Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Lys Cys Ala Tyr Ser Ser Gly Cys Asp Tyr Glu Gly Gly Tyr Ile
            100                 105                 110

Asp Ala Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
450                 455

<210> SEQ ID NO 47
<211> LENGTH: 1425
```

<212> TYPE: DNA
<213> ORGANISM: Artificial Sequence
<220> FEATURE:
<223> OTHER INFORMATION: Coding sequence for humanized PS4 heavy chain

<400> SEQUENCE: 47

```
atggagttcg gcctgagctg ctgttcctg gtggccatcc ttaagggcgt gcagtgcgag      60
gtccagcttg tagaatcagg aggaggtttg gtgcaacccg agggtcact gcgcctctcg     120
tgcgcggcat cagggtttac gttctcctcg tatgatatgt ctgggtgag gcaggcccct     180
ggcaaagggc tggagtgggt ggcgggtatt gatgacgacg gatcgggcag acggtacgca     240
ccggccgtca agggacgagc gaccatcagc cgcgataaca gcaagaacac gttgtatctc     300
cagatgaatt cccttcgggc tgaggacacc gcggtctact attgtacaaa atgtgcgtat     360
tcgagcggat gcgattacga aggggttac atcgacgcat ggggacaggg gacgctggtc     420
actgtgtcgt ccgctagcac caagggccca tcggtcttcc ccctggcacc ctcctccaag     480
agcacctctg gggcacagc ggccctgggc tgcctggtca aggactactt ccccgaaccg     540
gtgacggtgt cgtggaactc aggcgccctg accagcggcg tgcacacctt cccggctgtc     600
ctacagtcct caggactcta ctccctcagc agcgtggtga ccgtgccctc cagcagcttg     660
ggcacccaga cctacatctg caacgtgaat cacaagccca gcaacaccaa ggtggacaag     720
aaagttgagc ccaaatcttg tgacaaaact cacacatgcc caccgtgccc agcacctgaa     780
ctcctggggg gaccgtcagt cttcctcttc cccccaaaac ccaaggacac cctcatgatc     840
tcccggaccc ctgaggtcac atgcgtggtg gtggacgtga gccacgaaga ccctgaggtc     900
aagttcaact ggtacgtgga cggcgtggag gtgcataatg ccaagacaaa gccgcgggag     960
gagcagtaca acagcacgta ccgtgtggtc agcgtcctca ccgtcctgca ccaggactgg    1020
ctgaatggca aggagtacaa gtgcaaggtc tccaacaaag ccctcccagc ccccatcgag    1080
aaaaccatct ccaaagccaa agggcagccc cgagaaccac aggtgtacac cctgccccca    1140
tcccgggatg agctgaccaa gaaccaggtc agcctgacct gcctggtcaa aggcttctat    1200
cccagcgaca tcgccgtgga gtgggagagc aatgggcagc cggagaacaa ctacaagacc    1260
acgcctcccg tgctggactc cgacggctcc ttcttcctct acagcaagct caccgtggac    1320
aagagcaggt ggcagcaggg gaacgtcttc tcatgctccg tgatgcatga ggctctgcac    1380
aaccactaca cacagaagag cctctccctg tctccgggta atga                    1425
```

<210> SEQ ID NO 48
<211> LENGTH: 5
<212> TYPE: PRT
<213> ORGANISM: Artificial Sequence
<220> FEATURE:
<223> OTHER INFORMATION: Glycine-serine polymer linker peptide

<400> SEQUENCE: 48

Gly Ser Gly Gly Ser
 1               5

<210> SEQ ID NO 49
<211> LENGTH: 5
<212> TYPE: PRT
<213> ORGANISM: Artificial Sequence
<220> FEATURE:
<223> OTHER INFORMATION: Glycine-serine polymer linker peptide

<400> SEQUENCE: 49

Gly Gly Gly Gly Ser
 1               5

<210> SEQ ID NO 50
<211> LENGTH: 4
<212> TYPE: PRT
<213> ORGANISM: Artificial Sequence
<220> FEATURE:
<223> OTHER INFORMATION: Glycine-serine polymer linker peptide

<400> SEQUENCE: 50

Gly Gly Gly Ser
 1

<210> SEQ ID NO 51
<211> LENGTH: 993
<212> TYPE: DNA
<213> ORGANISM: Homo sapiens

<400> SEQUENCE: 51

```
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag cgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacaca     960
cagaagagcc tctccctgtc tccgggtaaa tga                                  993
```

<210> SEQ ID NO 52
<211> LENGTH: 330
<212> TYPE: PRT
<213> ORGANISM: Homo sapiens

<400> SEQUENCE: 52

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
```

```
                        85                  90                  95
Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 53
<211> LENGTH: 321
<212> TYPE: DNA
<213> ORGANISM: Homo sapiens

<400> SEQUENCE: 53
ggtcagccca aggctgcccc ctcggtcacc ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca acaagtacgc ggccagcagc tatctgagcc tgacgcctga gcagtggaag     240
tcccacagaa gctacagctg ccaggtcacg catgaaggga gcaccgtgga agacagtg      300 gcccctacag aatgttcata g                                             321

<210> SEQ ID NO 54
<211> LENGTH: 106
<212> TYPE: PRT
<213> ORGANISM: Homo sapiens

<400> SEQUENCE: 54

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30
```

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 55
<211> LENGTH: 18
<212> TYPE: PRT
<213> ORGANISM: Gallus gallus

<400> SEQUENCE: 55

Ala Pro Gly Ser Ala Leu Val Thr Leu Ile Tyr Tyr Asn Asn Lys Arg
 1               5                  10                  15

Pro Ser

<210> SEQ ID NO 56
<211> LENGTH: 108
<212> TYPE: PRT
<213> ORGANISM: Artificial Sequence
<220> FEATURE:
<223> OTHER INFORMATION: Humanized PS4 light chain sequence

<400> SEQUENCE: 56

Ala Leu Thr Gln Pro Pro Ser Val Ser Val Ser Pro Gly Gln Thr Ala
 1               5                  10                  15

Arg Ile Thr Cys Ser Gly Gly Gly Ser Ser Tyr Tyr Ala Gly Ser Tyr
             20                  25                  30

Tyr Tyr Gly Trp Tyr Gln Gln Lys Pro Gly Gln Ala Pro Val Thr Val
             35                  40                  45

Ile Tyr Tyr Asn Asn Lys Arg Pro Ser Gly Ile Pro Glu Arg Phe Ser
 50                  55                  60

Gly Ser Leu Ser Gly Ser Thr Asn Thr Leu Thr Ile Ser Gly Val Gln
 65                  70                  75                  80

Ala Glu Asp Glu Ala Asp Tyr Tyr Cys Gly Ser Ile Asp Asn Ser Gly
                 85                  90                  95

Ala Ala Phe Gly Gly Gly Thr Lys Leu Thr Val Leu
            100                 105

<210> SEQ ID NO 57
<211> LENGTH: 110
<212> TYPE: PRT
<213> ORGANISM: Homo sapiens

<400> SEQUENCE: 57

Ser Tyr Glu Leu Thr Gln Pro Pro Ser Val Ser Val Ser Pro Gly Gln
 1               5                  10                  15

Thr Ala Arg Ile Thr Cys Ser Gly Gly Gly Ser Ser Tyr Tyr Ala Gly
             20                  25                  30

Ser Tyr Tyr Tyr Gly Trp Tyr Gln Gln Lys Pro Gly Gln Ala Pro Val
             35                  40                  45

Leu Val Ile Tyr Tyr Asn Asn Lys Arg Pro Ser Gly Ile Pro Glu Arg
 50                  55                  60

```
Phe Ser Gly Ser Asn Ser Gly Asn Thr Ala Thr Leu Thr Ile Ser Gly
 65                  70                  75                  80

Val Gln Ala Glu Asp Glu Ala Asp Tyr Tyr Cys Gly Ser Ile Asp Asn
                 85                  90                  95

Ser Gly Ala Ala Phe Gly Gly Gly Thr Lys Leu Thr Val Leu
            100                 105                 110

<210> SEQ ID NO 58
<211> LENGTH: 125
<212> TYPE: PRT
<213> ORGANISM: Artificial Sequence
<220> FEATURE:
<223> OTHER INFORMATION: Humanized PS4 heavy chain sequence

<400> SEQUENCE: 58

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Asp Met Phe Trp Val Arg Gln Ala Pro Gly Lys Gly Leu Glu Trp Val
         35                  40                  45

Ala Gly Ile Asp Asp Asp Gly Ser Gly Arg Arg Tyr Ala Pro Ala Val
 50                  55                  60

Lys Gly Arg Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Thr Lys Cys Ala Tyr Ser Ser Gly Cys Asp Tyr Glu Gly Gly Tyr Ile
            100                 105                 110

Asp Ala Trp Gly Gln Gly Thr Leu Val Thr Val Ser Ser
            115                 120                 125

<210> SEQ ID NO 59
<211> LENGTH: 125
<212> TYPE: PRT
<213> ORGANISM: Homo sapiens

<400> SEQUENCE: 59

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Asp Met Phe Trp Val Arg Gln Ala Pro Gly Lys Gly Leu Glu Trp Val
         35                  40                  45

Ser Gly Ile Asp Asp Asp Gly Ser Gly Arg Arg Tyr Ala Pro Ala Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Cys Ala Tyr Ser Ser Gly Cys Asp Tyr Glu Gly Gly Tyr Ile
            100                 105                 110

Asp Ala Trp Gly Gln Gly Thr Leu Val Thr Val Ser Ser
            115                 120                 125

<210> SEQ ID NO 60
<211> LENGTH: 214
<212> TYPE: PRT
<213> ORGANISM: Artificial Sequence
```

<220> FEATURE:
<223> OTHER INFORMATION: Humanized FS24 light chain with human lambda
      light chain constant region

<400> SEQUENCE: 60

```
Glu Leu Thr Gln Pro Pro Ser Val Ser Val Ser Pro Gly Gln Thr Ala
 1               5                  10                  15

Arg Ile Thr Cys Ser Gly Gly Ser Ser Tyr Tyr Ala Gly Ser Tyr
             20                  25                  30

Tyr Tyr Gly Trp Tyr Gln Gln Lys Pro Gly Gln Ala Pro Val Thr Leu
             35                  40                  45

Ile Tyr Tyr Asn Asn Lys Arg Pro Ser Gly Ile Pro Glu Arg Phe Ser
 50                  55                  60

Gly Ser Leu Ser Gly Ser Thr Asn Thr Leu Thr Ile Ser Gly Val Gln
 65                  70                  75                  80

Ala Glu Asp Glu Ala Asp Tyr Tyr Cys Gly Ser Ile Asp Asn Ser Gly
                 85                  90                  95

Ala Ala Phe Gly Gly Thr Lys Leu Thr Val Leu Gly Gln Pro Lys
                100                 105                 110

Ala Ala Pro Ser Val Thr Leu Phe Pro Pro Ser Ser Glu Glu Leu Gln
                115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
                180                 185                 190

Tyr Ser Cys Gln Val Thr His Glu Gly Ser Thr Val Glu Lys Thr Val
                195                 200                 205

Ala Pro Thr Glu Cys Ser
    210
```

<210> SEQ ID NO 61
<211> LENGTH: 702
<212> TYPE: DNA
<213> ORGANISM: Artificial Sequence
<220> FEATURE:
<223> OTHER INFORMATION: Coding sequence for humanized FS24 light chain

<400> SEQUENCE: 61

```
atggcctgga ttcctctact tctccccctc ctcactctct gcacaggatc cgaggccgag    60
ctcacgcagc cccttccgt  atcagtgtcg ccgggtcaga ccgcgaggat cacatgctcg   120 ggtggaggt  cgagctatta cgccgggtcc tattactatg gtgtacca   gcaaaaaccc   180 ggacaggcgc cagtgactct gatctactat aacaacaagc gccccagcgg gattccggaa   240
agattctcgg gaagcctttc cggatcgacg aatacctga  ctatttcggg ggtacaggcc   300
gaagatgagg ctgactacta ttgtggctca atcgacaatt ccggagcggc atttggaggc   360
ggtacaaagt tgacggtcct tggtcagccc aaggctgccc cctcggtcac cctgttcccg   420
cccctctctg aggagcttca agccaacaag gccacactgg tgtgtctcat aagtgacttc   480
tacccgggag ccgtgacagt ggcctggaag gcagatagca gccccgtcaa ggcgggagtg   540
gagaccacca cacctccaa  acaaagcaac aacaagtacg cggccagcag ctatctgagc   600
ctgacgcctg agcagtggaa gtcccacaga agctacagct gccaggtcac gcatgaaggg   660
```
agcaccgtgg agaagacagt ggcccctaca gaatgttcat ag          702

```
<210> SEQ ID NO 62
<211> LENGTH: 455
<212> TYPE: PRT
<213> ORGANISM: Artificial Sequence
<220> FEATURE:
<223> OTHER INFORMATION: Humanized FS24 heavy chain with human IgG1
      constant region

<400> SEQUENCE: 62
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ala Trp Val Arg Gln Ala Pro Gly Lys Gly Leu Glu Trp Val
        35                  40                  45

Ala Gly Ile Asp Tyr Asp Gly Ser Gly Arg Arg Tyr Ala Pro Ala Val
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Lys Cys Gly Tyr Thr Gly Cys Asp Tyr Glu Gly Gly Tyr Ile
            100                 105                 110

Asp Ala Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys

```
                     355                 360                 365
Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
                435                 440                 445

Leu Ser Leu Ser Pro Gly Lys
    450                 455

<210> SEQ ID NO 63
<211> LENGTH: 1425
<212> TYPE: DNA
<213> ORGANISM: Artificial Sequence
<220> FEATURE:
<223> OTHER INFORMATION: Coding sequence for humanized FS24 heavy chain

<400> SEQUENCE: 63
atggagttcg gcctgagctg gctgttcctg gtggccatcc ttaagggcgt gcagtgcgag     60
gtccagttgg tcgaatccgg agggggattg gtgcagcccg gtgggtcgct ccggctgtcg    120
tgcgccgcaa gcggttttac tttctcgtcg tatgatatgg cctgggtgcg ccaagcaccg    180
gggaaagggc ttgagtgggt agcggggatc gactacgacg gatcaggacg gcgctatgcg    240
ccagcagtga agggccgagc gacgatttca agagataact cgaaaaacac actgtacctc    300
caaatgaata gcttgagggc tgaagatacc gccgtctact attgtacgaa gtgcgggtac    360 acggaggct gtgactatga gggaggctac atcgacgcgt ggggtcaggg gactcttgta    420
acagtgtcct cagctagcac caagggccca tcggtcttcc ccctggcacc ctcctccaag    480
agcacctctg ggggcacagc ggccctgggc tgcctggtca aggactactt ccccgaaccg    540
gtgacggtgt cgtggaactc aggcgccctg accagcggcg tgcacacctt cccggctgtc    600
ctacagtcct caggactcta ctccctcagc agcgtggtga ccgtgccctc agcagcttg    660 ggcacccaga cctacatctg caacgtgaat cacaagccca gcaacaccaa ggtggacaag    720
aaagttgagc ccaaatcttg tgacaaaact cacacatgcc caccgtgccc agcacctgaa    780
ctcctggggg gaccgtcagt cttcctcttc cccccaaaac ccaaggacac cctcatgatc    840
tcccggaccc ctgaggtcac atgcgtggtg gtggacgtga gccacgaaga ccctgaggtc    900
aagttcaact ggtacgtgga cggcgtggag gtgcataatg ccaagacaaa gccgcgggag    960
gagcagtaca acagcacgta ccgtgtggtc agcgtcctca ccgtcctgca ccaggactgg   1020
ctgaatggca aggagtacaa gtgcaaggtc tccaacaaag ccctcccagc ccccatcgag   1080
aaaaccatct ccaaagccaa agggcagccc cgagaaccac aggtgtacac cctgccccca   1140
tcccgggatg agctgaccaa gaaccaggtc agcctgacct gcctggtcaa aggcttctat   1200
cccagcgaca tcgccgtgga gtgggagagc aatgggcagc cggagaacaa ctacaagacc   1260
acgcctcccg tgctggactc cgacggctcc ttcttcctct acagcaagct caccgtggac   1320
aagagcaggt ggcagcaggg gaacgtcttc tcatgctccg tgatgcatga ggctctgcac   1380
aaccactaca cacagaagag cctctccctg tctccgggta aatga                   1425

<210> SEQ ID NO 64
```

```
<211> LENGTH: 125
<212> TYPE: PRT
<213> ORGANISM: Gallus gallus

<400> SEQUENCE: 64

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Asn
            20                  25                  30

Ala Met Gly Trp Val Arg Gln Ala Pro Gly Lys Gly Leu Glu Trp Val
        35                  40                  45

Ala Gly Ile Asp Asp Asp Gly Ser Gly Thr Arg Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Thr Lys Cys Ala Tyr Ser Ser Gly Cys Asp Tyr Glu Gly Gly Tyr Ile
            100                 105                 110

Asp Ala Trp Gly His Gly Thr Glu Val Ile Val Ser Ser
        115                 120                 125

<210> SEQ ID NO 65
<211> LENGTH: 125
<212> TYPE: PRT
<213> ORGANISM: Gallus gallus

<400> SEQUENCE: 65

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Asp Met Ala Trp Val Arg Gln Glu Pro Gly Lys Gly Leu Glu Trp Val
        35                  40                  45

Ala Gly Ile Asp Asp Asp Gly Ser Gly Arg Arg Tyr Ala Pro Ala Val
    50                  55                  60

Lys Gly Arg Ala Thr Ile Ser Arg Asp Asn Gly Gln Ser Thr Leu Arg
65                  70                  75                  80

Leu Gln Leu Asn Asn Leu Arg Ala Glu Asp Thr Gly Thr Tyr Tyr Cys
                85                  90                  95

Thr Lys Cys Ala Tyr Ser Ser Gly Cys Asp Tyr Glu Gly Gly Tyr Ile
            100                 105                 110

Asp Ala Trp Gly His Gly Thr Glu Val Ile Val Ser Ser
        115                 120                 125

<210> SEQ ID NO 66
<211> LENGTH: 125
<212> TYPE: PRT
<213> ORGANISM: Gallus gallus

<400> SEQUENCE: 66

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Asp Met Ala Trp Val Arg Gln Glu Pro Gly Lys Gly Leu Glu Trp Val
        35                  40                  45

Ala Gly Ile Asp Asp Asp Gly Ser Gly Arg Arg Tyr Ala Pro Ala Val
```

-continued

```
                50                  55                  60
Lys Gly Arg Ala Thr Ile Ser Arg Asp Asn Gly Gln Ser Thr Leu Arg
 65                  70                  75                  80

Leu Gln Leu Asn Asn Leu Arg Ala Glu Asp Thr Gly Thr Tyr Tyr Cys
                 85                  90                  95

Thr Lys Cys Ala Tyr Thr Gly Cys Asp Tyr Glu Gly Gly Tyr Ile
                100                 105                 110

Asp Ala Trp Gly His Gly Thr Glu Val Ile Val Ser Ser
            115                 120                 125

<210> SEQ ID NO 67
<211> LENGTH: 125
<212> TYPE: PRT
<213> ORGANISM: Gallus gallus

<400> SEQUENCE: 67

Ala Val Thr Leu Asp Glu Ser Gly Gly Gly Leu Gln Thr Pro Gly Gly
  1               5                  10                  15

Ala Leu Ser Leu Val Cys Lys Ala Ser Gly Phe Thr Phe Ser Ser Tyr
                 20                  25                  30

Asp Met Ala Trp Val Arg Gln Glu Pro Gly Lys Gly Leu Glu Trp Val
             35                  40                  45

Ala Gly Ile Asp Tyr Asp Gly Ser Gly Arg Arg Tyr Ala Pro Ala Val
         50                  55                  60

Lys Gly Arg Ala Thr Ile Ser Arg Asp Asn Gly Gln Ser Thr Leu Arg
 65                  70                  75                  80

Leu Gln Leu Asn Asn Leu Arg Ala Glu Asp Thr Gly Thr Tyr Tyr Cys
                 85                  90                  95

Thr Lys Cys Gly Tyr Thr Gly Cys Asp Tyr Glu Gly Gly Tyr Ile
                100                 105                 110

Asp Ala Trp Gly His Gly Thr Glu Val Ile Val Ser Ser
            115                 120                 125

<210> SEQ ID NO 68
<211> LENGTH: 125
<212> TYPE: PRT
<213> ORGANISM: Gallus gallus

<400> SEQUENCE: 68

Ala Val Thr Leu Asp Glu Ser Gly Gly Gly Leu Gln Thr Pro Gly Gly
  1               5                  10                  15

Ala Leu Ser Leu Val Cys Lys Ala Ser Gly Phe Thr Phe Ser Ser Tyr
                 20                  25                  30

Asp Met Phe Trp Val Arg Gln Glu Pro Gly Lys Gly Leu Glu Trp Val
             35                  40                  45

Ala Gly Ile Asp Asp Asp Gly Ser Gly Arg Arg Tyr Ala Pro Ala Val
         50                  55                  60

Lys Gly Arg Ala Thr Ile Ser Arg Asp Asn Gly Gln Ser Thr Leu Arg
 65                  70                  75                  80

Leu Gln Leu Asn Asn Leu Arg Ala Glu Asp Thr Gly Thr Tyr Tyr Cys
                 85                  90                  95

Thr Lys Cys Ala Tyr Ser Ser Gly Cys Asp Tyr Glu Gly Gly Tyr Ile
                100                 105                 110

Asp Ala Trp Gly His Gly Thr Glu Val Ile Val Ser Ser
            115                 120                 125

<210> SEQ ID NO 69
```

```
<211> LENGTH: 375
<212> TYPE: DNA
<213> ORGANISM: Gallus Gallus

<400> SEQUENCE: 69
gccgtgacgt tggacgagtc cggggggcggc ctccagacgc ccgggggagc gctcagcctc     60
gtctgcaagg cctccgggtt caccttcagc agtaacgcca tgggttgggt gcgacaggcg    120
cccggcaagg ggctggagtg ggtcgctggt attgatgatg atggtagtgg cacaagatac    180
gcgccggcgg tgaagggccg tgccaccatc tcgagggaca acgggcagag cacactgagg    240
ctgcagctga acaacctcag ggctgaggac accggcacct actactgcac gaaatgtgct    300
tacagtagtg gttgtgatta tgaaggtggt tatatcgacg catggggcca cgggaccgaa    360
gtcatcgtct cctcc                                                     375

<210> SEQ ID NO 70
<211> LENGTH: 375
<212> TYPE: DNA
<213> ORGANISM: Gallus gallus

<400> SEQUENCE: 70
gccgtgacgt tggacgagtc cggggggcggc ctccagacgc ccgggggagc gctcagcctc     60
gtctgcaagg cctccgggtt caccttcagc agttacgaca tggcctgggt gcgacaggag    120
cccggcaagg ggctggagtg ggtcgctggt attgatgatg atggtagtgg cagaagatac    180
gcgccggcgg tgaagggccg tgccaccatc tcgagggaca acgggcagag cacactgagg    240
ctgcagctga acaacctcag ggctgaggac accggcacct attactgcac gaaatgtgct    300
tacagtagtg gttgtgatta tgaaggtggt tatatcgacg catggggcca cgggaccgaa    360
gtcatcgtct cctcc                                                     375

<210> SEQ ID NO 71
<211> LENGTH: 375
<212> TYPE: DNA
<213> ORGANISM: Gallus gallus

<400> SEQUENCE: 71
gccgtgacgt tggacgagtc cggggggcggc ctccagacgc ccgggggagc gctcagcctc     60
gtctgcaagg cctccgggtt caccttcagc agttacgaca tggcctgggt gcgacaggag    120
cccggcaagg ggctggagtg ggtcgctggt attgatgatg atggtagtgg cagaagatac    180
gcgccggcgg tgaagggccg tgccaccatc tcgagggaca acgggcagag cacactgagg    240
ctgcagctga acaacctcag ggctgaggac accggcacct attactgcac gaaatgtgct    300
tacactggtg gttgtgatta tgaaggtggt tatatcgacg catggggcca cgggaccgaa    360
gtcatcgtct cctcc                                                     375

<210> SEQ ID NO 72
<211> LENGTH: 375
<212> TYPE: DNA
<213> ORGANISM: Gallus gallus

<400> SEQUENCE: 72
gccgtgacgt tggacgagtc cggggggcggc ctccagacgc ccgggggagc gctcagcctc     60
gtctgcaagg cctccgggtt caccttcagc agttacgaca tggcctgggt gcgacaggag    120
cccggcaagg ggctggagtg ggtcgctggt attgattatg atggtagtgg cagaagatac    180
gcgccggcgg tgaagggccg tgccaccatc tcgagggaca acgggcagag cacactgagg    240
```

```
ctgcagctga acaacctcag ggctgaggac accggcacct attactgcac gaaatgtggt    300
tacactggtg gttgtgatta tgaaggtggt tatatcgacg catggggcca cgggaccgaa    360
gtcatcgtct cctcc                                                    375
```

<210> SEQ ID NO 73
<211> LENGTH: 375
<212> TYPE: DNA
<213> ORGANISM: Gallus gallus

<400> SEQUENCE: 73

```
gccgtgacgt tggacgagtc cggggcggc ctccagacgc ccggggagc gctcagcctc      60 gtctgcaagg cctccgggtt caccttcagc agttacgaca tgttctgggt gcgacaggag   120
cccggcaagg ggctggagtg ggtcgctggt attgatgatg atggtagtgg cagaagatac   180
gcgccggcgg tgaagggccg tgccaccatc tcgagggaca cgggcagag cacactgagg    240 ctgcagctga acaacctcag ggctgaggac accggcacct attactgcac gaaatgtgct   300
tacagtagtg gttgtgatta tgaaggtggt tatatcgacg catggggcca cgggaccgaa    360
gtcatcgtct cctcc                                                    375
```

<210> SEQ ID NO 74
<211> LENGTH: 5
<212> TYPE: PRT
<213> ORGANISM: Gallus gallus

<400> SEQUENCE: 74

Ser Asn Ala Met Gly
1               5

<210> SEQ ID NO 75
<211> LENGTH: 17
<212> TYPE: PRT
<213> ORGANISM: Gallus gallus

<400> SEQUENCE: 75

Gly Ile Asp Asp Asp Gly Ser Gly Thr Arg Tyr Ala Pro Ala Val Lys
1               5                   10                  15

Gly

<210> SEQ ID NO 76
<211> LENGTH: 16
<212> TYPE: PRT
<213> ORGANISM: Gallus gallus

<400> SEQUENCE: 76

Cys Ala Tyr Ser Ser Gly Cys Asp Tyr Glu Gly Gly Tyr Ile Asp Ala
1               5                   10                  15

<210> SEQ ID NO 77
<211> LENGTH: 5
<212> TYPE: PRT
<213> ORGANISM: Gallus gallus

<400> SEQUENCE: 77

Ser Tyr Asp Met Phe
1               5

<210> SEQ ID NO 78
<211> LENGTH: 10
<212> TYPE: PRT
<213> ORGANISM: Gallus gallus

```
<400> SEQUENCE: 78

Ser Tyr Asp Met Phe Trp Val Arg Gln Glu
 1               5                  10

<210> SEQ ID NO 79
<211> LENGTH: 5
<212> TYPE: PRT
<213> ORGANISM: Gallus gallus

<400> SEQUENCE: 79

Ser Tyr Asp Met Ala
 1               5

<210> SEQ ID NO 80
<211> LENGTH: 10
<212> TYPE: PRT
<213> ORGANISM: Gallus gallus

<400> SEQUENCE: 80

Ser Tyr Asp Met Ala Trp Val Arg Gln Glu
 1               5                  10

<210> SEQ ID NO 81
<211> LENGTH: 17
<212> TYPE: PRT
<213> ORGANISM: Gallus gallus

<400> SEQUENCE: 81

Gly Ile Asp Asp Asp Gly Ser Gly Arg Arg Tyr Ala Pro Ala Val Lys
 1               5                  10                  15

Gly

<210> SEQ ID NO 82
<211> LENGTH: 17
<212> TYPE: PRT
<213> ORGANISM: Gallus gallus

<400> SEQUENCE: 82

Gly Ile Asp Tyr Asp Gly Ser Gly Arg Arg Tyr Ala Pro Ala Val Lys
 1               5                  10                  15

Gly

<210> SEQ ID NO 83
<211> LENGTH: 16
<212> TYPE: PRT
<213> ORGANISM: Gallus gallus

<400> SEQUENCE: 83

Cys Ala Tyr Thr Gly Gly Cys Asp Tyr Glu Gly Gly Tyr Ile Asp Ala
 1               5                  10                  15

<210> SEQ ID NO 84
<211> LENGTH: 16
<212> TYPE: PRT
<213> ORGANISM: Gallus gallus

<400> SEQUENCE: 84

Cys Gly Tyr Thr Gly Gly Cys Asp Tyr Glu Gly Gly Tyr Ile Asp Ala
 1               5                  10                  15

<210> SEQ ID NO 85
<211> LENGTH: 13
<212> TYPE: PRT
<213> ORGANISM: Gallus gallus
```

<400> SEQUENCE: 85

Ser Gly Gly Gly Ser Tyr Ala Gly Ser Tyr Tyr Tyr Gly
1               5                   10

<210> SEQ ID NO 86
<211> LENGTH: 15
<212> TYPE: PRT
<213> ORGANISM: Gallus gallus

<400> SEQUENCE: 86

Ser Gly Gly Gly Ser Ser Tyr Tyr Ala Gly Ser Tyr Tyr Tyr Gly
1               5                   10                  15

<210> SEQ ID NO 87
<211> LENGTH: 110
<212> TYPE: PRT
<213> ORGANISM: Artificial Sequence
<220> FEATURE:
<223> OTHER INFORMATION: human V lamda subgroup III consensus sequence
<220> FEATURE:
<221> NAME/KEY: VARIANT
<222> LOCATION: 23, 24, 25, 26, 27, 28, 29, 30, 31, 32, 33, 34, 35, 36,
      37, 53, 54, 55, 56, 57, 58, 59, 92, 93, 94, 95, 96, 97, 98,
      99, 100
<223> OTHER INFORMATION: Xaa = Any Amino Acid

<400> SEQUENCE: 87

Ser Tyr Glu Leu Thr Gln Pro Pro Ser Val Ser Val Ser Pro Gly Gln
1               5                   10                  15

Thr Ala Arg Ile Thr Cys Xaa Xaa Xaa Xaa Xaa Xaa Xaa Xaa Xaa Xaa
            20                  25                  30

Xaa Xaa Xaa Xaa Xaa Trp Tyr Gln Gln Lys Pro Gly Gln Ala Pro Val
            35                  40                  45

Leu Val Ile Tyr Xaa Xaa Xaa Xaa Xaa Xaa Gly Ile Pro Glu Arg
50                  55                  60

Phe Ser Gly Ser Asn Ser Gly Asn Thr Ala Thr Leu Thr Ile Ser Gly
65                  70                  75                  80

Val Gln Ala Glu Asp Glu Ala Asp Tyr Tyr Cys Xaa Xaa Xaa Xaa Xaa
            85                  90                  95

Xaa Xaa Xaa Xaa Phe Gly Gly Gly Thr Lys Leu Thr Val Leu
            100                 105                 110

<210> SEQ ID NO 88
<211> LENGTH: 125
<212> TYPE: PRT
<213> ORGANISM: Artificial Sequence
<220> FEATURE:
<223> OTHER INFORMATION: human VH subgroup III consensus sequence
<220> FEATURE:
<221> NAME/KEY: VARIANT
<222> LOCATION: 31, 32, 33, 34, 35, 50, 51, 52, 53, 54, 55, 56, 57, 58,
      59, 60, 61, 62, 63, 64, 65, 66, 99, 100, 101, 102, 103, 104,
      105, 106, 107, 108, 109, 110, 111, 112, 113, 114
<223> OTHER INFORMATION: Xaa = Any Amino Acid

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Xaa
            20                  25                  30

Xaa Xaa Xaa Trp Val Arg Gln Ala Pro Gly Lys Gly Leu Glu Trp Val
            35                  40                  45

Ser Xaa Xaa Xaa Xaa Xaa Xaa Xaa Xaa Xaa Xaa Xaa Xaa Xaa Xaa Xaa

-continued

```
                50                  55                  60
Xaa Xaa Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Xaa Xaa Xaa Xaa Xaa Xaa Xaa Xaa Xaa Xaa Xaa Xaa Xaa Xaa
                100                 105                 110

Xaa Xaa Trp Gly Gln Gly Thr Leu Val Thr Val Ser Ser
        115                 120                 125

<210> SEQ ID NO 89
<211> LENGTH: 129
<212> TYPE: PRT
<213> ORGANISM: Homo sapiens

<400> SEQUENCE: 89

Met Ala Arg Gly Ser Leu Arg Arg Leu Leu Arg Leu Leu Val Leu Gly
  1               5                  10                  15

Leu Trp Leu Ala Leu Leu Arg Ser Val Ala Gly Glu Gln Ala Pro Gly
                 20                  25                  30

Thr Ala Pro Cys Ser Arg Gly Ser Ser Trp Ser Ala Asp Leu Asp Lys
                 35                  40                  45

Cys Met Asp Cys Ala Ser Cys Arg Ala Arg Pro His Ser Asp Phe Cys
             50                  55                  60

Leu Gly Cys Ala Ala Ala Pro Pro Ala Pro Phe Arg Leu Leu Trp Pro
 65                  70                  75                  80

Ile Leu Gly Gly Ala Leu Ser Leu Thr Phe Val Leu Gly Leu Leu Ser
                 85                  90                  95

Gly Phe Leu Val Trp Arg Arg Cys Arg Arg Arg Glu Lys Phe Thr Thr
                100                 105                 110

Pro Ile Glu Glu Thr Gly Gly Glu Gly Cys Pro Ala Val Ala Leu Ile
            115                 120                 125

Gln

<210> SEQ ID NO 90
<211> LENGTH: 125
<212> TYPE: PRT
<213> ORGANISM: Artificial Sequence
<220> FEATURE:
<223> OTHER INFORMATION: humanized FS24 heavy chain variable region

<400> SEQUENCE: 90

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Asp Met Ala Trp Val Arg Gln Ala Pro Gly Lys Gly Leu Glu Trp Val
                 35                  40                  45

Ala Gly Ile Asp Tyr Asp Gly Ser Gly Arg Arg Tyr Ala Pro Ala Val
             50                  55                  60

Lys Gly Arg Ala Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Lys Cys Gly Tyr Thr Gly Gly Cys Asp Tyr Glu Gly Gly Tyr Ile
                100                 105                 110

Asp Ala Trp Gly Gln Gly Thr Leu Val Thr Val Ser Ser
            115                 120                 125
```

<210> SEQ ID NO 91
<211> LENGTH: 108
<212> TYPE: PRT
<213> ORGANISM: Artificial Sequence
<220> FEATURE:
<223> OTHER INFORMATION: humanized FS24 light chain variable region

<400> SEQUENCE: 91

Glu Leu Thr Gln Pro Pro Ser Val Ser Val Ser Pro Gly Gln Thr Ala
1               5                   10                  15

Arg Ile Thr Cys Ser Gly Gly Gly Ser Ser Tyr Tyr Ala Gly Ser Tyr
            20                  25                  30

Tyr Tyr Gly Trp Tyr Gln Gln Lys Pro Gly Gln Ala Pro Val Thr Leu
        35                  40                  45

Ile Tyr Tyr Asn Asn Lys Arg Pro Ser Gly Ile Pro Glu Arg Phe Ser
    50                  55                  60

Gly Ser Leu Ser Gly Ser Thr Asn Thr Leu Thr Ile Ser Gly Val Gln
65                  70                  75                  80

Ala Glu Asp Glu Ala Asp Tyr Tyr Cys Gly Ser Ile Asp Asn Ser Gly
                85                  90                  95

Ala Ala Phe Gly Gly Gly Thr Lys Leu Thr Val Leu
            100                 105

<210> SEQ ID NO 92
<211> LENGTH: 17
<212> TYPE: PRT
<213> ORGANISM: Artificial Sequence
<220> FEATURE:
<223> OTHER INFORMATION: consensus VHCDR2 of FS24, FS17 and FS10
<220> FEATURE:
<221> NAME/KEY: VARIANT
<222> LOCATION: (4)...(4)
<223> OTHER INFORMATION: Xaa = Asp or Tyr

<400> SEQUENCE: 92

Gly Ile Asp Xaa Asp Gly Ser Gly Arg Arg Tyr Ala Pro Ala Val Lys
1               5                   10                  15

Gly

<210> SEQ ID NO 93
<211> LENGTH: 16
<212> TYPE: PRT
<213> ORGANISM: Artificial Sequence
<220> FEATURE:
<223> OTHER INFORMATION: consensus VHCDR3 of FS24, FS17, and and FS10
<220> FEATURE:
<221> NAME/KEY: VARIANT
<222> LOCATION: (2)...(2)
<223> OTHER INFORMATION: Xaa = Ala or Gly
<220> FEATURE:
<221> NAME/KEY: VARIANT
<222> LOCATION: (4)...(4)
<223> OTHER INFORMATION: Xaa = Ser or Thr
<220> FEATURE:
<221> NAME/KEY: VARIANT
<222> LOCATION: (5)...(5)
<223> OTHER INFORMATION: Xaa = Ser or Gly

<400> SEQUENCE: 93

Cys Xaa Tyr Xaa Xaa Gly Cys Asp Tyr Glu Gly Gly Tyr Ile Asp Ala
1               5                   10                  15

<210> SEQ ID NO 94
<211> LENGTH: 9

```
<212> TYPE: PRT
<213> ORGANISM: Artificial Sequence
<220> FEATURE:
<223> OTHER INFORMATION: consensus VLCDR3 of FS24, FS17 and FS10
<220> FEATURE:
<221> NAME/KEY: VARIANT
<222> LOCATION: (3)...(3)
<223> OTHER INFORMATION: Xaa = Ala or Ile

<400> SEQUENCE: 94

Gly Ser Xaa Asp Asn Ser Gly Ala Ala
 1               5
```